US011937586B2

(12) United States Patent
Koentgen

(10) Patent No.: US 11,937,586 B2
(45) Date of Patent: *Mar. 26, 2024

(54) COMPOSITIONS AND METHODS FOR PRODUCING GENETICALLY MODIFIED ANIMALS

(71) Applicant: OZGENE HOLDINGS PTY LTD., Bentley (AU)

(72) Inventor: Frank Koentgen, North Beach (AU)

(73) Assignee: OZGENE HOLDINGS PTY LTD, Bentley (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/538,206

(22) Filed: Nov. 30, 2021

(65) Prior Publication Data
US 2022/0201992 A1 Jun. 30, 2022

Related U.S. Application Data

(62) Division of application No. 15/034,970, filed as application No. PCT/AU2014/050339 on Nov. 7, 2014.

(30) Foreign Application Priority Data

Nov. 7, 2013 (AU) .................. 2013904307
Jun. 6, 2014 (AU) .................. 2014902162

(51) Int. Cl.
| A01K 67/027 | (2006.01) |
| A01K 67/0271 | (2024.01) |
| A01K 67/0276 | (2024.01) |
| C12N 5/0735 | (2010.01) |
| C12N 15/85 | (2006.01) |

(52) U.S. Cl.
CPC ...... *A01K 67/0276* (2013.01); *A01K 67/0271* (2013.01); *C12N 5/0606* (2013.01); *C12N 15/8509* (2013.01); *A01K 2207/12* (2013.01); *A01K 2217/075* (2013.01); *A01K 2227/105* (2013.01); *A01K 2267/025* (2013.01); *C12N 2510/00* (2013.01); *C12N 2800/30* (2013.01)

(58) Field of Classification Search
CPC ............ A01K 67/0276; A01K 67/0271; A01K 2207/12; A01K 2217/075; A01K 2227/105; A01K 2267/025; C12N 5/0606; C12N 15/8509; C12N 2510/00; C12N 2800/30
See application file for complete search history.

(56) References Cited

U.S. PATENT DOCUMENTS

| 2005/0125853 A1 | 6/2005 | Parekh |
| 2005/0176943 A1 | 8/2005 | Nishimune et al. |
| 2006/0085866 A1 | 4/2006 | Poueymirou et al. |
| 2012/0167242 A1 | 6/2012 | Wiles et al. |
| 2013/0211187 A1 | 8/2013 | Araki |
| 2016/0360736 A1 | 12/2016 | Koentgen |

FOREIGN PATENT DOCUMENTS

| WO | WO 2003/071869 A1 | 9/2003 |
| WO | WO 2003/081990 A2 | 10/2003 |
| WO | WO 2010/131285 A1 | 11/2010 |

OTHER PUBLICATIONS

Jamsai et al. "Mouse models in male fertility research." Asian J Androl. Jan. 2011; 13(1): 139-151. (Year: 2011).*
Vockel et al. "The X chromosome and male infertility." Hum Genet Jan. 2021; 140(1):203-215. (Year: 2019).*
Zheng et al. "Regulation of Male Fertility by X-Linked Genes." Journal of Andrologyvol. 31, Issue 1 p. 79-85., Jan./Feb. 2010 (Year: 2010).*
Gao, Sheng, et al. "Mageb4, a testis-specific gene, is dispensable for mouse spermatogenesis." Reproductive and Developmental Medicine 4.3 (2020): 129. (Year: 2020).*
Mihalo et al. "Histone methyltransferase PRDM9 is not essential for meiosis in male mice." Genome Res .Jul. 2019;29(7):1078-1086. (Year: 2019).*
Yu et al. "The Dispensable Roles of X-Linked Ubl4a and Its Autosomal Counterpart Ubl4b in Spermatogenesis Represent a New Evolutionary Type of X-Derived Retrogenes." Front Genet .Jun. 25, 2021;12:689902. (Year: 2021).*
Roy et al. "Deconstructing mammalian reproduction: using knockouts to define fertility pathways." Reproduction . Feb. 2006;131(2):207-19. (Year: 2006).*

(Continued)

*Primary Examiner* — Titilayo Moloye

(74) *Attorney, Agent, or Firm* — Knobbe, Martens, Olson & Bear LLP

(57) ABSTRACT

Methods, compositions and non-human animals and parts thereof are for improving germ line transmission of genetic modifications. The methods and compositions are for producing non-human embryos with a disrupted or disruptable fertility gene. The embryos can be used as hosts for the development of donor pluripotent cells, including genetically modified donor pluripotent cells, into germ cells and gametes. Additional methods and compositions are for producing from such embryos chimeric non-human animals with a disrupted fertility gene and for breeding the chimeric non-human animals with cognate non-human animals that comprise a fertility gene that lacks a disruption to produce non-human animals having substantially all gametes and/or germ cells derived from the donor pluripotent cells. Non-human gametes, germ cells, embryos and animals can be used in the subject methods.

12 Claims, 3 Drawing Sheets

Specification includes a Sequence Listing.

(56) References Cited

OTHER PUBLICATIONS

Blaeser et al. "CaMKIV/Gr is dispensable for spermatogenesis and CREM-regulated transcription in male germ cells." Am J Physiol Endocrinol Metab . Nov. 2001;281(5):E931-7. (Year: 2011).*
Sakai et al. "Usp26 mutation in mice leads to defective spermatogenesis depending on genetic background." Sci Rep . Sep. 24, 2019;9(1):13757. (Year: 2019).*
Wosnitzer et al. "Ubiquitin Specific Protease 26 (USP26) expression analysis in human testicular and extragonadal tissues indicates diverse action of USP26 in cell differentiation and tumorigenesis." PLoS One . Jun. 12, 2014;9(6):e98638. (Year: 2014).*
Guo et al. "Contribution of Mouse Embryonic Stem Cells and Induced Pluripotent Stem Cells to Chimeras through Injection and Coculture of Embryos." Stem Cells Int. 2014; 2014: 409021. (Year: 2014).*
Stouffs et al., Male infertility and the involvement of the X chromosome, Human Reproduction Update, vol. 15, No. 6, pp. 623-637, 2009.
Zheng et al., Regulation of Male Fertility by X-Linked Genes, Journal of Andrology, vol. 13, No. 1, pp. 79-85, 2010.
3R's Committee, "And the inaugural ISTT 3Rs Prize winner is . . . ", International Society for Transgenic Technologies (ISTT, Inc.), Jul. 17, 2017.
Brevini et al. "Porcine embryonic stem cells: Facts, challenges and hopes." Theriogenology. Sep. 1, 2007 ;68 Suppl 1 :S206-13. Epub Jun. 19, 2007.
Cattanach, B.M., et al., Mouse News Letter, No. 38, pp. 17-18, 1968.
Cesari, F., et al., Mice Deficient for the Ets Transcription Factor Elk-1 Show Normal Immune Responses and Mildly Impaired Neuronal Gene Activation, Molecular and Cellular Biology, vol. 24, No. 1, pp. 294-305, 2004.
Cesari, F., et al., Elk-1 Knock-Out Mice Engineered by Flp Recombinase-Mediated Cassette Exchange, Genesis, vol. 38, No. 2, pp. 87-92, 2004.
Chang, C., et al., Infertility With Defective Spermatogenesis and Hypotestosteronemia in Male Mice Lacking the Androgen Receptor in Sertoli Cells, Proceedings of the National Academy of Sciences of the United States of America, vol. 101, No. 18, pp. 6876-6881, 2004.
Cohen, N.R., et al., Errors in Corticospinal Axon Guidance in Mice Lacking the Neural Cell Adhesion Molecule L1, Current Biology, vol. 8, pp. 26-33, 1997.
Dechiara, T.M., et al., VelociMouse: Fully ES Cell-Derived F0-Generation Mice Obtained from the Injection of ES Cells into Eight-Cell-Stage Embryos, Methods in Molecular Biology, vol. 530, pp. 311-324, 2009.
Guan, K., et al., Pluripotency of Spermatogonial Stem Cells From Adult Mouse Testis, Nature, vol. 44, pp. 1199-1203, 2006.
Hamanaka, S., et al., Generation of Germline-Competent Rat Induced Pluripotent Stem Cells, PLoS One, vol. 6, No. 7, e22008, 2011.
Horii, T., et al., Serum-Free Culture of Murine Frimodial Germ Cells and Embryonic Germ Cells, Theriogenology, vol. 59, pp. 1257-1264, 2003.
Hughes, J., et al., Mechanistic Insight into the Pathology of Polyalanine Expansion Disorders Revealed by a Mouse Model for X Linked Hypopituitarism, PLOS Genetics, vol. 9, No. 3, e10003290, 2013.
Hu et al., Efficient production of chimeric mice from embryonic stem cells injected into 4- to 8-cell and blastocyst embryos, Journal of Animal Science and Biotechnology, vol. 4, No. 12, pp. 1-7, 2013.
Huang et al., Efficient Production of Mice from Embryonic Stem Cells Injected into Four- or Eight-Cell Embryos by Piezo Micromanipulation, Stem Cells, vol. 26, pp. 1883-1890, 2008.
Ingman et al., "Null Mutation in Transforming Growth Factor B1 Disrupts Ovarian Function and Causes Oocyte Incompetence and Early Embryo Arrest," Endocrinol 147, pp. 835-845; pgs., (2006).
Jamsai, D., et al., Mouse models in male fertility research, Asian Journal of Andrology, vol. 13, No. 1, pp. 139-151, 2011.
Jeffs et al., Sertoli Cell-Specific Rescue of Fertility, But Not Testicular Pathology, in Dax1 (Ahch)-Deficient Male Mice, Endocrinology, vol. 142, No. 6, pp. 2481-2488, 2001.
Jentarra, G.M., et al. Abnormalities of cell packing density and dendritic complexity in the MeCP2 A140V mouse model of Rett syndrome/X-linked mental retardation, BMC Neuroscience, 11:19, 2010.
Jung, D.O., et al., The Forkhead Transcription Factor, Foxp3, Is Required for Normal Pituitary Gonadotropin Expression in Mice, Biology of Reproduction, vol. 86, No. 5, Article 144, pp. 1-9, 2012.
Kanatsu-Shinohara, M., et al., Culture and Genetic Modification of Mouse Germline Stem Cells, Annals of the New York Academy of Sciences, vol. 1120, pp. 59-71, 2007.
Kanatsu-Shinohara, M., et al., Germline Modification Using Mouse Spermatogonial Stem Cells, Methods in Enzymology, vol. 477, pp. 17-36, 2010.
Kaneda et al., "Essential role for de novo DNA methyltransferase Dnmt3a in paternal and maternal imprinting," Nature 429, pp. 900-903; pgs., (2004).
$Kit^W$, Spontaneous Allele Detail MGI Mouse (MGI: 1856232), The Jackson Laboratory, retrieved on Dec. 18, 2018 from http://www.informatics.jax.org/allele/key/363, last updated Dec. 11, 2018.
Koentgen, F., et al., Exclusive Transmission of the Embryonic Stem Cell-Derived Genome Through the Mouse Germline, Genesis, vol. 54, No. 6, pp. 326-333, 2016.
Kudoh, H., et al., A New Model Mouse for Duchenne Muscular Dystrophy Produced by 2.4 Mb Deletion of Dystrophin Gene Using Cre-Loxp Recombination System, Biochemical and Biophysical Research Communications, vol. 328, pp. 507-516, 2005.
Kumar et al. "Of Mice and Men: In Vivo and In Vitro Studies of Primordial Germ Cell Specification." Semin Reprod Med. Mar. 2017; 35(2): 139-146.
Li, C., et al., Germline-Competent Mouse-Induced Pluripotent Stem Cell Lines Generated on Human Fibroblasts without Exogenous Leukemia Inhibitory Factor, Mouse iPSC on Human Feeders, PLoS One, vol. 4, No. 8, e6724, 2009.
Mikolcevic, P., et al., Cyclin-Dependent Kinase 16/PCTAIRE Kinase 1 Is Activated by Cyclin Y and Is Essential for Spermatogenesis, Molecular and Cellular Biology, vol. 32, No. 4, pp. 868-879, 2012.
Nagao, Y., et al., Decreased Physical Performance of Congenic Mice With Mismatch Between the Nuclear and the Mitochondrial Genome, Genes and Genetic Systems, vol. 73, pp. 21-27, 1998.
Nakayama, H., et al., Growth Competition Between W Mutant and Wild-Type Cells in Mouse Aggregation Chimeras, Development Growth & Differentiation, vol. 32, No. 3, pp. 255-261, 1990.
Nakanishi et al., "Selective Passage Through the Uterotubal Junction of Sperm from a Mixed Population Produced by Chimeras of Calmegin-Knockout and Wild-Type Male Mice," Biol Reprod 71, pp. 959-965; pgs., (2004).
Okita, K., et al., Generation of Germline-Competent Induced Pluripotent Stem Cells, Nature, vol. 448, pp. 313-318, 2007.
Okumura et al. "Germ cell nuclear factor is not required for the down-regulation of pluripotency markers in fetal ovarian germ cell." Thesis (Ph. D.)—Massachusetts Institute of Technology, Dept. of Biology, 2012.
Pan, J. et al., Inactivation of Nxt2 causes defects in male meiosis and age-dependent depletion of spermatogonia, Developmental Biology, vol. 330, pp. 167-174, 2009.
Polejaeva et al., "Stem cell potency and the ability to contribute to chimeric organisms" Reproduction. Mar. 2013; 145(3): R81-R88.
"Rodent," https://www.britannica.com/animal/rodent. Encyclopaedia Britannica. Date accessed Oct. 7, 2019.
Romero et al., "The Glucocorticoid-Induced Leucine Zipper (GILZ) Is Essential for Spermatogonial Survival and Spermatogenesis," Sex dev 6, pp. 169-177; pgs., (2012).
Saburi et al., Developmental fate of single embryonic stem cells microinjected into 8-cell-stage mouse embryos, Differentiation, vol. 62, pp. 1-11, 1997.
Suarez et al., "The Glucocorticoid-Induced Leucine Zipper (Gilz/Tsc22d3-2) Gene Locus Plays a Crucial Role in Male Fertility," Mol Endocrinol 26, pp. 1000-1013; 14 pgs. (2012).
Suzuki, O., et al., Effect of Genetic Background on Establishment of Mouse Embryonic Stem Cells, Experimental Animals, vol. 48, No. 3, pp. 213-216, 1999.

(56) References Cited

OTHER PUBLICATIONS

Taft et al., "The Perfect Host: A Mouse Host Embryo Facilitating More Efficient Germ Line Transmission of Genetically Modified Embryonic Stem Cells," PloS ONE 8(7), e67826; 7 pgs., (2013).
Vaiman, D., Fertility, Sex Determination, and the X Chromosome, Cytogenetic and Genome Research, vol. 99, pp. 224-228, 2002.
Yang, F., et al., Meiotic Failure in Male Mice Lacking an X-Linked Factor, Genes & Development, vol. 22, pp. 682-691, 2008.
Phenotypes associated with Artm1Chc/Y Plekha5Tg(AMH-cre)1Flor/0, Mouse Genome Information, Last Database Update Aug. 1, 2019 http://www.informatics.jax.org/allele/genoview/MGI:3773622?counter=4 and http://www.informatics.jax.org/allele/MGI:2451025.
Phenotypes associated with Atp7aMo-vbr/Y, Mouse Genome Information, Last Database Update Jul. 27, 2019.http://www.informatics.jax.org/allele/allgenoviews/MGI:1856102 and http://www.informatics.jax.org/allele/key/201.
Phenotypes associated with Cdk16tm1.2Stge/Cdk16tm1.2Stge, Mouse Genome Information, Last Database Update Jul. 23, 2019.http://www.informatics.jax.org/allele/key/818113 and http://www.informatics.jax.org/allele/allgenoviews/MGI:5319210.
Phenotypes associated with Dmdtm1.1Khan/Y Mouse Genome Information, Last Database Update Jul. 23, 2019. http://www.informatics.jax.org/allele/key/37094 and http://www.informatics.jax.org/allele/allgenoviews/MGI:3531484.
Phenotypes associated with Elk1tm1Nor/Y, Mouse Genome Information, Last Database Update Jul. 23, 2019 http://www.informatics.jax.org/allele/key/26343 and http://www.informatics.jax.org/allele/allgenoviews/MGI:3028871.
Phenotypes associated with Foxp3tm2Flv/Y Mouse Genome Information, Last Database Update Jul. 23, 2019. http://www.informatics.jax.org/allele/key/52324 and http://www.informatics.jax.org/allele/allgenoviews/MGI:3700150.
Phenotypes associated with L1camtm1Sor/Y, Mouse Genome Information, Last Database Update Jul. 23, 2019 http://www.informatics.jax.org/allele/key/1644 and http://www.informatics.jax.org/allele/allgenoviews/MGI:1857443.
Phenotypes associated with Mecp2tm1.1Vnar/Mecp2tm1.1Vnar, Mouse Genome Information, Last Database Update Jul. 23, 2019 .http://www.informatics.jax.org/allele/key/640490 and http://www.informatics.jax.org/allele/allgenoviews/MGI:4949886.
Phenotypes associated with Nr0b1tm1.1Lja/Y, Mouse Genome Information, Last Database Update Jul. 23, 2019. http://www.informatics.jax.org/allele/key/6113 and http://www.informatics.jax.org/allele/allgenoviews/MGI:2159321.
Phenotypes associated with Sox3 tm1Pqt/Y, Mouse Genome Information, Last Database Update Jul. 23, 2019. http://www.informatics.jax.org/allele/key/837044 and http://www.informatics.jax.org/allele/allgenoviews/MGI:5504449.
Phenotypes associated with Tex11tm1Jw/Y Tmem163Tg(ACTB-cre)2Mrt/0, Mouse Genome Information, Last Database Update Jul. 23, 2019. http://www.informatics.jax.org/allele/key/35154 and http://www.informatics.jax.org/allele/allgenoviews/MGI:3526163.
Phenotypes associated with Nxf2tm1.2Jw/Y Last Update Jul. 23, 2019 http://www.informatics.jax.org/allele/key/67955 and http://www.informatics.jax.org/allele/allgenoviews/MGI:3848439.

International Search Report dated Dec. 23, 2014 in International Application No. PCT/AU2014/050339 in 4 pages.
Written Opinion dated Dec. 23, 2014 in International Application No. PCT/AU2014/050339 in 6 pages.
International Preliminary Report On Patentability dated May 8, 2015 in International Application No. PCT/AU2014/050339 in 5 pages.
$Kit^{W-v}$, Spontaneous Allele Detail MGI Mouse (MGI: 1856266), The Jackson Laboratory, retrieved on Dec. 18, 2018 from http://www.informatics.jax.org/allele/key/397, last updated Dec. 11, 2018.
Phenotypes associated with Tsc22d3tm1.2Hum/Y, last database update Nov. 8, 2022, http://www.informatics.jax.org/allele/genoview/MGI:5698212.
Zvick et al., Exclusive generation of rat spermatozoa in sterile mice utilizing blastocyst complementation with pluripotent stem cells, Stem Cell Reports, vol. 17, pp. 1942-1958, 2022.
Prdm9 Gene Detail; Downloaded Jan. 31, 2023 from https://www.informatics.jax.org/marker/MGI:2384854; Last updated Jan. 24, 2023.
Ubl4a Gene Detail; Downloaded Jan. 31, 2023 from https://www.informatics.jax.org/marker/MGI:95049; Last updated Jan. 24, 2023.
Adelman et al. ZIP4H (TEX11) Deficiency in the Mouse Impairs Meiotic Double Strand Break Repair and the Regulation of Crossing Over. *PLoS Genet.* Mar. 2, 20088; 4(3):e1000042.
Bruscoli et al. Long glucocorticoid-induced leucine zipper (L-GILZ) protein interacts with ras protein pathway and contributes to spermatogenesis control. J Biol Chem. Jan. 6, 2012; 287(2):1242-51.
$Camk4^{tm1Arm}$ Targeted Allele Detail; MGI:2158694; last database update Jul. 4, 2023.
Christiansen et al. Sequence analysis of the X-linked USP26 gene in severe male factor infertility patients and fertile controls. Fertil Steril. Sep. 2008; 90(3):851-2.
Jeffs et al. Blockage of the Rete Testis and Efferent Ductules by Ectopic Sertoli and Leydig Cells Causes Infertility in Dax1-Deficient Male Mice. Endocrinology. Oct. 2001; 142(10):4486-95.
Nr0b1 Gene Detail; MGI:1352460; last database update Jul. 4, 2023.
Phenotypes associated with $Tnp2^{tm1Wen}/Tnp2^{tm1Wen}$; MGI:3037939; last database update Jul. 4, 2023.
Ravel et al. Haplotypes, mutations and male fertility: the story of the testis-specific ubiquitin protease USP26. Mol Hum Reprod. Oct. 2006; 12(10):643-6.
Stouffs et al. Alterations of the USP26 gene in Caucasian men. Int J Androl. Dec. 2006; 29(6):614-7.
Tex11 Gene Detail; MGI:1933237; last database update Jul. 4, 2023.
$Tsc22d3^{tm1.1Ric}$ Targeted Allele Detail; MGI:5308358; last database update Jul. 4, 2023.
Wu et al. Spermiogenesis and exchange of basic nuclear proteins are impaired in male germ cells lacking Camk4. Nat Genet. Aug. 2000; 25(4):448-52.
Yang et al. Meiotic failure in male mice lacking an X-linked factor. Genes Dev. Mar. 1, 2008; 22(5):682-91.
Yu et al. Role of Ahch in gonadal development and gametogenesis. Nat Genet. Dec. 1998; 20(4):353-7.

\* cited by examiner

COMPOSITIONS AND METHODS FOR PRODUCING GENETICALLY MODIFIED ANIMALS

RELATED APPLICATIONS

This application is a Divisional Application of U.S. application Ser. No. 15/034,970, filed May 6, 2016, which is the U.S. National Stage Application under 35 U.S.C. § 371 of International Application No. PCT/AU2014/050339, filed Nov. 7, 2014, designating the U.S. and published in English as WO 2015/066768 A1 on May 14, 2015, which claims priority to Australian Provisional Application No. 2013904307 entitled "Compositions and Methods for Producing Genetically Modified Animals" filed 7 Nov. 2013, and to Australian Provisional Application No. 2014902162 entitled "Compositions and Methods for Producing Genetically Modified Animals" filed 6 Jun. 2014, the contents of each of which are incorporated herein by reference in their entirety.

REFERENCE TO ELECTRONIC SEQUENCE LISTING

The present application is filed along with an Electronic Sequence Listing. The Electronic Sequence Listing is provided as a file entitled DAVI538001D1SEQLIST.txt which is 2,407 bytes in size, created on Feb. 2, 2022. The information in the Electronic Sequence Listing is incorporated herein by reference in its entirety.

FIELD OF THE INVENTION

This invention relates generally to methods and compositions for producing non-human embryos with a disrupted or disruptable fertility gene, which can be used as hosts for the development of donor pluripotent cells, including genetically modified donor pluripotent cells, into germ cells and gametes. The present invention also relates to methods and compositions for producing from such embryos chimeric non-human animals with a disrupted fertility gene and for breeding the chimeric non-human animals with cognate non-human animals that comprise a fertility gene that lacks a disruption to produce non-human animals having substantially all gametes and/or germ cells derived from the donor pluripotent cells.

BACKGROUND OF THE INVENTION

Mouse embryonic stem (ES) cells are pluripotent and can contribute to all tissues of a mouse after blastocyst injection. They can also be genetically manipulated with relative ease and have been used for the generation of genetically modified mice after introduction of targeted mutations into the genome (see e.g., Doetschman T et al., 1987. Nature 330: 576-578).

When introduced into the blastocyst embryonic environment mouse 'donor' ES cells with the genetic modification integrate into the inner cell mass of the host blastocyst and differentiate into somatic and germ cell lineages, eventually giving rise to mosaic mice known as chimeras. The differences in chimerism are due to different amounts of contribution of the donor ES cells to the blastocysts. The better the donor ES cells do in the blastocyst the more cells of the embryo are derived from the donor ES cells, which in turn enhances transmission of the genetic modification into the germ line (germ line transmission).

However, due to several complicating factors that are poorly understood, including (i) the requirement of donor ES cells to be in the right place at the right time for integrating into the inner cell mass (ICM) developmental process, (ii) the inherent (genetic and epigenetic) ability of donor ES cells to become primordial germ cells and to subsequently develop into functional gametes, and (iii) the competition between host and donor stem cells during embryonic development in conventional chimeras for the developmental niche to eventually become gametes, the germ line contribution from donor ES cells in chimeras is unpredictable and varies from 0% to 100%.

Accordingly, there is a need to improve germ line transmission of genetically modified pluripotent cells such ES cells and to speed the generation of pluripotent cells derived animals from chimeras.

SUMMARY OF THE INVENTION

The present invention stems in part from the determination that germ line transmission of a donor pluripotent cell (e.g., comprising a genetic modification) comprising an endogenous fertility gene can be significantly enhanced by disrupting the fertility gene in a pre-implantation non-human embryo into which the donor pluripotent cell is introduced. Implantation and gestation of the embryo in a suitable surrogate or foster non-human animal produces offspring including chimeric non-human animals comprising endogenous germ cells or gametes that comprise a disrupted fertility gene as well as chimeric non-human animals that comprise germ cells or gametes derived from the donor pluripotent cell that do not comprise a disruption in the fertility gene. When bred with a cognate non-human animal that comprises an undisrupted fertility gene, the chimeric non-human animals that comprise endogenous germ cells or gametes comprising a disrupted fertility gene will have impaired or inhibited fertility and those that comprise germ cells or gametes derived from the donor pluripotent cell will have normal or unimpaired fertility, thereby enhancing the production of first litter offspring comprising germ cells or gametes derived from the donor pluripotent cell.

Accordingly, in one aspect, the present invention provides a pre-implantation non-human host embryo comprising or consisting essentially of in its germ line a disrupted fertility gene. The fertility gene that is disrupted may be on any chromosome and in some embodiments, the fertility gene is located on a sex chromosome (e.g., X or Y chromosome). In specific embodiments, the fertility gene is located on the X chromosome. The disruption of the fertility gene may be heterozygous or homozygous and in specific embodiments, both alleles of the fertility gene are disrupted. Suitably, the disruption of the fertility gene inhibits male fertility and in illustrative examples of this type, the disruption inhibits sperm function or spermatogenesis. In specific embodiments, the fertility gene is GILZ.

In a related aspect, the present invention provides a pre-implantation non-human host embryo as broadly described above further comprising a donor pluripotent cell that comprises a fertility gene lacking a disruption thereof. In some embodiments, the donor pluripotent cell is a stem cell (e.g., selected from embryonic stem (ES) cells, epiblast stem cells, embryonic germ cells, induced pluripotent stem cells, genetically modified ES cells, genetically modified epiblast stem cells, genetically modified embryonic germ (EG) cells, genetically modified induced pluripotent stem (iPS) cells or a combination of any two or more of these).

Suitably, the pluripotent cell comprises a genetic modification. In specific embodiments, the donor pluripotent cell is a male pluripotent cell.

Another aspect of the present invention provides a non-human host embryo comprising a disrupted fertility gene as broadly defined above and elsewhere herein and a donor pluripotent cell that comprises a fertility gene lacking a disruption thereof. In some embodiments, the donor pluripotent cell is a stem cell (e.g., an ES cell) that suitably comprises a genetic modification. The donor pluripotent cell is suitably a male pluripotent cell.

In yet another aspect of the present invention, methods are provided for generating non-human animals. These methods generally comprise or consist essentially of introducing a pre-implantation non-human host embryo as broadly defined above and elsewhere herein into a pseudopregnant non-human animal and gestating the pre-implantation non-human host embryo under conditions suitable for development of the embryo, thereby generating a non-human animal.

In a related aspect, the present invention provides a non-human animal resulting from these methods.

Still another aspect of the present invention provides a surrogate or foster non-human animal comprising or consisting essentially of a non-human host embryo as broadly defined above and elsewhere herein.

In another aspect of the present invention, methods are provided for generating a chimeric non-human animal. These methods generally comprise or consist essentially of introducing into a pseudopregnant non-human animal a pre-implantation non-human host embryo as broadly defined above and elsewhere herein comprising a donor pluripotent cell that comprises a fertility gene lacking a disruption thereof and gestating the pre-implantation non-human host embryo under conditions suitable for development of the embryo, thereby generating a chimeric non-human animal.

In a related aspect, the present invention provides a chimeric non-human animal resulting from these methods.

Yet another aspect of the present invention provides methods for generating a non-human host embryo with a disrupted fertility gene. These methods generally comprise or consist essentially of crossing: 1) a first animal strain carrying a disruptable fertility gene; with 2) a second animal strain carrying an infertility-activating transgene that comprises a gene that disrupts the disruptable fertility gene, thereby generating transgenic non-human host embryos that comprise germ cells having a disrupted fertility gene. In some embodiments, female members of the first animal strain are crossed with male members of the second animal strain. As used herein, respective members of the first and second animal strains are breeding partners of a breeding pair of non-human animals.

In still another aspect, the present invention provides a breeding pair of non-human animals, comprising: (1) a first breeding partner comprising a disruptable fertility transgene that comprises a disruptable fertility gene as broadly described above and elsewhere herein, which is disruptable by a fertility gene disruptor molecule, wherein the disruptable fertility gene is operably connected to a promoter, and (2) a second breeding partner comprising a disruptor transgene that comprises a nucleotide sequence encoding the fertility gene disruptor molecule ("a disruptor nucleotide sequence"), wherein the disruptor nucleotide sequence is operably linked to a promoter. In some embodiments, the fertility gene disruptor molecule is a recombinase and the disruptable fertility gene is operably connected to recombinase recognition sites that mediate disruption of the disruptable fertility gene in the presence of the recombinase. In other embodiments, the fertility gene disruptor molecule is an inhibitory RNA molecule that inhibits the expression of the disruptable fertility gene, suitably by antisense suppression or RNA interference. In still other embodiments, the fertility gene disruptor molecule is an antibody that is immuno-interactive with a polypeptide product of the disruptable fertility gene.

In some embodiments, the disruptor nucleotide sequence is conditionally expressible and in illustrative examples of this type, the disruptor transgene comprises an expression-modulating element operably linked to the disruptor nucleotide sequence, wherein the element conditionally inhibits expression of the disruptor nucleotide sequence. For example, the expression-modulating element may inhibit transcription of the disruptor nucleotide sequence under a first condition and disruption of the expression-modulating element may permit or enhance transcription of the disruptor nucleotide sequence under a second condition. In some embodiments, the expression-modulating element comprises an inhibitor nucleotide sequence (e.g., a transcription terminator) that inhibits expression of the disruptor nucleotide sequence and that is operably linked to recombinase recognition sites, wherein the recombinase recognition sites mediate disruption of the inhibitor nucleotide sequence in the presence of a recombinase. In illustrative examples of this type, the first breeding partner comprises an activator transgene that stimulates or enhances expression of the disruptor nucleotide sequence, comprising a coding sequence for the recombinase, operably connected to a promoter.

In some embodiments, the first breeding partner is female and the second breeding partner is male.

Suitably, the first breeding partner is homozygous for the activator transgene and/or the second breeding partner is homozygous for the disruptor transgene.

In a related aspect, the present invention provides a breeding pair of non-human animals, comprising: (1) a first breeding partner comprising a disruptable transgene that comprises a disruptable fertility gene that is operably linked to a promoter and to recombinase recognition sites that mediate disruption of the fertility gene in the presence of a recombinase; and (2) a second breeding partner comprising a disruptor transgene that comprises a disruptor nucleotide sequence encoding a fertility gene disruptor molecule, which is operably connected to a promoter, wherein the fertility gene disruptor molecule comprises the recombinase. In some embodiments, the first breeding partner is female and the second breeding partner is male.

In some embodiments, the first breeding partner is homozygous for the disruptable transgene and/or the second breeding partner is homozygous for the disruptor transgene.

In some embodiments, the breeding pair of non-human animals comprises: (1) a first breeding partner comprising a first disruptable transgene that comprises a disruptable fertility gene operably connected to a promoter and to first recombinase recognition sites, which mediate disruption of the disruptable fertility gene in the presence of a first recombinase, and a first disruptor transgene that comprises a coding sequence for a second recombinase operably linked to a promoter, wherein the second recombinase specifically recognizes second recombinase recognition sites, and (2) a second breeding partner comprising a second disruptable transgene that comprises a disruptable fertility gene operably connected to a promoter and to second recombinase recognition sites, which mediate disruption of the disruptable fertility gene in the presence of the second recombinase, and a second disruptor transgene that comprises a coding sequence for the first recombinase operably linked to a promoter, wherein the first recombinase specifically recognizes the first recombinase recognition sites. Suitably, the first breeding partner is homozygous for the first disruptable and first disruptor transgenes and/or the second breeding partner is homozygous for the second disruptable and second disruptor transgenes.

In another related aspect, the present invention provides a breeding pair of non-human animals, comprising: (1) a first breeding partner comprising a disruptable fertility gene; and (2) a second breeding partner comprising a disruptor transgene that comprises a disruptor nucleotide sequence, which is operably linked to a promoter, and which encodes an inhibitory RNA molecule (e.g., antisense RNA, siRNA, shRNA, etc.) that inhibits expression of the disruptable fertility gene. In some embodiments, the disruptor nucleotide sequence is conditionally expressible and in illustrative examples of this type, the disruptor transgene comprises an expression-modulating element operably linked to the disruptor nucleotide sequence, wherein the element conditionally inhibits expression of the disruptor nucleotide sequence. For example, the expression-modulating element may inhibit transcription of the disruptor nucleotide sequence under a first condition and disruption of the expression-modulating element may permit or enhance transcription of the disruptor nucleotide sequence under a second condition. In some embodiments, the expression-modulating element comprises an inhibitor nucleotide sequence (e.g., a transcription terminator) that inhibits expression of the disruptor nucleotide sequence and that is operably linked to recombinase recognition sites, wherein the recombinase recognition sites mediate disruption of the inhibitor nucleotide sequence in the presence of a recombinase. In illustrative examples of this type, the second breeding partner comprises an activator transgene comprising a coding sequence for the recombinase, operably connected to a promoter. The disruptable fertility gene of the second breeding partner is suitably a wild-type gene. In some embodiments, the first breeding partner is female and the second breeding partner is male.

Thus, in some embodiments, the breeding pair of non-human animals comprises: (1) a first breeding partner comprising a disruptable fertility gene operably connected to a promoter and an activator transgene that comprises a coding sequence for a recombinase operably linked to a promoter; and (2) a second breeding partner comprising a disruptor transgene that comprises a disruptor nucleotide sequence encoding an inhibitory RNA molecule (e.g., antisense RNA, siRNA, shRNA, etc.) that inhibits expression of the disruptable fertility gene, wherein the disruptor nucleotide sequence is operably linked to a promoter and to an expression-modulating element that comprises an inhibitor nucleotide sequence (e.g., a transcription terminator) that inhibits expression of the disruptor nucleotide sequence in the absence of the recombinase and that is operably linked to recombinase recognition sites that mediate disruption of the inhibitor nucleotide sequence in the presence of the recombinase. Suitably, the first breeding partner is homozygous for the activator transgene and/or the second breeding partner is homozygous for the disruptor transgene. In some embodiments, the first breeding partner is female and the second breeding partner is male.

In yet another related aspect, the present invention provides a breeding pair of non-human animals, comprising: (1) a first breeding partner comprising a disruptable fertility gene; and (2) a second breeding partner comprising a disruptor transgene that comprises a disruptor nucleotide sequence, which encodes an antibody that is immuno-interactive with a polypeptide product of the disruptable fertility gene, and which is operably linked to a promoter. In some embodiments, the disruptor nucleotide sequence is conditionally expressible and in illustrative examples of this type, the disruptor transgene comprises an expression-modulating element operably linked to the disruptor nucleotide sequence, wherein the element conditionally inhibits expression of the disruptor nucleotide sequence. For example, the expression-modulating element may inhibit transcription of the disruptor nucleotide sequence under a first condition and disruption of the expression-modulating element may permit or enhance transcription of the disruptor nucleotide sequence under a second condition. In some embodiments, the expression-modulating element comprises an inhibitor nucleotide sequence (e.g., a transcription terminator) that inhibits expression of the disruptor nucleotide sequence and that is operably linked to recombinase recognition sites, wherein the recombinase recognition sites mediate disruption of the inhibitor nucleotide sequence in the presence of a recombinase. In illustrative examples of this type, the first breeding partner comprises an activator transgene comprising a coding sequence for the recombinase, operably connected to a promoter. The disruptable fertility gene of the second breeding partner is suitably a wild-type gene. In some embodiments, the first breeding partner is female and the second breeding partner is male.

Thus, in some embodiments, the breeding pair of non-human animals comprises: (1) a first breeding partner comprising a disruptable fertility gene operably connected to a promoter and an activator transgene that comprises a coding sequence for a recombinase operably linked to a promoter; and (2) a second breeding partner comprising a disruptor transgene that comprises a disruptor nucleotide sequence encoding an antibody that is immuno-interactive with a polypeptide product of the fertility gene, wherein the disruptor nucleotide sequence is operably linked to a promoter and to an expression-modulating element that comprises an inhibitor nucleotide sequence (e.g., a transcription terminator) that inhibits expression of the disruptor nucleotide sequence in the absence of a recombinase and that is operably linked to recombinase recognition sites that mediate disruption of the inhibitor nucleotide sequence in the presence of the recombinase. Suitably, the first breeding partner is homozygous for the activator transgene and/or the second breeding partner is homozygous for the disruptor transgene. In some embodiments, the first breeding partner is female and the second breeding partner is male.

In another aspect, the present invention provides methods for producing a non-human host embryo that comprises a disrupted fertility gene. These methods generally comprise or consist essentially of: (a) mating a first breeding partner of a breeding pair of non-human animals with a second breeding partner of the breeding pair, as broadly described above and elsewhere herein; and (b) producing a pre-implantation non-human embryo from a female member of the breeding pair, which embryo comprises in its germ line a disruption of the fertility gene. In some embodiments, the methods further comprise culturing a non-human host embryo under conditions that allow formation of the pre-implantation non-human host embryo. In some embodiments, the first breeding partner is female and the second breeding partner is male. In some embodiments, the methods further comprise introducing a donor pluripotent cell as described for example above and elsewhere herein into the pre-implantation non-human embryo. Suitably, the pluripotent cell comprises a genetic modification. In specific embodiments, the pluripotent cell is a male pluripotent cell.

In a related aspect, the present invention provides a non-human host embryo resulting from the above methods.

In yet another aspect, the present invention provides methods of producing a chimeric non-human animal. These methods generally comprise or consist essentially of: (1) transplanting a pre-implantation non-human embryo that comprises in its germ line a disruption of a fertility gene as described for example above and elsewhere herein and that further comprises a heterologous pluripotent cell as described for example above and elsewhere herein; and (2) gestating the non-human host embryo of (1) under conditions suitable for development of the embryo, thereby generating a chimeric non-human animal with a disrupted fertility gene and the genetic modification in its germ line. Suitably, the chimeric non-human animal is a male chimeric non-human animal.

In a related aspect, the present invention provides a chimeric non-human animal resulting from these methods.

Still another aspect of the present invention provides methods of producing a non-human animal that comprises a genetic modification in its genome. These methods generally comprise or consist essentially of: (1) transplanting a pre-implantation non-human embryo that comprises in its germ line a disruption of a fertility gene as described for example above and elsewhere herein and that further comprises a heterologous pluripotent cell as described for example above and elsewhere herein; (2) gestating the non-human host embryo of (1) under conditions suitable for development of the embryo, thereby generating a litter comprising chimeric non-human animal with a disrupted fertility gene and the genetic modification in their germ line; (3) breeding a male chimeric non-human animal from the litter with a cognate female non-human animal that comprises in its genome the fertility gene lacking a disruption thereof, to produce a non-human animal that comprises the genetic modification when the male chimeric non-human animal comprises germ cells or gametes derived from the heterologous pluripotent cell.

In a related aspect, the present invention provides a non-human animal comprising a genetic modification, which results from the above methods.

In another aspect, the present invention provides a non-human animal (e.g., surrogate or foster non-human animal) having transplanted therein a preimplantation non-human host embryo as broadly described above and elsewhere herein.

Another aspect of the present invention provides a chimeric non-human animal that is derived from a pre-implantation non-human host embryo as broadly described above and elsewhere herein.

DETAILED DESCRIPTION OF THE INVENTION

1. Definitions

Figure 1:
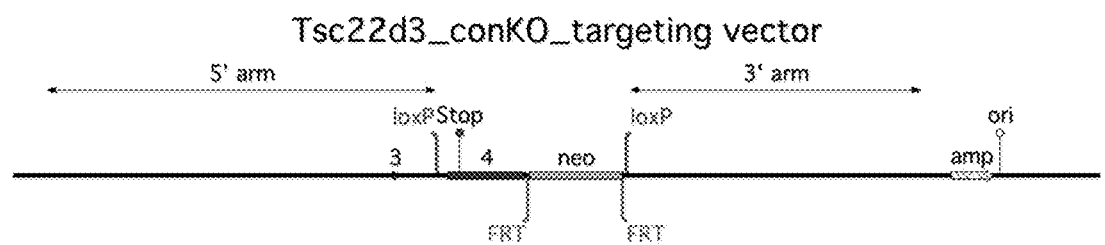
FIG. 1 is a schematic overview of the Tsc22d3 conditional Knockout targeting vector. Blue boxes: exons; neo: neomycin cassette for selection in ES cells; FRT: recognition sequence for flp recombinase mediated neo removal; loxP: recognition sequence for cre recombinase mediated exon deletion; amp: Ampicillin resistance gene; ori: origin of replication.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "a fertility gene" means a single fertility gene or more than one fertility gene.

As used herein, "and/or" refers to and encompasses any and all possible combinations of one or more of the associated listed items, as well as the lack of combinations when interpreted in the alternative (or).

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like.

The term "antisense" refers to a nucleotide sequence whose sequence of nucleotide residues is in reverse 5' to 3' orientation in relation to the sequence of deoxynucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "breeding" as used herein, means the union of male and female gametes so that fertilization occurs. Such a union may be brought about by mating (copulation) or by in vitro or in vivo artificial methods. Such artificial methods include, but are not limited to, artificial insemination, surgical assisted artificial insemination, in vitro fertilization, intracytoplasmic sperm injection, zona drilling, in vitro culture of fertilized oocytes, ovary transfer and ovary splitting.

"Cells", "host cells", "transformed host cells" and the like are terms that not only refer to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "cis-acting sequence" or "cis-regulatory region" or similar term shall be taken to mean any sequence of nucleotides which is derived from an expressible genetic sequence wherein the expression of the genetic sequence is regulated, at least in part, by the sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

By "coding sequence," coding region and the like is meant any nucleic acid sequence that contributes to the code for the polypeptide product of a gene. By contrast, the terms "non-coding sequence" and "non-coding region" refer to any nucleic acid sequence that does not contribute to the code for the polypeptide product of a gene.

The terms "construct" is used herein to refer to a gene or nucleic acid sequence or segment comprising at least two nucleic acid sequences or segments from species which do not combine those sequences or segments under natural conditions, or which sequences or segments are positioned or linked in a manner which does not normally occur in the native genome or nucleome of the untransformed host.

As used herein, "complementary" polynucleotides are those that are capable of hybridizing via base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely or fully complementary to each other, provided that each has at least one region that is substantially complementary to the other. The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules either along the full length of the molecules or along a portion or region of the single stranded molecules. The degree of complementarity between nucleic acid strands has significant effects on the efficiency and strength of hybridization between nucleic acid strands. As used herein, the terms "substantially complementary" or "partially complementary" mean that two nucleic acid sequences are complementary at least at about 50%, 60%, 70%, 80% or 90% of their nucleotides. In some embodiments, the two nucleic acid sequences can be complementary at least at about 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

"Constitutive promoter" refers to a promoter that directs expression of an operably linked transcribable sequence in many or all tissues of an organism.

The term "construct" refers to a recombinant genetic molecule including one or more isolated nucleic acid sequences from different sources. As used herein, the term "expression construct," "recombinant construct" or "recombinant DNA construct" refers to any recombinant nucleic acid molecule such as a plasmid, cosmid, virus, autonomously replicating polynucleotide molecule, phage, or linear or circular single-stranded or double-stranded DNA or RNA nucleic acid molecule, derived from any source, capable of genomic integration or autonomous replication, comprising a nucleic acid molecule where one or more nucleic acid molecules have been operably linked. An "expression construct" generally includes at least a control sequence operably linked to a nucleotide sequence of interest. In this manner, for example, plant promoters in operable connection with the nucleotide sequences to be expressed are provided in expression constructs for expression in a plant, plant part, plant organ and/or plant cell. Methods are known for introducing constructs into a cell in such a manner that a transcribable polynucleotide molecule is transcribed into a functional mRNA molecule that is translated and therefore expressed as a protein product. Constructs may also be made to be capable of expressing inhibitory RNA molecules in order, for example, to inhibit translation of a specific RNA molecule of interest. For the practice of the present invention, conventional compositions and methods for preparing and using constructs and host cells are well known to one skilled in the art, see for example, Molecular Cloning: A Laboratory Manual, 3.sup.rd edition Volumes 1, 2, and 3. J. F. Sambrook, D. W. Russell, and N. Irwin, Cold Spring Harbor Laboratory Press, 2000.

By "control element" or "control sequence" is meant nucleic acid sequences (e.g., DNA) that influence the expression of an operably linked nucleotide sequence (e.g., transcription, RNA processing or stability, or translation of the associated coding sequence). Regulatory sequences include enhancers, promoters, translation leader sequences, introns, and polyadenylation signal sequences. Control elements or control sequences may be located upstream (5' non-coding sequences), within, or downstream (3' non-coding sequences) of a coding sequence. They include natural and synthetic sequences as well as sequences which may be a combination of synthetic and natural sequences. For example, control sequences that are suitable for expression of an operably linked nucleotide sequence in prokaryotic cells include, for example, a promoter, and optionally a cis-acting sequence such as an operator sequence and a ribosome binding site. Control sequences that are suitable for eukaryotic cells include transcriptional control sequences such as promoters, polyadenylation signals, transcriptional enhancers, translational control sequences such as translational enhancers and internal ribosome binding sites (IRES), nucleic acid sequences that modulate RNA stability, as well as targeting sequences that target a product encoded by a transcribed polynucleotide to an intracellular compartment within a cell or to the extracellular environment. Representative control sequences include natural and synthetic sequences as well as sequences which may be a combination of synthetic and natural sequences.

By "corresponds to" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

The terms "culture", "cultured" and "culturing" are used herein interchangeably, to refer to the process by which an embryo or pluripotent cells are grown in vitro.

The terms "disruption" and "disrupted", as applied to a nucleic acid, are used herein interchangeably to refer to any genetic modification that decreases or eliminates expression and/or the functional activity of the nucleic acid or an expression product thereof. For example, disruption of a gene includes within its scope any genetic modification that decreases or eliminates expression of the gene and/or the functional activity of a corresponding gene product (e.g., mRNA and/or protein). Genetic modifications include complete or partial inactivation, suppression, deletion, interruption, blockage, or down-regulation of a nucleic acid (e.g., a gene). Illustrative genetic modifications include, but are not limited to, gene knockout, inactivation, mutation (e.g., insertion, deletion, point, or frameshift mutations that disrupt the expression or activity of the gene product), or use of inhibitory nucleic acids (e.g., inhibitory RNAs such as sense or antisense RNAs, molecules that mediate RNA interference such as siRNA, shRNA, miRNA; etc.), inhibitory polypeptides (e.g., antibodies, polypeptide-binding partners, dominant negative polypeptides, enzymes etc.) or any other molecule that inhibits the activity of the fertility gene or level or functional activity of an expression product of the fertility gene.

"Dominant negative" refers to a gene product that adversely affects, blocks or abrogates the function of a normal, wild-type gene product when co-expressed with the wild type gene product within the same cell even when the cell is heterozygous (wild-type and dominant negative). Expression of the dominant negative mutant generally results in a decrease in normal function of the wild-type gene product.

As used herein an "early stage embryo" encompasses all embryonic development stages that begin upon fertilization of an oocyte (i.e., a fertilized oocyte) and extends through the 2-cell stage, the 4-cell stage, the 8-cell stage, and the morula (the 16 to 32-cell stage embryo). As defined herein, an early stage embryo does not include the blastula stage of development. By "blastula" is meant the embryonic development stage characterized by the development of a hollow ball of cells surrounding a cavity called the blastocoel. One of skill in the art will recognize that the overall organization of the blastula will vary depending on the organism. For instance, a "blastocyst" refers to a cleavage stage mammalian embryo characterized by a hollow ball of cells made of outer trophoblast cells and inner cell mass.

The terms "embryonic stem cell" and ES cell are used interchangeably herein to refer to a cell that can give rise to many differentiated cell types in an embryo or an adult, including the germ cells. ES cells encompass early embryo-derived cultured cells characterized in that such cells can proliferate while maintaining anaplasticity (totipotency). Generally, embryonic stem cells are of a cell line that is established by culturing cells of an inner cell mass that are undifferentiated stem cells, existing inside the blastocyst in an early embryo of an animal, so that the cells keep proliferating while maintaining their undifferentiated state.

As used herein, the term "embryonic germ cell", which is also referred to as an EG cell, refers to a cultured cell derived from a primordial germ cell, which is characterized in that it has ability almost equivalent to that of the above embryonic stem cell. The embryonic germ cells are of a cell line that is established by culturing primordial germ cells obtained from an embryo several days to several weeks after fertilization (for example, in the case of a mouse, an approximately 8.5 days old embryo) so that the cells keep proliferating while maintaining their undifferentiated state.

As used herein, the terms "encode", "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode", "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

As used herein, an "endangered mammal" belongs to a population of mammals which is at risk of becoming extinct because it is either few in numbers, or threatened by changing environmental or predation parameters, such as elephants, large cats and non-human primates, including gray wolf, banded hare wallaby, jaguar, Asian elephant, saiga antelope and northern white rhinoceros (*Ceratotherium simum cottoni*).

The term "endogenous" in the context of a nucleic acid or protein refers to a nucleic acid sequence or segment or to an amino acid sequence or segment that is normally found in a host organism or host cell.

The terms "endogenous gametes" and "endogenous germ cells" as used herein refer to gametes and germ cells "originating or produced from within" a host embryo and exclude gametes and germ cells in the host embryo which are derived from donor pluripotent cells.

The term "expression" with respect to a gene sequence refers to transcription of the gene and, as appropriate, translation of the resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, a "fertility gene" refers to a gene that is involved in producing offspring or in the ability to conceive. Thus, disruption of a fertility gene may diminish, impair or abrogate a non-human animal's ability to conceive or produce offspring, thereby leading to infertility. The resulting infertility can be present in either male or female. Non-limiting examples of infertility include azoospermia; genetic disorders associated with defective spermatogenesis (e.g., Klinefelter's syndrome and gonadal dysgenesis); oligospermia, varicocele, and other sperm disorders relating to impaired sperm function including, but not limited to, low sperm counts, sperm motility, and sperm morphology; and ovulatory dysfunction (e.g., polycystic ovary syndrome (PCOS) or chronic anovulation). As used herein, a fertility gene that is disruptable (e.g., by a disruptor molecule) is referred to as a "disruptable fertility gene".

The terms "flanked by", "flanking" and the like as they apply to relationships between two or more nucleotide sequences in targeting constructs of the invention do not require one of these nucleotide sequences to be located directly adjacent to another nucleotide sequence. For example, three reference nucleotide sequences (A, B and C) may be flanked by recombination target site sequences, or recombination target sites sequences may be flanking those reference sequences, even though reference sequence B is not directly adjacent to these sites. Accordingly, the term "flanked by" is equivalent to being "in between" the recombination sites and the term "flanking" is equivalent to the recombination sites being upstream or downstream of a reference sequence.

"Functional gene" refers to a gene which produces a gene product which carries out a definable function. In specific embodiments, the functional gene is an endogenous gene.

The terms "gamete" and "gametes" are used interchangeably and refer to secondary germ cells, including oocytes, ova, spermatozoa and sperm.

As used herein, the term "gene" refers to a nucleic acid molecule capable of being used to produce mRNA, antisense RNA, siRNA, shRNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions).

The term "genetic modification" refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. The genetic modification includes within its scope knock-in and knock-out genetic changes.

The terms "germ cell", "germ cells" and "germ line" are used interchangeably and refer to cells that give rise to gametes. These terms include primordial germ cells, cells positive for alkaline phosphatase, primary oocytes, oogonia, spermatogonial stem cells, spermatogonia and primary spermatocytes.

The term "heterologous" refers to objects (e.g., nucleic acid molecules, polypeptides, cells, tissues, etc.) that do not originate from within a particular organism, tissue, or cell. For example, a "heterologous cell," including a "heterologous pluripotent cell," refers to a cell that is not normally or naturally found in an organism or tissue of an organism.

The terms "heterologous polynucleotide", "foreign polynucleotide", "exogenous polynucleotide" and the like are used interchangeably herein to describe genetic material that has been or is about to be artificially introduced into a genome of a host organism and that is transmitted to the progeny of that host. The heterologous polynucleotide may include gene sequences found in an organism into which it is introduced or about to be introduced so long as the introduced polynucleotide contains some modification (e.g., a point mutation, the presence of a selectable marker gene, the presence of a loxP site, etc.) relative to the naturally-occurring polynucleotide. A heterologous polynucleotide may comprise a nucleic acid sequence that is capable of being transcribed into RNA and optionally, translated and/or expressed under appropriate conditions. In some embodiments, it is transcribed into a molecule that interferes with transcription or translation (e.g., antisense molecule) or mediates RNA interference (e.g., siRNA or shRNA). In some embodiments, the heterologous polynucleotide comprises a coding sequence for a peptide or polypeptide. In some embodiments, the heterologous polynucleotide comprises a targeting cassette for introducing a genetic modification into a genome.

The terms "heterologous polypeptide", "foreign polypeptide" and "exogenous polypeptide" are used interchangeably to refer to any peptide or polypeptide which is encoded by a "heterologous polynucleotide", "foreign polynucleotide" and "exogenous polynucleotide," as defined above.

The term "host cell" refers to a cell into which a construct or construct of the invention is introduced. Host cells of the invention include, but need not be limited to, bacterial, yeast, animal (including vertebrate animals), insect and plant cells. Host cells can be unicellular, or can be grown in tissue culture as liquid cultures, monolayers or the like. Host cells may also be derived directly or indirectly from tissues or may exist within an organism including animals. In specific embodiments, the host cell is an animal host cell, particularly a vertebrate animal host cell, including mammalian host cells.

Reference herein to "immuno-interactive" includes reference to any interaction, reaction, or other form of association between molecules and in particular where one of the molecules is, or mimics, a component of the immune system.

The term "knock-in" generally refers to a heterologous or foreign polynucleotide that has been inserted into a genome through homologous recombination. The knock-in polynucleotide may be a mutant form of a gene or gene part that replaces the endogenous, wild-type gene or gene part. Such mutations include insertions of heterologous sequences, deletions, point mutations, frameshift mutations and any other mutations that may prevent, disrupt or alter normal gene expression. Thus, a "knock-in" animal, as used herein, refers to a genetically modified animal in which a heterologous or foreign polynucleotide is inserted into the genome of an animal or in which a specific gene or part thereof of an animal's genome is replaced by a foreign gene or DNA sequence. A "conditional knock-in" includes within its scope a heterologous or foreign polynucleotide that has been inserted into a genome through homologous recombination and that elicits an activity (e.g., regulation of transcription or translation, production of a nucleotide sequence including a coding and/or non-coding sequence, etc.) at a designated developmental stage or under particular environmental conditions. A "conditional knock-in vector" is a vector including a heterologous or foreign gene or part thereof that can be inserted into the genome through homologous recombination and that can elicit an activity (e.g., regulation of transcription or translation, production of a nucleotide sequence including a coding and/or non-coding sequence, etc.) at a designated developmental stage or under particular environmental conditions.

By "knock-out" is meant the inactivation or disruption of a gene, which decreases, abrogates or otherwise inhibits the level or functional activity of an expression product of that gene. A "knock-out" animal refers to a genetically modified animal in which a gene is disrupted. A "conditional knock-out" refers to a gene that is disrupted under specific conditions, such as a gene that is disrupted in a tissue-specific or a temporal-specific pattern. A "conditional knock-out vector" is a vector including a gene that can be disrupted under specific conditions.

By "marker gene" is meant a gene that imparts a distinct phenotype to cells expressing the marker gene and thus allows such transformed cells to be distinguished from cells that do not have the marker. A selectable marker gene confers a trait for which one can 'select' based on resistance to a selective agent (e.g., an herbicide, antibiotic, radiation, heat, or other treatment damaging to untransformed cells). A screenable marker gene (or reporter gene) confers a trait that one can identify through observation or testing, i.e., by 'screening' (e.g., β-glucuronidase, luciferase, green fluorescent protein or other activity not present in untransformed cells).

The term, "microRNA" or "miRNAs" refer to small, noncoding RNA molecules that have been found in a diverse array of eukaryotes, including plants. miRNA precursors share a characteristic secondary structure, forming short 'hairpin' RNAs. The term "miRNA" includes processed sequences as well as corresponding long primary transcripts (pri-miRNAs) and processed precursors (pre-miRNAs). Genetic and biochemical studies have indicated that miRNAs are processed to their mature forms by Dicer, an RNAse III family nuclease, and function through RNA-mediated interference (RNAi) and related pathways to regulate the expression of target genes (Hannon, 2002, *Nature* 418, 244-251; Pasquinelli, et al., 2002, *Annu. Rev. Cell. Dev. Biol.* 18, 495-513). miRNAs may be configured to permit experimental manipulation of gene expression in cells as synthetic silencing triggers 'short hairpin RNAs' (shRNAs) (Paddison et al., 2002, *Cancer Cell* 2, 17-23). Silencing by shRNAs involves the RNAi machinery and correlates with the production of small interfering RNAs (siRNAs), which are a signature of RNAi.

As used herein, a "naturally-occurring" nucleic acid molecule refers to a RNA or DNA molecule having a nucleotide sequence that occurs in nature. For example a naturally-occurring nucleic acid molecule can encode a protein that occurs in nature.

The term "non-coding sequence" refers to any nucleic acid sequence that does not contribute to the code for the polypeptide product of a gene.

The term "non-human animal" means an animal excluding human, and is intended to include any vertebrate such as mammals, birds, reptiles, amphibians and fish. Suitable mammals include rodents, non-human primates, equines such as horses, sheep, goats, lagomorphs such as rabbits, dogs, cats, cattle, zoo animals as well as endangered or exotic mammals. In some embodiments, non-human animals are selected from the rodent family including rat and mouse. In specific embodiments, the non-human animal is a mouse.

By "nucleome" is meant the total nucleic acid complement and includes the genome, extrachromosomal nucleic acid molecules and all RNA molecules such as mRNA, heterogenous nuclear RNA (hnRNA), small nuclear RNA (snRNA), small nucleolar RNA (snoRNA), small cytoplasmic RNA (scRNA), ribosomal RNA (rRNA), translational control RNA (tcRNA), transfer RNA (tRNA), eRNA, messenger-RNA-interfering complementary RNA (micRNA) or interference RNA (iRNA), chloroplast or plastid RNA (cpRNA) and mitochondrial RNA (mtRNA).

The terms "operably connected", "operably linked", "in operable linkage", "in operable connection" and the like are used herein to refer to linkage of polynucleotide elements in a functional relationship. A nucleic acid is "operably linked" when it is placed into a functional relationship with another nucleic acid sequence. For instance, a recombinase recognition site is operably connected to a targeting cassette when it is sufficiently in close proximity to facilitate recombination between the targeting cassette and a target site in the host cell genome. In some embodiments, the recombinase recognition site is located no more than 10 kb, 9, kb, 8 kb, 7 kb, 6 kb, 5 kb, 4 kb, 3 kb, 2 kb, 1 kb, 900 bp, 800 bp, 700 bp, 600 bp, 500 bp, 400 bp, 300 bp, 200 bp, 100 bp, 90 bp, 80 bp, 70 bp, 60 bp, 50 bp, 40 bp, 30 bp, 20 bp or 10 bp from the targeting cassette. In other embodiments, "operable connection" and the like refer to the placement of a transcribable sequence under the regulatory control of a promoter, which controls the transcription and optionally translation of the sequence. In the construction of heterologous promoter/transcribable sequence combinations, it is generally desirable to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the desirable positioning of another control element with respect to a heterologous nucleic acid sequence or gene to be placed under its control is defined by the positioning of the element in its natural setting; i.e., the genes from which it is derived. These terms also include within their scope operable linkages or connections between a promoter and a transcribable sequence in which an expression-modulating element is used to inhibit transcription of the transcribable sequence under a first condition and in which disruption of the expression-modulating element is used to permit or enhance transcription of the transcribable sequence under a second condition.

As used herein, the term "post-transcriptional gene silencing" (PTGS) refers to a form of gene silencing in which the inhibitory mechanism occurs after transcription. This can result in either decreased steady-state level of a specific RNA target or inhibition of translation (Tuschl et al., 2001, *ChemBiochem* 2: 239-245). In the literature, the terms RNA interference (RNAi) and posttranscriptional co-suppression are often used to indicate posttranscriptional gene silencing.

The term "pluripotent" refers to the capability of a cell to differentiate into a number of differentiated cell types that are present in an adult organism (e.g., non-human animal). A pluripotent cell is restricted in its differentiation capability in comparison to a totipotent cell. Pluripotent cells include, but are not restricted to, stem cells capable of differentiating into germ cells, such as ES cells, epiblast stem cells (EpiSCs or epi stem cell), embryonic germ (EG) cells and induced pluripotent stem (iPS) cells. The term "pluripotent cell" includes genetically modified pluripotent cells.

The term "polynucleotide" or "nucleic acid" as used herein designates mRNA, RNA, cRNA, cDNA, iRNA, siRNA, shRNA, miRNA or DNA. The term typically refers to oligonucleotides greater than 30 nucleotides in length.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The terms "progeny", "progeny of the transgenic non-human animal" and the like refer to any and all offspring of every generation subsequent to the originally transformed non-human animals.

By "promoter" is meant a region of DNA, which controls at least in part the initiation and level of transcription. Reference herein to a "promoter" is to be taken in its broadest context and includes the transcriptional regulatory sequences of a classical genomic gene, including a TATA box and CCAAT box sequences, as well as additional regulatory elements (i.e., activating sequences, enhancers and silencers) that alter gene expression in response to developmental and/or environmental stimuli, or in a tissue-specific or cell-type-specific manner. A promoter is usually, but not necessarily, positioned upstream or 5' of a transcribable sequence (e.g., a coding sequence or a sequence encoding a functional RNA), the expression of which it regulates. Furthermore, the regulatory elements comprising a promoter are usually positioned within 2 kb of the start site of transcription of the gene. Promoters according to the invention may contain additional specific regulatory elements, located more distal to the start site to further enhance expression in a cell, and/or to alter the timing or inducibility of expression of a structural gene to which it is operably connected. The term "promoter" also includes within its scope inducible, repressible and constitutive promoters as well as minimal promoters. Minimal promoters typically refer to minimal expression control elements that are capable of initiating transcription of a selected DNA sequence to which they are operably linked. In some examples, a minimal promoter is not capable of initiating transcription in the absence of additional regulatory elements (e.g., enhancers or other cis-acting regulatory elements) above basal levels. A minimal promoter frequently consists of a TATA box or TATA-like box. Numerous minimal promoter sequences are known in the literature. For example, minimal promoters may be selected from a wide variety of known sequences, including promoter regions from fos, CMV, SV40 and IL-2, among many others. Illustrative examples are provided which use a minimal CMV promoter or a minimal IL2 gene promoter (−72 to +45 with respect to the start site; Siebenlist, 1986).

As used herein, "rare or endangered species" include but are not limited to any animal listed by any organization as being threatened or endangered, or any animal whose population, or habitat is threatened, or any animal which is desirably breed in captivity. For example, lists of endangered species may be found at U.S. Fish and Wildlife Service, Endangered Species Program or listed in the Endangered Species Act (ESA).

By "recombinase recognition site" (RRS) is meant a nucleic acid site or sequence to which a recombinase binds or otherwise interacts. Such binding or interaction may be direct or indirect.

The term "regulatable promoter" refers to promoters that direct gene expression not constitutively, but in a temporally- and/or spatially-regulated manner, and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in host cells are constantly being discovered. Since in most cases the exact boundaries of regulatory sequences have not been completely defined, nucleic acid fragments of different lengths may have identical promoter activity.

As used herein, the terms "RNA interference" and "RNAi" refer to a sequence-specific process by which a target molecule (e.g., a target gene, protein or RNA) is downregulated via downregulation of expression. Without being bound to a specific mechanism, as currently understood by those of skill in the art, RNAi involves degradation of RNA molecules, e.g., mRNA molecules within a cell, catalyzed by an enzymatic, RNA-induced silencing complex (RISC). RNAi occurs in cells naturally to remove foreign RNAs (e.g., viral RNAs) triggered by dsRNA fragments cleaved from longer dsRNA which direct the degradative mechanism to other RNA sequences having closely homologous sequences. As practiced as a technology, RNAi can be initiated by human intervention to reduce or even silence the expression of target genes using either exogenously synthesized dsRNA or dsRNA transcribed in the cell (e.g., synthesized as a sequence that forms a short hairpin structure).

As used herein, the terms "small interfering RNA" and "short interfering RNA" ("siRNA") refer to a short RNA molecule, generally a double-stranded RNA molecule about 10-50 nucleotides in length (the term "nucleotides" including nucleotide analogs), preferably between about 15-25 nucleotides in length. In most cases, the siRNA is 17, 18, 19, 20, 21, 22, 23, 24, or 25 nucleotides in length. Such siRNA can have overhanging ends (e.g., 3'-overhangs of 1, 2, or 3 nucleotides (or nucleotide analogs). Such siRNA can mediate RNA interference.

As used in connection with the present invention, the term "shRNA" refers to an RNA molecule having a stem-loop structure. The stem-loop structure includes two mutually complementary sequences, where the respective orientations and the degree of complementarity allow base pairing between the two sequences. The mutually complementary sequences are linked by a loop region, the loop resulting from a lack of base pairing between nucleotides (or nucleotide analogs) within the loop region.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, California, USA) using standard defaults as used in the reference manual accompanying the software.

"Similarity" refers to the percentage number of amino acids that are identical or constitute conservative substitutions as defined in Table 1.

TABLE 1

| ORIGINAL RESIDUE | EXEMPLARY SUBSTITUTIONS |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |

TABLE 1-continued

| ORIGINAL RESIDUE | EXEMPLARY SUBSTITUTIONS |
| --- | --- |
| Tyr | Trp, Phe |
| Val | Ile, Leu |

Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology," John Wiley & Sons Inc, 1994-1998, Chapter 15.

The term "site-specific homologous recombination" refers to strand exchange crossover events between nucleic acid sequences substantially similar in nucleotide composition. These crossover events can take place between sequences contained in the targeting construct of the invention and endogenous genomic nucleic acid sequences. In addition, it is possible that more than one site-specific homologous recombination event can occur, which would result in a replacement event in which nucleic acid sequences contained within the targeting construct have replaced specific sequences present within the endogenous genomic sequences.

The term "specifically" as applied to disruption of a gene or to recognition of recombinase recognition sites refers to disruption of that gene or to recognition of those recombinase recognition sites without substantially disruption of another gene or substantial recognition of other recombinase recognition sites. For example, an agent that specifically disrupts a fertility gene is one that exhibits a specificity for that fertility gene of greater than about 2-fold, 5-fold, 10-fold, 20-fold, 50-fold or greater than about 100-fold, 500-fold, 1000-fold with respect to disruption of another fertility gene, or of a gene unrelated to fertility. In another example, an agent that specifically recognizes recognition sites of a specified recombinase is one that exhibits a specificity for those recognition sites of greater than about 2-fold, 5-fold, 10-fold, 20-fold, 50-fold or greater than about 100-fold, 500-fold, 1000-fold with respect to specificity for the recognition sites of another recombinase.

"Stringency" as used herein, refers to the temperature and ionic strength conditions, and presence or absence of certain organic solvents, during hybridization and washing procedures. The higher the stringency, the higher will be the degree of complementarity between immobilized target nucleotide sequences and the labeled probe polynucleotide sequences that remain hybridized to the target after washing.

"Stringent conditions" refers to temperature and ionic conditions under which only nucleotide sequences having a high frequency of complementary bases will hybridize. The stringency required is nucleotide sequence dependent and depends upon the various components present during hybridization and subsequent washes, and the time allowed for these processes. Generally, in order to maximize the hybridization rate, non-stringent hybridization conditions are selected; about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately stringent washing conditions are selected to be about 15 to 30° C. lower than the $T_m$. Highly permissive (low stringency) washing conditions may be as low as 50° C. below the $T_m$, allowing a high level of mismatching between hybridized sequences. Those skilled in the art will recognize that other physical and chemical parameters in the hybridization and wash stages can also be altered to affect the outcome of a detectable hybridization signal from a specific level of sequence identity between target and probe sequences.

The terms "targeting cassette", "targeting construct" and the like refer to a nucleic acid construct that facilitates disruption or insertion of a specific nucleic acid sequence in the genome of an organism or host cell by homologous recombination. Generally, the targeting cassette comprises: (1) at least one homology region or homology arm having a sequence that is substantially identical to or substantially complementary with a sequence present in a host cell endogenous gene locus, and (2) a targeting region which becomes integrated into an host cell endogenous gene locus by homologous recombination between a targeting construct homology region and the endogenous gene locus sequence. A targeting region may comprise a sequence that is substantially homologous to an endogenous gene sequence and/or may comprise in some embodiments a non-homologous sequence, such as a selectable marker (e.g., neo, tk, gpt) or heterologous polynucleotide. The terms "targeting cassette", "targeting construct" and the like do not necessarily indicate that the targeting region comprises a gene which becomes integrated into the host genome, nor does it necessarily indicate that the targeting region comprises a complete structural gene sequence. As used in the art, the terms "targeting cassette", "targeting construct" and the like are synonymous with the term "transgene" as used herein.

The term "totipotent" refers to the capability of a cell to differentiate into all of the cell types of an adult organism (e.g., non-human animal).

The term "transcribable nucleic acid sequence" or "transcribed nucleic acid sequence" excludes the non-transcribed regulatory sequence that drives transcription. Depending on the aspect of the invention, the transcribable sequence may be derived in whole or in part from any source known to the art, including a plant, a fungus, an animal, a bacterial genome or episome, eukaryotic, nuclear or plasmid DNA, cDNA, viral DNA or chemically synthesized DNA. A transcribable sequence may contain one or more modifications in either the coding or the untranslated regions, which could affect the biological activity or the chemical structure of the expression product, the rate of expression or the manner of expression control. Such modifications include, but are not limited to, insertions, deletions and substitutions of one or more nucleotides. The transcribable sequence may contain an uninterrupted coding sequence or it may include one or more introns, bound by the appropriate splice junctions. The transcribable sequence may also encode a fusion protein. In other embodiments, the transcribable sequence comprises non-coding regions only.

"Transfection" means the process during which a nucleic acid molecule (e.g. a plasmid or DNA fragment) is inserted into a eukaryotic cell. Typically, 2-50% of cells take up the plasmid and express the protein product for ~3 days without incorporating the plasmid DNA or DNA fragment into the cell's chromosomes (=transient transfection). A small proportion of these cells will eventually incorporate the plasmid DNA into their chromosomes and permanently express the protein product (=stable transfection).

The term "transgene" is used herein to describe genetic material that has been or is about to be artificially introduced into a genome of a host organism and that is transmitted to the progeny of that host. The transgene will typically comprise a polynucleotide that contains non-coding and/or coding sequences that usually but not necessarily impart or elicit an activity (e.g., regulation of transcription or translation, production of a nucleotide sequence including a coding and/or non-coding sequence, etc.). In some embodiments, the transgene comprises a polynucleotide that is capable of being transcribed into RNA and optionally, translated and/or expressed under appropriate conditions. In some embodiments, it is transcribed into a molecule that interferes with transcription or translation (e.g., antisense molecule) or mediates RNA interference (e.g., siRNA or shRNA). In some embodiments, the transgene comprises a coding sequence for a polypeptide. In some embodiments, the transgene comprises a targeting cassette for introducing a genetic modification into a genome. Any of various methods can be used to introduce a transgene into a non-human animal to produce a transgenic animal. Such techniques are well-known in the art and include, but are not limited to, pronuclear microinjection, viral infection and transformation of embryonic stem cells and iPS cells. Methods for generating transgenic animals that can be used include, but are not limited to, those described in J. P. Sundberg and T. Ichiki, Eds., Genetically Engineered Mice Handbook, CRC Press; 2006; M. H. Hofker and I. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; 2002, ISBN-10: 0879695919; K. Turksen (Ed.), Embryonic stem cells: methods and protocols in Methods Mol. Biol. 2002; 185, Humana Press; Current Protocols in Stem Cell Biology, ISBN: 978047015180; Meyer et al. PNAS USA, vol. 107 (34), 15022-15026.

As used herein, the term "transgenic" or "transformed" with respect to a host cell, host part, host tissue or host means a host cell, host part, host tissue or host animal which comprises a genetic modification, which has been introduced into the nucleome, especially the genome, of a host cell, host part, host tissue or host animal, typically by way of a transgene.

By "vector" is meant a nucleic acid molecule, suitably a DNA molecule derived, for example, from a plasmid, bacteriophage, or plant virus, into which a nucleic acid sequence may be inserted or cloned. A vector typically contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a marker such as an antibiotic resistance gene that can be used for identification of suitable transformants. Examples of such resistance genes are well known to those of skill in the art.

The term "5' non-coding region" is used herein in its broadest context to include all nucleotide sequences which are derived from the upstream region of an expressible gene, other than those sequences which encode amino acid residues which comprise the polypeptide product of the gene, wherein 5' non-coding region confers or activates or otherwise facilitates, at least in part, expression of the gene.

As used herein, the term "5' untranslated region" or "5' UTR" refers to a sequence located 3' of a promoter region and 5' of the downstream coding region. Thus, such a sequence, while transcribed, is upstream (i.e., 5') of the translation initiation codon and therefore is generally not translated into a portion of the polypeptide product.

The term "3' untranslated region" or "3' UTR" refers to a nucleotide sequences downstream (i.e., 3') of a coding sequence. It extends from the first nucleotide after the stop codon of a coding sequence to just before the poly(A) tail of the corresponding transcribed mRNA. The 3' UTR may contain sequences that regulate translation efficiency, mRNA stability, mRNA targeting and/or polyadenylation.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" "variant" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, underscoring or italicizing the name of a gene shall indicate the gene, in contrast to its protein product, which is indicated in the absence of any underscoring or italicizing. For example, "GILZ" shall mean the GILZ gene, whereas "GILZ" shall indicate the protein product of the "GILZ" gene.

Each embodiment described herein is to be applied mutatis mutandis to each and every embodiment unless specifically stated otherwise.

2. Abbreviations

The following abbreviations are used throughout the application:
dpc=days post coitum
ES cell=embryonic stem cell
epi stem cell=epiblast stem cell
EG cell=embryonic germ cell
iPS cell=induced pluripotent stem cell
d=day
h=hour
s=seconds 3. Use of Non-Human Embryos with a Disrupted Fertility Gene for Enhancing Germ Line Transmission of Donor Pluripotent Cells The present invention provides compositions and methods for enhancing germ line transmission of donor pluripotent cells, including ones with genetic modifications. Germ cells originating in non-human host embryos are modified so that at least one gene that contributes to fertility (i.e., a fertility gene) is disrupted. The modified non-human host embryos are then used to "host" introduced donor pluripotent cells that have a functional fertility gene (i.e., a fertility gene that is not disrupted). Implantation and gestation of the resulting non-human host embryo in a surrogate or foster non-human animal produces a litter which usually includes two types of chimeric offspring: those that have endogenous germ cells or gametes with a disrupted fertility gene, which are generally derived from the non-human host embryo, and those that comprise germ cells or gametes with a functional fertility gene, which are generally derived from the donor pluripotent cell. When bred with cognate non-human animals that comprise a functional fertility gene, the chimeric non-human animals that comprise endogenous germ cells or gametes having a disrupted fertility gene will have impaired or inhibited fertility. By contrast, chimeric non-human animals that comprise germ cells or gametes derived from the donor pluripotent cell will have normal or unimpaired fertility, thereby enhancing the production of first litter offspring comprising germ cells or gametes derived from the donor pluripotent cell.

3.1 Fertility Genes

Any suitable fertility gene or combination of fertility genes may be disrupted to provide non-human host embryos as well as derived non-human animals and offspring in accordance with the present invention. Non-limiting examples of fertility genes are listed in Table 2, together with illustrative mutations (which are presented in superscript) and allelic compositions that cause fertility gene disruption and lead to infertility (e.g., male infertility). Also presented in Table 2 are illustrative genetic backgrounds, in which disruption of these fertility genes led to infertility (e.g., male infertility).

TABLE 2

FERTILITY GENES AND ILLUSTRATIVE MUTATIONS LEADING TO INFERTILITY

| Fertility Gene(s) | Allelic Composition (Genetic Background) |
|---|---|
| Abcg5 | Abcg5$^{trac}$/Abcg5$^{trac}$ (A/J-Abcg5$^{trac}$) |
| Acox1 | Acox1$^{tm1Jkr}$/Acox1$^{tm1Jkr}$ (involves: 129P2/OlaHsd * C57BL/6J) |
| Acr Smcp Tnp2 | Acr$^{tm1Wen}$/Acr$^{tm1Wen}$ Smco$^{tm1Wen}$/Smco$^{tm1Wen}$ TnpZ$^{tm1Wen}$/TnpZ$^{tm1Wen}$ (involves: 129/Sv * C57BL/6J * CS-1) |
| Adad1 | Adad1$^{tm1Reb}$/Adad1$^{tm1Reb}$ (129X1/SvJ-Tenr$^{tm1Reb}$) |
| Adad1 | Adad1$^{tm1Reb}$/Adad1$^{tm1Reb}$ (129X1/SvJ * C57BL/6) |
| Adam1a | Adam1a$^{tm1Tba}$/Adam1a$^{tm1Tba}$ (involves: 129S2/SvPas * ICR) |
| Adam3 | Adam3$^{tm1Ihgg}$/Adam3$^{tm1Ihgg}$ (involves: 129S1/Sv * 129X1/SvJ * CD-1) |
| Adam3 | Adam3$^{tm1Pmkf}$/Adam3$^{tm1Pmkf}$ (Not Specified) |
| Adamts2 | Adamts2$^{tm1Prc}$/Adamts2$^{tm1Prc}$ (involves: 129/Sv) |
| Adcy10 | Adcy10$^{tm1Lex}$/Adcy10$^{tm1Lex}$ (involves: 129S5/SvEvBrd * C57BL/6) |
| Adra1b | Adra1b$^{tm1Cta}$/Adra1b$^{tm1Cta}$ (involves: 129 * C57BL/6J) |
| Adrm1 | Adrm1$^{GI(OST128063)Lex}$/Adrm1$^{GI(OST128063)Lex}$ (involves: 129S5/SvEvBrd * C57BL/6J) |
| Aes Runx2 | Aes$^{tm1Grid}$/Aes$^{tm1Grid}$ Runx2$^{tm1Mjo}$/Runx2$^+$ (involves: 129S1/Sv * C57BL/6) |
| Aff4 | Aff4$^{tm1Nosa}$/Aff4$^{tm1Nosa}$ (involves: 129P2/OlaHsd * C57BL/6) |
| Agfg1 | Agfg1$^{tm1Jvd}$/Agfg1$^{tm1Jvd}$ (involves: 129P2/OlaHsd) |
| Agps | Agps$^{bs2}$/Agps$^{bs2}$ (STOCK Agps$^{bs2}$/J) |
| Agtpbp1 | Agtpbp1$^{pcd-3J}$/Agtpbp1$^{pcd-3J}$ (involves: BALB/cByJ) |
| Agtpbp1 | Agtpbp1$^{pcd-5J}$/Agtpbp1$^{pcd-5J}$ (DBA/2J) |
| Agtpbp1 | Agtpbp1$^{pcd-8J}$/Agtpbp1$^{pcd-8J}$ (BALB/cJ-Agtpbp1$^{pcd-8J}$/GrsrJ) |
| Agtpbp1 | Agtpbp1$^{pcd-Bdr}$/Agtpbp1$^{pcd-Bdr}$ (C57BL/6J-Agtpbp1$^{pcd-Bdr}$) |
| Agtpbp1 | Agtpbp1$^{pcd-Tg(Dhfr)1Jwg}$/Agtpbp1$^{pcd-Tg(Dhfr)1Jwg}$ (involves: C57BL/6J * CD-1 * DBA/2J) |
| Agtpbp1 | Agtpbp1$^{pcd}$/Agtpbp1$^{pcd}$ (involves: C57BR/cdJ * CBA) |
| Ak7 | Ak7$^{Gt(OST434404)Lex}$/Ak7$^{Gt(OST434404)Lex}$ (involves: 129S5/SvEvBrd * C57BL/6J) |
| Ak7 | Ak7$^{Tg(tetO-Hmox1)675aml}$/Ak7$^{Tg(tetO-Hmox1)675aml}$ (FVB/N-Ak7$^{Tg(tetO-Hmox1)67Saml}$) |
| Akap4 | Akap4$^{tm1Eddy}$/Y (involves: 129S6/SvEvTac * C57BL/6) |
| Alpl Dnmt3a | Alpl$^{tm1(cre)Nagy}$/Alpl$^+$ Dnmt3a$^{tm3.1Enl}$/Dnmt3a$^{tm3.2Enl}$ (involves: 129S1/Sv * 129S4/SvJae * 129X1/SvJ) |
| Alpl Ehmt2 | Alpl$^{tm1(cre)Nagy}$/Alpl$^+$ Ehmt2$^{tm2.1Yshk}$/Ehmt2$^{tm2.1Yshk}$ (involves: 129S1/Sv * 129X1/SvJ * C57BL/6 * CBA) |
| Amh Amhr2 | Amh$^{tm1Bhr}$/Amh$^{tm1Bhr}$ Amhr2$^{tm1Bhr}$/Amhr2$^{tm1Bhr}$ (Not Specified) |
| Amhr2 | Amhr2$^{tm1Bhr}$/Amhr2$^{tm1Bhr}$ (involves: 129S7/SvEvBrd * C57BL/6) |
| Amhr2 | Amhr2$^{tm1Bhr}$/Amhr2$^{tm1Bhr}$ (involves: 129S7/SvEvBrd) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Amhr2 | Amhr2$^{tm3(cre)Bhr}$/Amhr2$^+$ (involves: 129P2/OlaHsd * 129S/SvEv * C57BL/6) |
| Amhr2 Ar | Amhr2$^{tm3(cre)Bhr}$/Amhr2$^+$ Ar$^{tm1Chc}$/Y (involves: 129S/SvEv * C57BL/6) |
| Amhr2 Ctnnb1 | Amhr2$^{tm3(cre)Bhr}$/Amhr2$^+$ Ctnnb1$^{tm1Mmt}$/Ctnnb1$^+$ (involves: 129X1/SvJ * C57BL/6) |
| Amhr2 Nr5a1 | Amhr2$^{tm3(cre)Bhr}$/Amhr2$^+$ Nr5a1$^{tm1Klp}$/Nr5a1$^{tm2Klp}$ (involves: 129P2/OlaHsd) |
| Amhr2 Smad1 Smad5 | Amhr2$^{tm3(cre)Bhr}$/Amhr2$^+$ Smad1$^{tm2Rob}$/Smad1$^{tm2Rob}$ Smad5$^{tm1Huy}$/Smad5$^{tm1Huy}$ (involves: 129P2/OlaHsd * 129S/SvEv * C57BL/6) |
| Amhr2 Smad1 Smad5 | Amhr2$^{tm3(cre)Bhr}$/Amhr2$^+$ Smad1$^{tm2Rob}$/Smad1$^{tm2Rob}$ Smad5$^{tm1Huy}$/Smad5$^{tm1Huy}$ (involves: 129P2/OlaHsd * 129S/SvEv * 129S7/SvEvBrd * C57BL/6) |
| Apaf1 | Apaf1$^{tm1Her}$/Apaf1$^{tm1Her}$ (involves: 129S6/SvEvTac * C57BL/6J) |
| Ar Plekha5 | Ar$^{tm1Che}$/Y Plekha5$^{Tg(AMH-cre)1Flor}$/0 (involves: 129S/SvEv * C57BL/6 * SJL) |
| Ar Plekha5 | Ar$^{tm1Jcz}$/Y Plekha5$^{Tg(AMH-cre)1Flor}$/0 (involves: 129X1/SvJ * C57BL/6 * SJL) |
| Ar Rnase10 | Ar$^{tm1Verh}$/Y Rnase10$^{tm1(cre)Hhe}$/Rnase10$^+$ (involves: 129S7/SvEvBrd * C57BL/6) |
| Arhgdia Arhgdib | Arhgdia$^{tm1Ytk}$/Arhgdia$^{tm1Ytk}$ (involves: 129S/SvEv * C57BL/6 * DBA) |
| Arhgdia Arhgdib | Arhgdia$^{tm1Ytk}$/Arhgdia$^{tm1Ytk}$ Arhgdib$^{tm1Mlyo}$/Arhgdib$^{tm1Mlyo}$ (involves: 129S/SvEv) |
| Arl | Arl6$^{tm2Ves}$/Arl$^{tm2Ves}$ (involves: 129S1/Sv * 129X1/SvJ * C57BL/6) |
| Asz1 | Asz1$^{tm1Zuk}$/Asz1$^{tm1Zuk}$ (involves: 129 * C57BL/6) |
| Atf4 | Atf4$^{tm1Tow}$/Atf4$^{tm1Tow}$ (involves: 129S1/Sv * 129X1/SvJ * NIH Black Swiss) |
| Atm | Atm$^{tm1Awb}$/Atm$^{tm1Awb}$ (either: 129S6/SvEvTac-Atm$^{tm1Awb}$ or (involves: 129S6/SvEvTac * NIH Black Swiss)) |
| Atm | Atm$^{tm1Bai}$/Atm$^{tm1Bai}$ (involves: 129S4/SvJae) |
| Atm | Atm$^{tm1Fwa}$/Atm$^{tm1Fwa}$ (involves: 129S4/SvJae * C57BL/6) |
| Atm | Atm$^{tm1Led}$/Atm$^{tm1Led}$ (involves: 129S6/SvEvTac * Black Swiss) |
| Atp1a4 | Atp1a4$^{tm1Itl}$/Atp1a4$^{tm1Itl}$ (involves: 129S6/SvEvTac * C57BL/6) |
| Atp2b4 | Atp2b4$^{tm1Ges}$/Atp2b4$^{tm1Ges}$ (involves: 129X1/SvJ * Black Swiss) |
| Atp2b4 | Atp2b4$^{tm1Ges}$/Atp2b4$^{tm1Ges}$ (BKSW.129X1-Atp2b4$^{tm1Ges}$) |
| Atp2b4 | Atp2b4$^{tm1Ksch}$/Atp2b4$^{tm1Ksch}$ (involves: 129P2/OlaHsd * C57BL/6) |
| Atp7a | Atp7a$^{Mo-blo}$/Y (Not Specified) |
| Atp7a | Atp7a$^{Mo-ubr}$/Y (Not Specified) |
| Atxn7 | Atxn7$^{tm1Hzo}$/Atxn7$^+$ (involves: 129S7/SvEvBrd * C57BL/6) |
| Axl Mertk Tyro3 | Axl$^{tm1Grl}$/Axl$^{tm1Grl}$ Mertk$^{tm1Grl}$/Mertk$^{tm1Grl}$ Tyro3$^{tm1Grl}$/Tyro3$^{tm1Grl}$ (involves: 129Sv * 129X1/SvJ * C57BL/6J) |
| B4galnt1 | B4galnt1$^{tm1Rlp}$/B4galnt1$^{tm1Rlp}$ (involves: 129S6/SvEvTac * C57BL/6) |
| B4galnt1 St8sia1 | B4galnt1$^{tm1Rlp}$/B4galnt1$^{tm1Rlp}$ St8sia1$^{tm1Rlp}$/St8sia1$^{tm1Rlp}$ (involves: 129S6/SvEvTac) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Bax | Bax$^{tm1Sjk}$/Bax$^+$ |
| Bcl2l1 | Bcl2l1$^{tm1Mam}$/Bcl2l1$^{tm1Mam}$ |
| | (involves: 129S6/SvEvTac * 129X1/SvJ * C57BL/6) |
| Bax | Bax$^{tm1Sjk}$/Bax$^{tm1Sjk}$ |
| | (involves: 129X1/SvJ) |
| Bax | Bax$^{tm1Sjk}$/Bax$^{tm1Sjk}$ |
| | (B6.129X1-Bax$^{tm1Sjk}$/J) |
| Bax | Bax$^{tm1Sjk}$/Bax$^{tm1Sjk}$ |
| Bcl2l1 | Bcl2l1$^{tm1Mam}$/Bcl2l1$^{tm1Mam}$ |
| | (involves: 129S6/SvEvTac * 129X1/SvJ * C57BL/6) |
| Bax | Bax$^{tm1Sjk}$/Bax$^{tm1Sjk}$ |
| Bcl2l1 | Bcl2l1$^{tm1.1Ast}$/Bcl2l1$^{tm1.1Ast}$ |
| | (B6.129-Bcl2l1$^{tm1.1Ast}$Bax$^{tm1Sjk}$) |
| Bbs1 | Bbs1$^{tm1Ves}$/Bbs1$^{tm1Ves}$ |
| | (involves: 129S1/Sv * 129X1/SvJ) |
| Bbs2 | Bbs2$^{tm1Ves}$/Bbs2$^{tm1Ves}$ |
| | (either: (involves: 129S1/Sv * 129X1/SvJ) or (involves: 129S1/Sv * 129X1/SvJ * C57BL/6J)) |
| Bbs4 | Bbs4$^{tm1Ves}$/Bbs4$^{tm1Ves}$ |
| | (involves: 129S1/Sv * 129X1/SvJ * C57BL/6J) |
| Bcl2l1 | Bcl2l1$^{tm1Mam}$/Bcl2l1$^{tm1Mam}$ |
| | (involves: 129S6/SvEvTac * C57BL/6) |
| Bcl2l2 | Bcl2l2$^{Gt(ROSA)41Sor}$/Bcl2l2$^{Gt(ROSA)41Sor}$ |
| | (involves: 129S5/SvEvBrd) |
| Bcl2l1 | Bcl2l1$^{tm1.1Ast}$/Bcl2l1$^{tm1.1Ast}$ |
| Bik | Bik$^{tm1Ast}$/Bik$^{tm1Ast}$ |
| | (B6.Cg-Bcl2l1$^{tm1.1Ast}$Bik$^{tm1Ast}$) |
| Bgn | Bgn$^{tm1Mfy}$/Y |
| Dcn | Dcn$^{tm1Ioz}$/Dcn$^{tm1Ioz}$ |
| | (involves: 129S1/Sv * 129S4/SvJae * 129X1/SvJ) |
| Bmp5 | Bmp5$^{se}$/Bmp5$^{se}$ |
| | Bmp6$^{tm1Rob}$/Bmp6$^{tm1Rob}$ |
| | (involves: 129S/SvEv) |
| Bmp7 | Bmp7$^{tm1Rob}$/Bmp7$^+$ |
| Bmp8a | Bmp8a$^{tm1Bih}$/Bmp8a$^{tm1Bih}$ |
| | (involves: 129S/SvEv * 129S6/SvEvTac * Black Swiss * C57BL/6) |
| Bmp8b | Bmp8b$^{tm1Bih}$/Bmp8b$^{tm1Bih}$ |
| | (involves: 129/Sv * Black Swiss) |
| Boll | Boll$^{tm1Eyx}$/Boll$^{tm1Eyx}$ |
| | (involves: 129 * C57BL/6) |
| Brca1 | Brca1$^{tm2.1Thl}$/Brca1$^{tm2.1Thl}$ |
| | (involves: 129 * C57BL/6) |
| Brca1 | Brca1$^{tm2Arge}$/Brca1$^{tm2Arge}$ |
| | (129-Brca1$^{tm2Arge}$) |
| Brca1 | Brca1$^{tm2Arge}$/Brca1$^{tm2Arge}$ |
| | (involves: 129/Sv * C57BL/6J * MF1) |
| Brca1 | Brca1$^{tm3.1Thl}$/Brca1$^{tm3.1Thl}$ |
| | (involves: 129 * C57BL/6) |
| Brca2 | Brca2$^{tm1Cam}$/Brca2$^{tm1Cam}$ |
| | (involves: 129S/SvEv * MF1) |
| Brca2 | Brca2$^{tm1Col}$/Brca2$^{tm1Col}$ |
| | (either: (involves: 129S2/SvPas * C57BL/10) or (involves: 129S2/SvPas * C57BL/6 * DBA/2)) |
| Brdt | Brdt$^{tm1Djw}$/Brdt$^{tm1Djw}$ |
| | (involves: 129S/SvEv * C57BL/6J) |
| Brwd1 | Brwd1$^{repro5}$/Brwd1$^{repro5}$ |
| | (involves: C3HeB/FeJ * C57BL/6J) |
| Bsg | Bsg$^{tm1Tmu}$/Bsg$^{tm1Tmu}$ |
| | (involves: 129S2/SvPas * C57BL/6J) |
| Bsg | Bsg$^{tm1Tmu}$/Bsg$^{tm1Tmu}$ |
| | (involves: 129/Sv * 129S2/SvPas) |
| Bub1b | Bub1b$^{tm1Jvd}$/Bub1b$^{tm1Jvd}$ |
| | (involves: 129S6/SvEvTac) |
| Cacnb4 | Cacnb4$^{ln-4Jl}$/Cacnb4$^{n-4J}$ |
| | (C3Fe(SWV)-Cacnb4$^{ln-4Jl}$/GrsrJ) |
| Cacng2 | Cacng2$^{stg}$/Cacng2$^{stg}$ |
| | (B6C3Fe a/a-Cacng2$^{stg}$) |
| Cadm1 | Cadm1$^{tm1.2Brd}$/Cadm1$^{tm1.2Brd}$ |
| | (involves: 129S7/SvEvBrd * C57BL/6J) |
| Cadm1 | Cadm1$^{tm1Momo}$/Cadm1$^{tm1Momo}$ |
| | (involves: 129S/SvEv * C57BL/6J) |
| Cadm1 | Cadm1$^{tm1Mrkm}$/Cadm1$^{tm1Mrkm}$ |
| | (involves: 129S6/SvEvTac * C57BL/6J) |
| Calr3 | Calr3$^{tm1Osb}$/Calr3$^{tm1Osb}$ |
| | (involves: 129S2/SvPas * C57BL/6J) |
| Camk4 | Camk4$^{tm1Arm}$/Camk4$^{tm1Arm}$ |
| | (involves: 129 * C57BL/6J) |
| Capza3 | Capza3$^{repro32}$/Capza3$^{repro32}$ |
| | (involves: C3Heb/FeJ * C57BL/6J) |
| Catsper1 | Catsper1$^{tm1Clph}$/Catsper1$^{tm1Clph}$ |
| | (involves: 129S4/SvJae * C57BL/6J) |
| Catsper2 | Catsper2$^{tm1Gar}$/Catsper2$^{tm1Gar}$ |
| | (involves: 129S6/SvEvTac * C57BL/6J) |
| Catsper3 | Catsper3$^{tm1Clph}$/Catsper3$^{tm1Clph}$ |
| | (involves: 129S4/SvJae) |
| Catsper3 | Catsper3$^{tm1Wyan}$/Catsper3$^{tm1Wyan}$ |
| | (involves: 129S7/SvEvBrd * C57BL/6J) |
| Catsper4 | Catsper4$^{tm1Clph}$/Catsper4$^{tm1Clph}$ |
| | (involves: 129S4/SvJae) |
| Catsper4 | Catsper4$^{tm1Wyan}$/Catsper4$^{tm1Wyan}$ |
| | (involves: 129S7/SvEvBrd * C57BL/6J) |
| Catsperd | Catsperd$^{tm1.1Clph}$/Catsperd$^{tm1.1Clph}$ |
| | (involves: 129S4/SvJae * C57BL/6) |
| Cbx3 | Cbx3$^{tm1Pbs}$/Cbx3$^{tm1Pbs}$ |
| | (involves: 129) |
| Cby1 | Cby1$^{tm1Ktkm}$/Cby1$^{tm1Ktkm}$ |
| | (B6.129-Cby1$^{tm1Ktkm}$) |
| Ccna1 | Ccna1$^{tm1Coll}$/Ccna1$^{tm1Coll}$ |
| | (involves: 129S/SvEv * MF1) |
| Ccna1 | Ccna1$^{tm1Djw}$/Ccna1$^{tm1Djw}$ |
| | (involves: 129S7/SvEvBrd) |
| Ccne2 | Ccne2$^{tm1Pisc}$/Ccne2$^{tm1Pisc}$ |
| | (involves: 129S2/SvPas) |
| Cdk2 | Cdk2$^{tm1Kald}$/Cdk2$^{tm1Kald}$ |
| | (involves: 129S1/Sv * C57BL/6) |
| Cdk4 | Cdk4$^{tm1Kiyo}$/Cdk4$^{tm1Kiyo}$ |
| | (involves: 129S1/Sv) |
| Cdk4 | Cdk4$^{tm1Kiyo}$/Cdk4$^{tm1Kiyo}$ |
| | Lin9$^{tm1Orc}$/Lin9$^{tm1Orc}$ |
| | (involves: 129S1/Sv) |
| Cdk5rap2 | Cdk5rap2$^{Gt(RR6465)Byo}$/Cdk5rap2$^{Gt(RR6465)Byo}$ |
| | (involves: 129P2/OlaHsd * C57BL/6J) |
| Cdk16 | Cdk16$^{tm1.2Stge}$/Cdk16$^{tm1.2Stge}$ |
| | (involves: 129S1/Sv * 129X1/SvJ * BALB/cJ * C57BL/6 * SJL) |
| Cdkn2a | Cdkn2a$^{tm3(cre)Cis}$/Cdkn2a$^+$ |
| | (involves: 129S1/Sv * C57BL/6) |
| Cdkn2c | Cdkn2c$^{tm1Bbd}$/Cdkn2c$^{tm1Bbd}$ |
| Cdkn2d | Cdkn2d$^{tm1Maro}$/Cdkn2d$^{tm1Maro}$ |
| | (involves: 129P2/OlaHsd * 129S1/Sv * C57BL/6) |
| Cdo1 | Cdo1$^{tm1.1Mhst}$/Cdo1$^{tm1.1Mhst}$ |
| | (involves: C57BL/6) |
| Celf1 | Celf1$^{tm1Cba}$/Celf1$^{tm1Cba}$ |
| | (involves: 129S2/SvPas * C57BL/6) |
| Cep290 | Cep290$^{tm1.1Jgg}$/Cep290$^{tm1.1Jgg}$ |
| | (B6.129-Cep290$^{tm1.1Jgg}$) |
| Cga | Cga$^{tm1Sac}$/Cga$^{tm1Sac}$ |
| | (involves: 129S2/SvPas * C57BL/6J) |
| Cib1 | Cib1$^{tm1Prse}$/Cib1$^{tm1Prse}$ |
| | (involves: 129S6/SvEvTac * C57BL/6) |
| Cks2 | Cks2$^{tm1Sir}$/Cks2$^{tm1Sir}$ |
| | (Not Specified) |
| Clcn1 | Clcn1$^{adr}$/Clcn1$^{adr}$ |
| | (A2G) |
| Clcn2 | Clcn2$^{tmiTjj}$/Clcn2$^{tmiTjj}$ |
| | (involves: 129S1/Sv * 129X1/SvJ * C57BL/6) |
| Cldn11 | Cldn11$^{tm1Ral}$/Cldn11$^{tm1Ral}$ |
| | (Not Specified) |
| Cldn11 | Cldn11$^{tm1Sts}$/Cldn11$^{tm1Sts}$ |
| | (involves: 129S4/SvJae * C57BL/6) |
| Clgn | Clgn$^{tm1Osb}$/Clgn$^{tm1Osb}$ |
| | (either: 129 or (involves: 129P2/OlaHsd * C57BL/6J)) |
| Cnot | Cnot7$^{tm1Joe}$/Cnot7$^{tm1Joe}$ |
| | (involves: 129/Sv * C57BL/6) |
| Cnot7 | Cnot7$^{tm1Tno}$/Cnot7$^{tm1Tno}$ |
| | (involves: 129S4/SvJae * C57BL/6J) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Cnpy4 | Cnpy4$^{Tg(Tyr)2356C\text{-}2a1Ove}$/Cnpy4$^{Tg(Tyr)2356C\text{-}2a1Ove}$ (FVB/N-Cnpy4$^{Tg(Tyr)2356C\text{-}2a1Ove}$) |
| Cplx1 | Cplx1$^{tm1Rmnd}$/Cplx1$^{tm1Rmnd}$ (Not Specified) |
| Crem | Crem$^{tm1Gsc}$/Crem$^{tm1Gsc}$ (involves: 129/Sv * C57BL/6) |
| Crem | Crem$^{tm1Saco}$/Crem$^{tm1Saco}$ (involves: 129/Sv * C57BL/6) |
| Crem | Crem$^{tm1Saco}$/Crem$^{tm1Saco}$ (involves: C57BL/6) |
| Crtc1 | Crtc1$^{Gt(XK522)Byg}$/Crtc1$^{Gt(XK522)Byg}$ (involves: 129P2/OlaHsd * C57BL/6) |
| Csnk2a2 | Csnk2a2$^{tm1Ocs}$/Csnk2a2$^{tm1Ocs}$ (involves: 129S6/SvEvTac * C57BL/6) |
| Cstf2t | Cstf2t$^{tm1Coma}$/Cstf2t$^{tm1Coma}$ (involves: 129S/SvEv * C57BL/6) |
| Ctnnb1 | Ctnnb1$^{tm2Kem}$/Ctnnb1$^{tm2Kem}$ Emx1$^{tm1(cre)Yql}$/Emx1$^+$ (B6.129-Emx1$^{tm1(cre)Yql}$Ctnnb1$^{tm2Kem}$) |
| Cul4a | Cul4a$^{tm1.2Pra}$/Cul4a$^{tm1.2Pra}$ (Not Specified) |
| Cxcl16 | Cxcl16/Zymnd15$^{tm1Ifc}$/Cxcl16/Zymnd15$^{tm1Ifc}$ (involves: 129S4/SvJae * C57BL/6) |
| Ccl16 | Cxcl16/Zymnd15$^{tm1Ifc}$/Cxcl16/Zymnd15$^{tm1Ifc}$ (involves: 129S4/SvJae * C57BL/6) |
| Cyp19a1 | Cyp19a1$^{tm1Est}$/Cyp19a1$^{tm1Est}$ (involves: 129S6/SvEvTac * C57BL/6) |
| Cyp19a1 | Cyp19a1$^{tm1Slh}$/Cyp19a1$^{tm1Slh}$ (involves: 129S/SvEv * C57BL/6) |
| D15Ertd621e | D15Ertd621e$^{Tg(Tyr)2261COve}$/D15Ertd621e$^{Tg(Tyr)2261COve}$ (FVB/N-D15Ertd621e$^{Tg(Tyr)2261COve}$) |
| Dab1 | Dab1$^{scm}$/Dab1$^{scm}$ (involves: C3HeB/FeJ * DC/Le) |
| Dazap1 | Dazap1$^{tm1Pyen}$/Dazap1$^{tm1Pyen}$ (involves: 129S6/SvEvTac) |
| Dazl | Dazl$^{tm1Hjc}$/Dazl$^{tm1Hjc}$ (involves: 129P2/OlaHsd * MF1) |
| Dbf | Dbf/Dbf$^+$ (involves: 101/H * C3H/HeH) |
| Ddx4 | Ddx4$^{tm1Tnc}$/Ddx4$^{tm1Tnc}$ (involves: 129P2/OlaHsd * C57BL/6NJcl) |
| Ddx25 | Ddx25$^{tm1Mld}$/Ddx25$^{tm1Mld}$ (involves: 129S4/SvJae) |
| Defb41 | Defb41$^{tm1(cre)Psip}$/Defb41$^+$ |
| Dicer1 | Dicer1$^{tm1Bdh}$/Dicer1$^{tm1Bdh}$ (involves: 129/Sv * C57BL/6N) |
| Derl2 | Derl2$^{tm1.2Hpl}$/Derl2$^{tm1.2Hpl}$ (involves: BALB/cJ) |
| Dgka | Dgka$^{TgTn(sb\text{-}cHS4, Tyr)2320A\text{-}2Ov}$/Dgka$^{TgTn(sb\text{-}cHS4, Tyr)2320A\text{-}2Ov}$ (FVB/N-Dgka$^{TgTn(sb\text{-}cHS4, Tyr)2320A\text{-}2Ov}$e) |
| Dhcr24 | Dhcr24$^{tm1Lex}$/Dhcr24$^{tm1Lex}$ (involves: 129S5/SvEvBrd * C57BL/6) |
| Dhh | Dhh$^{tm1Amc}$/Dhh$^{tm1Amc}$ (involves: 129S1/Sv) |
| Dhh | Dhh$^{tm1Amc}$/Dhh$^{tm1Amc}$ (involves: 129S1/Sv * C57BL/6J) |
| Dhh | Dhh$^{tm1Amc}$/Dhh$^{tm1Amc}$ (involves: 129S1/Sv * C57BL/6J * Swiss Webster) |
| Dicer1 Plekha5 | Dicer1$^{tm1Bdh}$/Dicer1$^{tm1Bdh}$ Plekha5$^{Tg(AMH\text{-}cre)1Flor}$/0 (involves: 129 * C57BL/6 * SJL) |
| Dmc1 | Dmc1$^{Mei11}$/Dmc1$^+$ (involves: 129S4/SvJae * C3Heb/FeJ * C57BL/6J) |
| Dmc1 | Dmc1$^{Mei11}$/Dmc1$^+$ (involves: 129S4/SvJae * C57BL/6J) |
| Dmc1 | Dmc1$^{Mei11}$/Dmc1$^{Mei11}$ (involves: 129S4/SvJae * C57BL/6J) |
| Dmc1 | Dmc1$^{tm1Jcs}$/Dmc1$^{tm1Jcs}$ (involves: 129S4/SvJae * C57BL/6J) |
| Dmc1 | Dmc1$^{tm1Tkon}$/Dmc1$^{tm1Tkon}$ (involves: 129S1/Sv * 129X1/SvJ * C57BL/6J) |
| Dmd | Dmd$^{tm1.1Khan}$/Y (involves: C57BL/6 * CBA) |
| Dmrt1 | Dmrt1$^{tm1.1Zark}$/Dmrt1$^{tm1.1Zark}$ (involves: 129 * C57BL/6) |
| Dmrtc2 | Dmrtc2$^{tm1.2Zark}$/Dmrtc2$^{tm1.2Zark}$ (involves: 129S1/Sv * C57BL/6) |
| Dms | Dms/Dms$^+$ (involves: C57BL/6 * DBA/2) |
| Dnah1 | Dnah1$^{tm1Thgg}$/Dnah1$^{tm1Thgg}$ (involves: 129S1/Sv * 129X1/SvJ * CD-1) |
| Dnd1 | Dnd1$^{Ter}$/Dnd1$^{Ter}$ (129S1/Sv-Kit$^W$Oca2$^P$Tyr$^{c\text{-}ch}$) |
| Dnd1 | Dnd1$^{Ter}$/Dnd1$^{Ter}$ Sfl$^{Gt(XD130)Byo}$/Sfl$^+$ (involves: 129P2/OlaHsd * 129S1/SvImJ * 129T1/Sv) |
| Dnmt3l | Dnmt3l$^{tm1Bes}$/Dnmt3l$^{tm1Bes}$ (involves: 129S6/SvEvTac) |
| Dpcd/Poll | Dpcd/Poll$^{Gt(OST280355)Lex}$/Dpcd/Poll$^{Gt(OST280355)Lex}$ (involves: 129S5/SvEvBrd * C57BL/6Brd-Tyr$^{c\text{-}Brd}$) |
| Dpcd/Poll | Dpcd/Poll$^{tm1Nmt}$/Dpcd/Poll$^{tm1Nmt}$ (involves: 129P2/OlaHsd) |
| Dpy19l2 | Dpy19l2$^{tm1Lex}$/Dpy19l2$^{tm1Lex}$ (B6; 129S5-Dpy19l2$^{tm1Lex}$/Mmucd) |
| Dspd | Dspd/Dspd$^+$ (involves: C3H * C57BL/6) |
| Dync1h1 | Dync1h1$^{Swt}$/Dync1h1$^+$ (involves: 101/H * C3H/HeH) |
| E2f1 | E2f1$^{tm1Meg}$/E2f1$^{tm1Meg}$ |
| E2f3 | E2f3$^{tm2.1Gle}$/E2f3$^{tm2.1Gle}$ (involves: 129S4/SvJae * 129S6/SvEvTac * FVB/N * NIH Black Swiss) |
| Efnb2 | Efnb2$^{tm1Henk}$/Efnb2$^+$ (either: 129 or (involves: 129 * C57BL/6) or (involves: 129 * CD-1)) |
| Egr1 | Egr1$^{tm1Pch}$/Egr1$^{tm1Pch}$ (involves: 129S2/SvPas * C57BL/6J) |
| Egr4 | Egr4$^{tm1Jml}$/Egr4$^{tm1Jml}$ (involves: C57BL/6) |
| Ehd1 | Ehd1$^{tm1.2Haba}$/Ehd1$^{tm1.2Haba}$ (involves: 129P2/OlaHsd * C57BL/6J * FVB/N) |
| Ehd1 | Ehd1$^{tm1.2Haba}$/Ehd1$^{tm1.2Haba}$ (FVB.Cg-Ehd1$^{tm1.2Haba}$) |
| Elf4h | Elf4h$^{Gt(Ex279)Byg}$/Elf4h$^{Gt(Ex279)Byg}$ (involves: 129P2/OlaHsd * C57BL/6) |
| Elk1 | Elk1$^{tm1Nor}$/Y (involves: 129P2/OlaHsd * C57BL/6N) |
| Elovl2 | Elovl2$^{tm1Jaco}$/Elovl2$^{tm1Jaco}$ (involves: 129S1/Sv * 129X1/SvJ * C57BL/6J) |
| Emx1 Numb Numbl | Emx1$^{tm1(cre)Krj}$/Emx1$^+$ Numb$^{tm1Ynj}$/Numb$^{tm1Ynj}$ Numbl/Numbl$^{tm1Wmz}$ (involves: 129S2/SvPas * 129X1/SvJ * CD-1) |
| En1 | En1$^{tm4(an)Alj}$/En1$^{tm4(an)Alj}$ (involves: 129S1/Sv * 129X1/SvJ) |
| Entpd5 | Entpd5$^{tm1Rre}$/Entpd5$^{tm1Rre}$ (involves: 129S5/SvEvBrd * C57BL/6J) |
| Epb4.1l2 | Epb4.1l2$^{Gt(AL0682)Wtsi}$/Epb4.1l2$^{Gt(AL0682)Wtsi}$ (involves: 129P2/OlaHsd * C57BL/6) |
| esgd12d | esgd12d/esgd12d (involves: C3HeB/FeJ * C57BL/6) |
| Espl1 | Espl1$^{tm2Pzg}$/Espl1$^+$ |
| Meox2 | Meox2$^{tm1(cre)Sor}$/Meox2$^+$ (involves: 129S4/SvJaeSor * 129S7/SvEvBrd) |
| Esr1 | Esr1$^{tm1.1Gust}$/Esr1$^{tm1.1Gust}$ (B6.129X1-Esr1$^{tm1.1Gust}$) |
| Esr1 | Esr1$^{tm1.1Mma}$/Esr1$^{tm1.1Mma}$ |
| Esr2 | Esr2$^{tm1Mma}$/Esr2$^{tm1Mma}$ (involves: 129S2/SvPas * C57BL/6 * SJL) |
| Esr1 | Esr1$^{tm1Ksk}$/Esr1$^{tm1Ksk}$ (involves: 129P2/OlaHsd * C57BL/6J) |
| Esr1 | Esr1$^{tm1Ksk}$/Esr1$^{tm1Ksk}$ (involves: 129P2/OlaHsd) |
| Esr1 | Esr1$^{tm1Ksk}$/Esr1$^{tm1Ksk}$ |
| Esr2 | Esr2$^{tm1Unc}$/Esr2$^{tm1Unc}$ (involves: 129P2/OlaHsd) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Esr2 | Esr2$^{tm1.2Pcn}$/Esr2$^{tm1.2Pcn}$ (involves: 129S2/SvPas * C57BL/6 * SJL) |
| Etl4 | Etl4$^{Gt(6ESN)6029Gos}$/Etl4$^{Gt(6ESN)6029Gos}$ |
| Etn2 | Etn2$^{Sc}$/Etn2$^{+}$ (involves: 129/Sv * 129S2/SvPas * C57BL/6 * NMRI) |
| Etv4 | Etv4$^{tm1Hass}$/Etv4$^{tm1Hass}$ (involves: 129S4/SvJae * BALB/c) |
| Etv5 | Etv5$^{tm1Kmm}$/Etv5$^{tm1Kmm}$ (involves: 129S6/SvEvTac) |
| Evx2 | Evx2/Hoxd13$^{tm1Ddu}$/Evx2/Hoxd13$^{tm1Ddu}$ (involves: 129S2/SvPas * C57BL/6) |
| Evx2 | Evx2/Hoxd13$^{tm1Ddu}$/Evx2/Hoxd13$^{tm1Ddu}$ (involves: 129S2/SvPas * C57BL/6) |
| Evx2 | Evx2$^{tm1Ddu}$/Evx2$^{tm1Ddu}$ (involves: 129S2/SvPas * C57BL/6J) |
| Ewsr1 | Ewsr1$^{tm1Sclee}$/Ewsr1$^{tm1Sclee}$ (involves: 129S6/SvEvTac * Black Swiss) |
| Exo1 | Exo1$^{tm1Wed}$/Exo1$^{tm1Wed}$ (involves: 129/Sv * C57BL/6J * SJL) |
| Eya4 | Eya4$^{tm1Jsa}$/Eya4$^{tm1Jsa}$ (involves: 129S6/SvEvTac * CBA/J) |
| Fads2 | Fads2$^{tm1Mma}$/Fads2$^{tm1Mma}$ (involves: 129S6/SvEvTac * C57BL/6J) |
| Fads2 | Fads2$^{tm1Wst}$/Fads2$^{tm1Wst}$ (involves: 129P2/OlaHsd) |
| Fancc | Fancc$^{tm1Mab}$/Fancc$^{tm1Mab}$ (involves: 129S1/Sv * 129X1/SvJ * C57BL/6J) |
| Fancl | Fancl$^{gcd}$/Fancl$^{gcd}$ (involves: C57BL/6J * CBA/J) |
| Fancl | Fancl$^{gcd}$/Fancl$^{tm1Ceb}$ (involves: 129Sv * C57BL/6 * FVB/N) |
| Fancl | Fancl$^{tm1Ceb}$/Fancl$^{tm1Ceb}$ (either: (involves: 129S7/SvEvBrd) or (involves: 129S7/SvEvBrd * FVB/N)) |
| Fgfr3 | Fgfr3$^{tm1J}$/Fgfr3$^{tm1J}$ (CByJ.Cg-Fgfr3$^{tm1J}$/GrsrJ) |
| Fgfr3 | Fgfr3$^{tm5.1Cxd}$/Fgfr3$^{+}$ (involves: 129S6/SvEvTac) |
| Fkbp4 | Fkbp4$^{tm1Dvcs}$/Fkbp4$^{tm1Dvcs}$ (involves: 129X1/SvJ * C57BL/6) |
| Fkbp4 | Fkbp4$^{tm1Dvds}$/Fkbp4$^{tm1Dvds}$ (either: (involves: Cd-1) or (involves: 129X1/SvJ * C57BL/6)) |
| Fkbp6 | Fkbp6$^{tm1Fngr}$/Fkbp6$^{tm1Fngr}$ (involves: 129P2/OlaHsd * C57BL/6) |
| Fmn1 | Fmn1$^{(d-3)}$/Fmn1$^{(d-3)}$ (NOD.Cg Prkdc$^{scid}$/J-Fmn1$^{(d-3)}$/GrsrJ) |
| Fndc3a | Fndc3a$^{Gt(RRP208)Byg}$/Fndc3a$^{sys}$ (involves: 129P2/OlaHsd * C3H * C57BL/6 * FVB/N) |
| Fndc3a | Fndc3a$^{sys}$/Fndc3a$^{sys}$ (involves: C3H * FVB/N) |
| Fndc3a | Fndc3a$^{sys}$/Fndc3a$^{sys}$ (B6.Cg-Fndc3a$^{sys}$) |
| Foxi1 | Foxi1$^{tm1Sven}$/Foxi1$^{tm1Sven}$ (involves: 129S1/Sv * 129X1/SvJ) |
| Foxp3 | Foxp3$^{st}$/Y (involves: STOCK MR) |
| Foxp3 | Foxp3$^{tm2Flv}$/Y (involves: C57BL/6) |
| Fus | Fus$^{tm1(DDIT3)Dron}$/Fus$^{tm1(DDIT3)Dron}$ (involves: 129S6/SvEvTac * CD-1) |
| Fzd4 | Fzd4$^{tm1Nat}$/Fzd4$^{tm1Nat}$ (involves: 129S1/Sv * 129X1/SvJ * C57BL/6) |
| Gal3st1 | Gal3st1$^{tm1Kho}$/Gal3st1$^{tm1Kho}$ (involves: 129P2/OlaHsd) |
| Galnt3 | Galnt3$^{tm1Mjec}$/Galnt3$^{tm1Mjec}$ (involves: 129S/SvEv * C57BL/6J) |
| Gamt | Gamt$^{tm1Isb}$/Gamt$^{tm1Isb}$ (involves: 129S1/Sv * 129X1/SvJ) |
| Gapdhs | Gapdhs$^{tm1Dao}$/Gapdhs$^{tm1Dao}$ (involves: 129S6/SvEvTac * C57BL/6N) |
| Gatm | Gatm$^{tm1.1Isb}$/Gatm$^{tm1.1Isb}$ (B6.129-Gatm$^{tm1.1Isb}$) |
| Gdf7 | Gdf7$^{tm1Kng}$/Gdf7$^{tm1Kng}$ (involves: 129S1/Sv * 129X1/SvJ * C57BL/6J) |
| Ggt1 | Ggt1$^{tm1Zuk}$/Ggt1$^{tm1Zuk}$ (involves: 129S7/SvEvBrd * C57BL/6J) |
| Gja1 Plekha5 | Gja1$^{tm1Kwi}$/Gja1$^{tm1Kwi}$ Plekha5$^{Tg(AMB-cre)1Flor}$/0 (involves: 129P2/OlaHsd * C57BL/6 * SJL) |
| Gja1 | Gja1$^{tm2(Gjb1)Kwi}$/Gja1$^{tm2(Gjb1)Kwi}$ (involves: 129P2/OlaHsd * C57BL/6) |
| Gja1 | Gja1$^{tm3(Gjb5)Kwi}$/Gja1$^{tm3(Gjb5)Kwi}$ (involves: 129P2/OlaHsd * C57BL/6) |
| Gja1 | Gja1$^{tm7(Gjb2)Kwi}$/Gja1$^{tm7(Gjb2)Kwi}$ (involves: 129P2/OlaHsd * C57BL/6 * SJL) |
| Gli2 | Gli2$^{tm3.1(Gli1)Alj}$/Gli2$^{+}$ |
| Gli3 | Gli3$^{Xt-J}$/Gli3$^{+}$ (either: (involves: 129S6/SvEvTac * C3H/HeJ) or (involves: 129S6/SvEvTac * Black Swiss * C3H/HeJ)) |
| Glra1 | Glra1$^{spd}$/Glra1$^{spd}$ (B6C3Fe a/a-Glra1$^{spd}$/J) |
| Gnpat | Gnpat$^{tm1Just}$/Gnpat$^{tm1Just}$ (involves: 129S1/Sv * 129X1/SvJ * C57BL/6) |
| Gnrhr | Gnrhr$^{Gt(181A6)Cmhd}$/Gnrhr$^{Gt(181A6)Cmhd}$ (involves: 129S1/Sv * 129X1/SvJ * C57BL/6J) |
| Golga3 | Golga3$^{Tg(06MGMT)T604Kccri}$/Golga3$^{Tg(06MGMT)T604Kccri}$ (involves: CHC * C57BL/6) |
| Gopc | Gopc$^{tm1.1Tno}$/Gopc$^{tm1.1Tno}$ (involves: 129S4/SvJae * C57BL/6) |
| Gpx4 | Gpx4$^{tm3Marc}$/Gpx4$^{tm3Marc}$ (involves: 129P2/OlaHsd) |
| Grid2 | Grid2$^{ho-SJ}$/Grid2$^{ho-SJ}$ (C57BLKS/J) |
| Grid2 | Grid2$^{ho-Bdr}$/Grid2$^{ho-Bdr}$ (C57BL/6J-Grid2$^{ho-Bdr}$) |
| Grid2 | Grid2$^{ho-cpr}$/Grid2$^{ho-cpr}$ (involves: C57BL/10J * DBA/2J) |
| Grid2 | Grid2$^{ho}$/Grid2$^{ho}$ (C57BLKS/J) |
| Grm1 | Grm1$^{crv4}$/Grm1$^{crv4}$ (BALB/cPas-Grm1$^{crv4}$) |
| Gtsf1 | Gtsf1$^{tm1Miya}$/Gtsf1$^{tm1Miya}$ (involves: 129P2/OlaHsd * C57BL/6) |
| Gusb | Gusb$^{mps}$/Gusb$^{mps}$ (involves: C57BL/6By) |
| Gusb | Gusb$^{mps}$/Gusb$^{mps}$ (B6.C-H2-K$^{bm1}$/ByBir-Gusb$^{mps}$/J) |
| H1fnt | H1fnt$^{tm1Yont}$/H1fnt$^{tm1Yont}$ (involves: 129S1/Sv * C57BL/6) |
| H3f3b | H3f3b$^{tm1.1Psk}$/H3f3b$^{tm1.1Psk}$ (involves: C57BL/6N * FVB/N) |
| H3f3b | H3f3b$^{tm1.2Mnn}$/H3f3b$^{+}$ (involves: 129S1/Sv * 129S1/SvImJ * 129S4/SvJaeSor) |
| Hdlk | Hdlk/Hdlk (STOCK Hdlk/GrsrJ) |
| hem6 | hem6/hem6 (involves: 129P2/OlaHsd * 129S6/SvEvTac * C57BL/6) |
| Herc2 | Herc2$^{J}$/Herc2$^{J}$ (BALB/cJ-Herc2$^{J}$) |
| Herc2 | Herc2$^{jdf2-1R}$/Herc2$^{jdf2-1R}$ (Not Specified) |
| Herc2 | Herc2$^{jdf2-2R}$/Herc2$^{jdf2-2R}$ (Not Specified) |
| Herc2 | Herc2$^{jdf2-3R}$/Herc2$^{jdf2-3R}$ (Not Specified) |
| Herc2 | Herc2$^{jdf2-8R}$/Herc2$^{jdf2-8R}$ (Not Specified) |
| Hfe2 | Hfe2$^{tm1Arbr}$/Hfe2$^{tm1Arbr}$ (involves: 129S4 * 129X1/SvJ) |
| Hfm1 | Hfm1$^{Gt(OST347241)Lex}$/Hfm1$^{Gt(OST347241)Lex}$ (involves: 129S5/SvEvBrd * C57BL/6 * SJL) |
| Hip1 | Hip1$^{tm2.1Tsr}$/Hip1$^{tm2.1Tsr}$ (involves: 129X1/SvJ) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Hist1h1 | Hist1h1a$^{tm1Drab}$/Hist1h1a$^{tm1Drab}$ |
| Smcp | Smcp$^{tm1Wen}$/Smcp$^{tm1Wen}$ |
| Tnp2 | Tnp2$^{tm1Wen}$/Tnp2$^+$ |
|  | (involves: 129 * C57BL/6J) |
| Hist1h1 | Hist1h1a$^{tm1Drab}$/Hist1h1a$^{tm1Drab}$ |
| Smcp | Smcp$^{tm1Wen}$/Smcp$^{tm1Wen}$ |
| Tnp2 | Tnp2$^{tm1Wen}$/Tnp2$^{tm1Wen}$ |
|  | (involves: 129 * C57BL/6J) |
| Hist1h1 | Hist1h1t$^{tm1Drab}$/Hist1h1t$^{tm1Drab}$ |
| Smcp | Smcp$^{tm1Wen}$/Smcp$^{tm1Wen}$ |
| Tnp2 | Tnp2$^{tm1Wen}$/Tnp2$^+$ |
|  | (involves: 129 * C57BL/6J) |
| Hist1h1 | Hist1h1t$^{tm1Drab}$/Hist1h1t$^{tm1Drab}$ |
| Smcp | Smcp$^{tm1Wen}$/Smcp$^{tm1Wen}$ |
| Tnp2 | Tnp2$^{tm1Wen}$/Tnp2$^{tm1Wen}$ |
|  | (involves: 129 * C57BL/6J) |
| Hmga1 | Hmga1$^{tm1Cha}$/Hmga1$^+$ |
|  | (chimera involves: 129S1/Sv * C57BL/6J) |
| Hmga2 | Hmga2$^{Pg}$/Hmga2$^{Pg}$ |
|  | (involves: A/St * C57BL * MacArthur's small stock) |
| Hmga2 | Hmga2$^{tm1Cha}$/Hmga2$^{tm1Cha}$ |
|  | (involves: 129S7/SvEvBrd) |
| Hormad1 | Hormad1$^{tm1.2Atot}$/Hormad1$^{tm1.2Atot}$ |
|  | (involves: 129S1/Sv * 129X1/SvJ * C57BL/6JOlaHsd) |
| Hormad1 | Hormad1$^{tm1Atot}$/Hormad1$^{tm1Atot}$ |
|  | (involves: 129S1/Sv * 129X1/SvJ * C57BL/6JOlaHsd) |
| Hormad1 | Hormad1$^{tm1Rajk}$/Hormad1$^{tm1Rajk}$ |
|  | (involves: 129S7/SvEvBrd * C57BL/6) |
| Hormad2 | Hormad2$^{tm1Atot}$/Hormad2$^{tm1Atot}$ |
|  | (involves: 129S1/Sv * 129X1/SvJ * BALB/c * C57BL/6 * SJL) |
| Hormad2 | Hormad2$^{tm1Atot}$/Hormad2$^{tm1Atot}$ |
|  | (involves: 129S1/Sv * 129X1/SvJ * C57BL/6JOlaHsd) |
| Hormad2 | Hormad2$^{tm1Kura}$/Hormad2$^{tm1Kura}$ |
|  | (either: B6.Cg-Hormad2$^{tm1Kura}$ or (involves: C57BL/6J * C57BL/6NCrlj * CBA/JNCrlj)) |
| Hoxa10 | Hoxa10$^{tm1Pc}$/Hoxa10$^{tm1Pc}$ |
|  | (either: (involves: 129S2/SvPas) or (involves: 129S2/SvPas * C57BL/6)) |
| Hoxa10 | Hoxa10$^{tm1Rilm}$/Hoxa10$^{tm1Rilm}$ |
|  | (either: (involves: 129S4/SvJae) or (involves: 129S4/SvJae * C57BL/6)) |
| Hoxa11 | Hoxa11$^{tm1Dmwe}$/Hoxa11$^+$ |
| Hoxc11 | Hoxc11$^{tm1Mrc}$/Hoxc11$^+$ |
| Hoxd11 | Hoxd11$^{tm1Mrc}$/Hoxd11$^+$ |
|  | (involves: 129S1/Sv * 129S7/SvEvBrd * 129X1/SvJ * C57BL/6) |
| Hoxa11 | Hoxa11$^{tm1Dmwe}$/Hoxa11$^{tm1Dmwe}$ |
|  | (involves: 129S1/Sv * 129X1/SvJ * C57BL/6) |
| Hoxa11 | Hoxa11$^{tm1Mrc}$/Hoxa11$^+$ |
| Hoxc11 | Hoxc11$^{tm1Mrc}$/Hoxc11$^+$ |
| Hoxd11 | Hoxd11$^{tm1Mrc}$/Hoxd11$^+$ |
|  | (involves: 129S7/SvEvBrd) |
| Hoxa11 | Hoxa11$^{tm1Mrc}$/Hoxa11$^+$ |
| Hoxc11 | Hoxc11$^{tm1Mrc}$/Hoxc11$^+$ |
| Hoxd11 | Hoxd11$^{tm1Mrc}$/Hoxd11$^{tm1Mrc}$ |
|  | (involves: 129S7/SvEvBrd) |
| Hoxa11 | Hoxa11$^{tm1Mrc}$/Hoxa11$^+$ |
| Hoxc11 | Hoxc11$^{tm1Mrc}$/Hoxc11$^{tm1Mrc}$ |
| Hoxd11 | Hoxd11$^{tm1Mrc}$/Hoxd11$^+$ |
|  | (involves: 129S7/SvEvBrd) |
| Hoxa11 | Hoxa11$^{tm1Mrc}$/Hoxa11$^{tm1Mrc}$ |
| Hoxc11 | Hoxc11$^{tm1Mrc}$/Hoxc11$^{tm1Mrc}$ |
| Hoxd11 | Hoxd11$^{tm2.1(Hoxd11)Mrc}$/Hoxd11$^{tm2.1(Hoxd11)Mrc}$ |
|  | (involves: BALB/cJ) |
| Hoxa11 | Hoxa11$^{tm1Ssp}$/Hoxa11$^{tm1Ssp}$ |
|  | (involves: 129S2/SvPas * CF1) |
| Hoxa13 | Hoxa13$^{Hd}$/Hoxa13$^{Hd}$ |
|  | (B6C3Fe-a/a Hoxa13$^{Hd}$Mcoln3$^{Va-J}$/J) |
| Hoxd4 | Hoxd4$^{tm1Bhr}$/Hoxd4$^{tm1Bhr}$ |
| Rarg | Rarg$^{tm1Ipc}$/Rarg$^{tm1Ipc}$ |
|  | (involves: 129S2/SvPas * 129S7/SvEvBrd * CD-1) |
| Hoxd9 | Hoxd9$^{tm1Emca}$/Hoxd9$^{tm1Emca}$ |
| Hoxd10 | Hoxd10$^{tm1Emca}$/Hoxd10$^{tm1Emca}$ |
|  | (involves: 129S7/SvEvBrd * C57BL/6) |
| Hoxd11 | Hoxd11$^{tm1Ipc}$/Hoxd11$^{tm1Ipc}$ |
|  | (either: (involves: 129/Sv * 129S2/SvPas) or (involves: 129S2/SvPas * C57BL/6)) |
| Hoxd13 | Hoxd13$^{Dyc}$/Hoxd13$^{Dyc}$ |
|  | (BLAB/c-Hoxd13$^{Dyc}$) |
| Hoxd13 | Hoxd13$^{spdh}$/Hoxd13$^{spdh}$ |
|  | (B6C3Fe a/a-Hodx13$^{spdh}$/J) |
| Hoxd13 | Hoxd13$^{tm1Ddu}$/Hoxd13$^{tm1Ddu}$ |
|  | (either: (involves: 129S2/SvPas * 129/Sv) or (involves: 129S2/SvPas * C57BL/6)) |
| Hsd17b4 | Hsd17b4$^{tm1Baes}$/Hsd17b4$^{tm1Baes}$ |
|  | (involves: 129S1/Sv * 129X1/SvJ) |
| Hsf1 | Hsf1$^{tm1Mlv}$/Hsf1$^{tm1Mlv}$ |
| Hsf2 | Hsf2$^{tm1Mlv}$/Hsf2$^{tm1Mlv}$ |
|  | (involves: 129S2/SvPas * 129X1/SvJ * C57BL/6) |
| Hsp90aa1 | Hsp90aa1$^{Gt(S17-2G1)Sor}$/Hsp90aa1$^{Gt(S17-2G1)Sor}$ |
|  | (involves: 129S4/SvJaeSor) |
| Hsp90aa1 | Hsp90aa1$^{Gt(XE444)Syg}$/Hsp90aa1$^{Gt(XE444)Syg}$ |
|  | (involves: 129P2/OlaHsd * C57BL/6) |
| Hsp90aa1 | Hsp90aa1$^{Tg(Tyr)2396BOve}$/Hsp90aa1$^{Tg(Tyr)2396BOve}$ |
|  | (FVB/N-Hsp90aa1$^{Tg(Tyr)2396BOve}$) |
| Hsp90aa1 | Hsp90aa1$^{tm1.1Udon}$/Hsp90aa1$^{tm1.1Udon}$ |
|  | (involves: C57BL/6 * FVB) |
| Hspa2 | Hspa2$^{tm1Dix}$/Hspa2$^{tm1Dix}$ |
|  | (either: 129S/SvEv or C57BL/6) |
| Hspa4 | Hspa4$^{tm1Imad}$/Hspa4$^{tm1Imad}$ |
|  | (involves: 129S1/Sv * 129X1/SvJ * C57BL/6) |
| Hstx1 | Hstx1$^{PWD/Ph}$/Y |
|  | (involves: C57BL/6J * PWD/Ph) |
| Htt 668Hay | Htt$^{tm1Hay}$/Htt$^{tm1Hay}$ Tg(YAC46)668Hay/0 |
|  | (involves: FVB/N) |
| Htt 2511Hay | Htt$^{tm1Hay}$/Htt$^{tm1Hay}$ Tg(YAC72)2511Hay/0 |
|  | (involves: FVB/N) |
| Hydin | Hydin$^{hy3}$/Hydin$^{hy3}$ |
|  | (involves: CBA) |
| Immp2l | Immp2l$^{Tg(TYR)979Ove}$/Immp2l$^{Tg(TYR)979Ove}$ |
|  | (FVB/N-Immp2l$^{Tg(TYR)979Ove}$) |
| Ing2 | Ing2$^{tm1.1Ccha}$/Ing2$^{tm1.1Ccha}$ |
|  | (involves: 129/Sv * C57BL/6J * FVB/N) |
| Ing2 | Ing2$^{tm1.1Ccha}$/Ing2$^{tm1.1Ccha}$ |
| Trp53 | Trp53$^{tm1.1Brd}$/Trp53$^{tm1.1Brd}$ |
|  | (involves: 129/Sv * 129S7/SvEvBrd * C57BL/6J * FVB/N) |
| Inha | Inha$^{tm1Bay}$/Inha$^{tm1Bay}$ |
|  | (involves: 129S7/SvEvBrd * C57BL/6) |
| Inpp5b | Inpp5b$^{tm1Nbm}$/Inpp5b$^{tm1Nbm}$ |
|  | (either: (involves: 129S6/SvEvTac * C57BL/6) or (involves: 129S6/SvEvTac * NIH Black Swiss)) |
| Inpp5b | Inpp5b$^{tm1Nbm}$/Inpp5b$^{tm1Nbm}$ |
|  | (129S6/SvEvTac) |
| Inpp5b | Inpp5b$^{tm2.1Nbm}$/Inpp5b$^{tm2.1Nbm}$ |
|  | (involves: 129S6/SvEvTac * FVB/N) |
| Insl3 | Insl3$^{tm1Imad}$/Insl3$^{tm1Imad}$ |
|  | (involves: 129/Sv * CD-1) |
| Insl3 | Insl3$^{tm1Par}$/Insl3$^{tm1Par}$ |
|  | (involves: 129/Sv * CD-1) |
| Insl5 | Insl5$^{tm1Imad}$/Insl5$^{tm1Imad}$ |
|  | (129(B6)-Insl5$^{tm1Imad}$) |
| Insl6 | Insl6$^{tm1Imad}$/Insl6$^{tm1Imad}$ |
|  | (involves: 129S1/Sv * 129X1/SvJ * C57BL/6J * CD-1) |
| Ip6k1 | Ip6k1$^{tm1.1Snyd}$/Ip6k1$^{tm1.1Snyd}$ |
|  | (involves: 129X1/SvJ * BALB/c * C57BL/6) |
| Izumo1 | Izumo1$^{tm1Osb}$/Izumo1$^{tm1Osb}$ |
|  | (involves: 129S2/SvPas * C57BL/6) |
| Jam3 | Jam3$^{tm1.2Chav}$/Jam3$^{tm1.2Chav}$ |
|  | (involves: 129 * C57BL/6) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Jam3 | Jam3$^{tm1.2Chav}$/Jam3$^{tm1.2Chav}$ (B6.129-Jam3$^{tm1.2Chav}$) |
| Jam3 | Jam3$^{tm1Rha}$/Jam3$^{tm1Rha}$ (involves: 129P2/OlaHsd * C57BL/6) |
| Jam3 1Maal | Jam3$^{tm1Rha}$/Jam3$^{tm1Rha}$ Tg(Tek-Jam3)1Maal/? (involves: 129P2/OlaHsd * C57BL/6 * C57BL/6J * CBA) |
| Jund | Jund$^{tm1Mya}$/Jund$^{tm1Mya}$ (either: 129S2/SvPas or (involves: 129S2/SvPas * C57BL/6)) |
| Katnal1 | Katnal1$^{1H}$/Katnal1$^{1H}$ (involves: C3H/HeH * C57BL/6J) |
| Katnb1 | Katnb1$^{taily}$/Katnb1$^{taily}$ (involves: C57BL/6 * CBA) |
| Kcnj6 | Kcnj6$^{wv}$/Kcnj6$^{+}$ (involves: C57BL/6J) |
| Kcnj6 | Kcnj6$^{wv}$/Kcnj6$^{wv}$ (involves: C57BL/6 * CBA/CaGnLe) |
| Kcnu1 | Kcnu1$^{tm1.2Clin}$/Kcnu1$^{tm1.2Clin}$ (B6.Cg-Kcnu1$^{tm1.2Clin}$) |
| Kcnu1 | Kcnu1$^{tm1Cmsa}$/Kcnu1$^{tm1Cmsa}$ (Not Specified) |
| Kdm3a | Kdm3a$^{Gt(YHA196)Byg}$/Kdm3a$^{Gt(YHA196)Byg}$ (involves: 129P2/OlaHsd * C57BL/6) |
| Kdm3a | Kdm3a$^{tm1Jxu}$/Kdm3a$^{tm1Jxu}$ (involves: 129S6/SvEvTac * C57BL/6) |
| Khdrbs1 | Khdrbs1$^{tm1Rchd}$/Khdrbs1$^{tm1Rchd}$ (involves: 129S1/Sv * 129X1/SvJ * C57BL/6) |
| Kiss1 | Kiss1$^{tm1Rla}$/Kiss1$^{tm1Rla}$ (involves: 129S1/SvImJ) |
| Kiss1r | Kiss1r$^{tm1.1Lex}$/Kiss1r$^{tm1.1Lex}$ (involves: 129S4/SvJae) |
| Kiss1r | Kiss1r$^{tm1Gsn}$/Kiss1r$^{tm1Gsn}$ (involves: 129P2/OlaHsd) |
| Kiss1r | Kiss1r$^{tm1Rla}$/Kiss1r$^{tm1Rla}$ (involves: 129S1/SvImJ) |
| Kit | Kit$^{Mhdasow3}$/Kit$^{Mhdasow3}$ (C3HeB/FeJ-Kit$^{Mhdasow3}$) |
| Kit | Kit$^{Ssm}$/Kit$^{+}$ (involves: C57BL/10 * Non-inbred) |
| Kit | Kit$^{tm1.1Ssm}$/Kit$^{tm1.1Ssm}$ (involves: 129S1/Sv * BALB/c * C57BL/6J * FVB/N) |
| Kit | Kit$^{tm1Bpr}$/Kit$^{tm1Bpr}$ (either: (involves: 129/Sv) or ((involves: 129/Sv * C57BL/6)) |
| Kit | Kit$^{tm1Hntr}$/Kit$^{tm1Hntr}$ (either: (involves: 129/Sv * C57BL/6 * DBA/2) or (involves: 129S1)) |
| Kit | Kit$^{W-1Bao}$/Kit$^{+}$ (C57BL/6J-Kit$^{W-1Bao}$) |
| Kit | Kit$^{W-39J}$/Kit$^{W-44J}$ (involves: C3H/HeJ * C57BL/6J) |
| Kit | Kit$^{W-44J}$/Kit$^{W-44J}$ (B6.C3-Kit$^{W-44J}$) |
| Kit | Kit$^{W-55J}$/Kit$^{W-55J}$ (C57BL/6J) |
| Kit | Kit$^{W-ei}$/Kit$^{W-ei}$ (C57BL-Kit$^{W-ei}$) |
| Kit | Kit$^{W-pw}$/Kit$^{+}$ (involves: STOCK Prop1$^{df}$Myo5a$^{d}$Bmp5$^{se}$) |
| Kit | Kit$^{W-pw}$/Kit$^{W-v}$ (involves: STOCK Prop1$^{df}$Myo5a$^{d}$Bmp5$^{se}$) |
| Kit | Kit$^{Wads}$/Kit$^{Wads}$ (C57BL/6J-Kit$^{Wads}$) |
| Kitl | Kitl$^{Sl-17H}$/Kitl$^{Sl-17H}$ (C3H/HeH-Kitl$^{Sl-17H}$) |
| Kitl | Kitl$^{Sl-m}$/Kitl$^{Sl-m}$ (C57BL/6) |
| Klhl10 | Klhl10$^{tm1Zuk}$/Klhl10$^{+}$ (chimera involves: 129S7/SvEvBrd * C57BL/6J) |
| Kmt2e | Kmt2e$^{tm1.1Hjf}$/Kmt2e$^{tm1.1Hjf}$ (B6.129P2-Kmte$^{tm1.1Hjf}$) |
| Kmt2e | Kmt2e$^{tm1Apa}$/Kmt2e$^{tm1Apa}$ (129S6/SvEvTac-Kmt2e$^{tm1Apa}$) |
| L1cam | L1cam$^{tm1Sor}$/Y (either: 129S7/SvEvBrd-L1cam$^{tm1Sor}$or (129S7/SvEvBrd * C57BL/6J)F1) |
| Large | Large$^{enr-Tg(MpbReg)36Pop}$/Large$^{enr-Tg(MpbReg)36Pop}$ (involves: C57BL/6J * DBA/2J) |
| Large | Large$^{myd-3J}$/Large$^{myd-3J}$ (STOCK Large$^{myd-3J}$/GrsrJ) |
| Lbr | Lbr$^{Gt(XE569)Byg}$/Lbr$^{Gt(XE569)Byg}$ (involves: 129P2/OlaHsd * C57BL/6Cr) |
| Ldhc | Ldhc$^{tm1Erg}$/Ldhc$^{tm1Erg}$ (involves: 129S6/SvEvTac * C57BL/6N) |
| Lep | Lep$^{ob}$/Lep$^{ob}$ (involves: 129X1/SvJ * C57BL/6) |
| Lep | Lep$^{ob}$/Lep$^{ob}$ (involves: V) |
| Lep | Lep$^{ob}$/Lep$^{ob}$ |
| Npy2r | Npy2r$^{tm1.1Hhz}$/Npy2r$^{tm1.1Hhz}$ (involves: 129X1/SvJ * C57BL/6) |
| Lepr | Lepr$^{db-NCSU}$/Lepr$^{db-NCSU}$ (involves: CD-1) |
| Lepr | Lepr$^{db-Pas}$/Lepr$^{db-Pas}$ (DW/Pas) |
| Lepr | Lepr$^{tm1Yli}$/Lepr$^{tm1Yli}$ (B6.129-Lepr$^{tm1Yli}$) |
| Lepr | Lepr$^{tm2Yli}$/Lepr$^{tm2Yli}$ (B6.129-Lepr$^{tm2Yli}$) |
| Lfng | Lfng$^{tm1Rjo}$/Lfng$^{tm1Rjo}$ (either: (involves: 129S7/SvEvBrd * C57BL/6J) or (involves: 129S7/SvEvBrd * C57BL/6J * FVB/N)) |
| Lfng | Lfng$^{tm1Rjo}$/Lfng$^{tm1Rjo}$ Tg(Lfng-LFNG)1Dlhz/0 (involves: 129S7/SvEvBrd * C57BL/6J * CBA) |
| Lfng 2Dihz | Lfng$^{tm1Rjo}$/Lfng$^{tm1Rjo}$ Tg(Lfng-LFNG)2Dlhz/? (involves: 129S7/SvEvBrd * C57BL/6J * CBA) |
| Lgr4 | Lgr4$^{Gt(pGTOTMpfs)1Wcs}$/Lgr4$^{Gt(pGTOTMpfs)1Wcs}$ (involves: 129P2/OlaHsd * C57BL/6 * CD-1) |
| Lgr4 | Lgr4$^{Gt(pU-21)1Kymm}$/Lgr4$^{Gt(pU-21)1Kymm}$ (CBA.Cg-Lgr4$^{Gt(pU-21)1Kymm}$) |
| Lhb | Lhb$^{tm1Kmr}$/Lhb$^{tm1Kmr}$ (involves: 129S7/SvEvBrd * C57BL/6J) |
| Lhcgr | Lhcgr$^{tm1Cvr}$/Lhcgr$^{tm1Cvr}$ (either: 129X1/SvJ-Lhcgr$^{tm1Cvr}$or (involves: 129X1/SvJ * C57BL/6)) |
| Lhcgr | Lhcgr$^{tm1Hht}$/Lhcgr$^{tm1Hht}$ (involves: 129S7/SvEvBrd * C57BL/6J) |
| Lhx9 | Lhx9$^{tm1Lmgd}$/Lhx9$^{tm1Lmgd}$ (involves: 129S1/Sv * 129X1/SvJ * C57BL/6) |
| Lipe | Lipe$^{tm1Gam}$/Lipe$^{tm1Gam}$ (involves: 129S4/SvJae) |
| Lipe | Lipe$^{tm1Ishi}$/Lipe$^{tm1Ishi}$ (involves: 129S7/SvEvBrd * C57BL/6) |
| Lipe | Lipe$^{tm1Land}$/Lipe$^{tm1Land}$ (involves: 129 * C57BL/6J) |
| Lmtk2 | Lmtk2$^{tm1Tya}$/Lmtk2$^{tm1Tya}$ (involves: 129P2/OlaHsd * C57BL/6) |
| Lmx1a | Lmx1a$^{dr-6J}$/Lmx1a$^{dr-6J}$ (C3H/HeJ) |
| Lnp | Lnp$^{UI}$/Lnp$^{+}$ (involves: 101/H * C3H/HeJ) |
| Lnp | Lnp$^{UI}$/Lnp$^{+}$ (involves: 101/H * C3H/HeJ * C57BL/6J) |
| Lpin1 | Lpin1$^{fld-2J}$/Lpin1$^{fld-2J}$ (C3H/HeJ-Lpin1$^{fld-2J}$/J) |
| Lpin1 | Lpin1$^{fld}$/Lpin1$^{fld}$ (BALB/cByJ-Lpin1$^{fld}$) |
| Lrp8 | Lrp8$^{tm1Her}$/Lrp8$^{tm1Her}$ (involves: 129S6/SvEvTac) |
| Lsr | Lsr$^{tm1Mdar}$/Lsr$^{tm1Mdar}$ (either: (involves: 129P2/OlaHsd) or (involves: 129P2/OlaHsd * C57BL/6) or (involves: 129P2/OlaHsd * MF1)) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| M1ap | M1ap$^{Gt(RRO290)Byg}$/M1ap$^{Gt(RRO290)Byg}$ (involves: 129P2/OlaHsd) |
| Mab21l1 | Mab21l1$^{tm1Nao}$/Mab21l1$^{tm1Nao}$ (involves: C57BL/6) |
| Mad2l2 | Mad2l2$^{tm1Ymu}$/Mad2l2$^{tm1Ymu}$ (involves: 129 * C57BL/6J) |
| Mael | Mael$^{tm1Bort}$/Mael$^{tm1Bort}$ (B6.129S4-Mael$^{tm1Bort}$) |
| Man2a2 | Man2a2$^{tm1Mfu}$/Man2a2$^{tm1Mfu}$ (involves: 129S1/Sv * 129X1/SvJ) |
| Map3k4 | Map3k4$^{tm1Glj}$/Map3k4$^{tm1Glj}$ (involves: 129S6/SvEvTac * C57BL/6) |
| Map7 | Map7$^{Gt(ROSABetageo)1Sor}$/Map7$^{Gt(ROSABetageo)1Sor}$ (either: 129S4/SvJaeSor-Map7$^{Gt(ROSABetageo)1Sor}$ or (involves: 129S4/SvJaeSor * C57BL/6J)) |
| Map7 | Map7$^{Mshi}$/Map7$^{Mshi}$ (BALB/cBy) |
| Mapk8ip2 | Mapk8ip2$^{tm1Rjd}$/Mapk8ip2$^{tm1Rjd}$ (involves: 129X1/SvJ * C57BL/6) |
| Mcm8 | Mcm8$^{tm1.1Geno}$/Mcm8$^{tm1.1Geno}$ (involves: 129S2/SvPas * C57BL/6J) |
| Mcph1 | Mcph1$^{tm1.2Kali}$/Mcph1$^{tm1.2Kali}$ (involves: 129S7/SvEvBrd * C57BL/6J) |
| Mdc1 | Mdc1$^{Gt(OST441263)Lex}$/Mdc1$^{Gt(OST441263)Lex}$ (involves: 129S5/SvEvBrd * C57BL/6) |
| Mecp2 | Mecp2$^{tm1.1Vnar}$/Mecp2$^{tm1.1Vnar}$ (B6N.129-Mecp2$^{tm1.1Vnar}$) |
| Mecp2 | Mecp2$^{tm1.1Vnar}$/Y (involves: 129S1/Sv * 129X1/SvJ * C57BL/6NCrl) |
| Mei1 | Mei1$^{m1Jcs}$/Mei1$^{m1Jcs}$ (involves: 129S1/Sv * C57BL/6J) |
| Meig1 | Meig1$^{tm1.2Zzha}$/Meig1$^{tm1.2Zzha}$ (Not Specified) |
| Meig1 | Meig1$^{tm1Shpl}$/Meig1$^{tm1Shpl}$ (involves: 129S1/Sv * 129X1/SvJ * BALB/c) |
| Mgat2 | Mgat2$^{tm1.1Jxm}$/Mgat2$^{tm1.1Jxm}$ (involves: 129S1/Sv * 129X1/SvJ * ICR) |
| Mhstq1 | Mhstq1$^{M. macedonius}$/Mhstq1$^{M. macedonius}$ (involves: C57BL/6J * M. macedonius) |
| Mhstq2 | Mhstq2$^{M. macedonius}$/Mhstq2$^{M. macedonius}$ (involves: C57BL/6J * M. macedonius) |
| Mir9-3 | Mir9-3$^{tm1Sla}$/Mir9-3$^{tm1Sla}$ (involves: C57BL/6 * CBA) |
| Mitf | Mitf$^{Ml-Crc}$/Mitf$^{Ml-Crc}$ (CBA/CaCrc) |
| Mitf | Mitf$^{ml-enu5}$/Mitf$^{ml-enu5}$ (involves: 102 * C3H/El) |
| Mitf | Mitf$^{ml-Mhdabcc2}$/Mitf$^{ml-Mhdabcc2}$ (C3HeB/FeJ) |
| Mkks | Mkks$^{tm1Vcs}$/Mkks$^{tm1Vcs}$ (either: (involves: 129S1/Sv * 129X1/SvJ) or (involves: 129S1/Sv * 129X1/SvJ * C57BL/6J)) |
| Mlh1 | Mlh1$^{tm1Lisk}$/Mlh1$^{tm1Lisk}$ (involves: 129S7/SvEvBrd) |
| Mlh1 | Mlh1$^{tm1Rak}$/Mlh1$^{tm1Rak}$ (involves: 129SP2/OlaHsd * C57BL/6) |
| Mlh1 | Mlh1$^{tm1Wed}$/Mlh1$^{tm1Wed}$ (involves: 129/Sv * C57BL/6J * SJL) |
| Mlh3 | Mlh1$^{tm1Lpkn}$/Mlh1$^{tm1Lpkn}$ (involves: 129S/SvEv) |
| Mmel1 | Mmel1$^{tm1Ldg}$/Mmel1$^{tm1Ldg}$ (involves: 129S/SvEv * MF1) |
| Mns1 | Mns1$^{tm1Jw}$/Mns1$^{tm1Jw}$ (involves: 129S4/SvJae * C57BL/6) |
| Morc1 | Morc1$^{Tg(Tyr)1Az}$/Morc1$^{Tg(Tyr)1Az}$ (FVB/N) |
| Mov10l1 | Mov10l1$^{tm1.2Eno}$/Mov10l1$^{tm1.2Eno}$ (involves: 129S/SvEv * C57BL/6) |
| Mov10l1 | Mov10l1$^{tm1.2Jw}$/Mov10l1$^{tm1.2Jw}$ (involves: 129S4/SvJae * C57BL/6 * FVB/N) |
| Mpz | Mpz$^{ttr}$/Mpz$^{ttr}$ (B6.Cg-Mpz$^{ttr}$/GrsrJ) |
| Msh4 | Msh4$^{tm1Wed}$/Msh4$^{tm1Wed}$ (involves: 129/Sv * C57BL/6 * SJL) |
| Msh4 | Msh4$^{tm1Wed}$/Msh4$^{tm1Wed}$ |
| Msh5 | Msh5$^{tm1Rak}$/Msh5$^{tm1Rak}$ (involves: 129/Sv * C57BL/6 * SJL) |
| Msh5 | Msh5$^{tm1Htr}$/Msh5$^{tm1Htr}$ (involves: 129P2/OlaHsd * FVB) |
| Msh5 | Msh5$^{tm1Rak}$/Msh5$^{tm1Rak}$ (involves: 129/Sv * C57BL/6J * SJL) |
| Mybl1 | Mybl1$^{repro9}$/Mybl1$^{repro9}$ (involves: C3HeB/FeJ * C57BL/6J) |
| Mybl1 | Mybl1$^{repro9}$/Mybl1$^{tm1Epr}$ (involves: C3HeB/FeJ * C57BL/6J) |
| Mybl1 | Mybl1$^{tm1Epr}$/Mybl1$^{tm1Epr}$ (Not Specified) |
| Myo7a | Myo7a$^{sh1-6J}$/Myo7a$^{sh1-6J}$ (involves: C57BLKS/J) |
| Nanos2 | Nanos2$^{tm1Ysa}$/Nanos2$^{tm1Ysa}$ (involves: 129S1/Sv * 129X1/SvJ * ICR) |
| Nanos3 | Nanos3$^{tm1Ysa}$/Nanos3$^{tm1Ysa}$ (involves: 129S1/Sv * 129X1/SvJ * ICR) |
| Nek1 | Nek1$^{kat-2J}$/Nek1$^{kat-2J}$ (C57BL/6J-Nek1$^{kat-2J}$/J) |
| Nek1 | Nek1$^{kat}$/Nek1$^{kat}$ (involves: C3Heb/FeJLe * RBF/Dn) |
| Neurl1a | Neurl1a$^{tm1Led}$/Neurl1a$^{tm1Led}$ (involves: 129S6/SvEvTac) |
| Nfia | Nfia$^{tm1Rmg}$/Nfia$^{tm1Rmg}$ (involves: 129P2/OlaHsd * Black Swiss) |
| Nhlh2 | Nhlh2$^{tm1Irk}$/Nhlh2$^{tm1Irk}$ (involves: 129S4/SvJae * C57BL/6) |
| Nos1 | Nos1$^{tm2Plh}$/Nos1$^{tm2Plh}$ (Not Specified) |
| Notch3 | Notch3$^{hpbk}$/Notch3$^{hpbk}$ (C57BL/6J-Notch3$^{hpbk}$/GrsrJ) |
| Npc1 | Npc1$^{m1N}$/Npc1$^{m1N}$ (involves: BALB/c) |
| Npepps | Npepps$^{goku}$/Npepps$^{goku}$ (involves: 129P2/OlaHsd * BALB/cA) |
| Nphp1 | Nphp1$^{tm1.1Hung}$/Nphp1$^{tm1.1Hung}$ (B6.Cg-Nphp1$^{tm1.1Hung}$) |
| Nphp4 | Nphp4$^{nmf192}$/Nphp4$^{nmf192}$ (involves: C57BL/6J) |
| Nr0b1 | Nr0b1$^{tm1.1Lja}$/Y (involves: 129S1/Sv * 129X1/SvJ) |
| Nr5a1 | Nr5a1$^{tm1.1Hain}$/Nr5a1$^{tm1.1Hain}$ (Not Specified) |
| Nr5a1 3Sac | Nr5a1$^{tm2.1klp}$/Nr5a1$^{tm2.1klp}$ Tg(Cga-cre)3Sac/0 (involves: 129P2/OlaHsd * C57BL/6J * SJL) |
| Nsun2 | Nsun2$^{Gt(D014D11)Wrst}$/Nsun2$^{Gt(D014D11)Wrst}$ (involves: 129S2/SvPas * C57BL/6J * CBA) |
| Nsun2 | Nsun2$^{tm1a(EUCOMM)Wtsi}$/Nsun2$^{tm1a(EUCOMM)Wtsi}$ (involves: C57BL/6N) |
| Nup210l | Nup210l$^{Tg(Gt(ROSA)26Sor-EGFP)130910Eps}$/Nup210l$^{Tg(Gt(ROSA)26Sor-EGFP)130910Eps}$ FVB/NTac-Nup210l$^{Tg(Gt(ROSA)26Sor-EGFP)130910Eps}$/Mmmh) |
| Nxf2 | Nxf2$^{tm1.2Jw}$/Y (involves: 129S2/Sv * 129S4/SvJae * 129X1/SvJ * C57BL/6) |
| Nxf2 | Nxf2$^{tm1.2Jw}$/Y (B6.Cg-Nxf2$^{tm1.2Jw}$) |
| Nxph1 | Nxph1$^{tm1Sud}$/Nxph1$^{tm1Sud}$ (129S6/SvEvTac) |
| Oaz3 | Oaz3$^{tm1Htan}$/Oaz3$^{tm1Htan}$ (involves: 129S1/Sv * C57BL/6) |
| Oca2 | Oca2$^{p-6H}$/Oca2$^{p-6H}$ (involves: 101/H * C3H/HeH) |
| Oca2 | Oca2$^{p-12DTR}$/Oca2$^{p-12DTR}$ (involves: 101/Rl * C3H/Rl) |
| Oca2 | Oca2$^{p-103G}$/Oca2$^{p-103G}$ (involves: 101/Rl * C3H/Rl) |
| Oca2 | Oca2$^{p-s}$/Oca2$^{p-s}$ (Not Specified) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Ocln | Ocln$^{tm1StS}$/Ocln$^{tm1StS}$ (involves: 129S4/SvJae * C57BL/6) |
| Ocln | Ocln$^{tm2StS}$/Ocln$^{tm2StS}$ (involves: 129S4/SvJae * C57BL/6) |
| Odf1 | Odf1$^{tm1Shf}$/Odf1$^{tm1Shf}$ (involves: 129S1/Sv * 129X1/SvJ * C57BL/6J) |
| Odf2 | Odf2$^{Gt(XL169)Byg}$/Odf2$^+$ (involves: 129P2/OlaHsd * C57BL/6) |
| Odf2 | Odf2$^{tm1.2Sats}$/Odf2$^+$ (involves: C57BL/6 * C57BL/6J) |
| P2rx1 | P2rx1$^{tm1Chn}$/P2rx1$^{tm1Chn}$ (involves: 129P2/OlaHsd * MF1) |
| Pafah1b1 | Pafah1b1$^{Gt(IRESBetageo)1Hha}$/Pafah1b1$^{Gt(IRESBetageo)1Hha}$ (involves: 129/Sv * NMRI) |
| Pafah1b2 | Pafah1b2$^{Gt(Betageo)1Cla}$/Pafah1b2$^{Gt(Betageo)1Cla}$ (involves: 129S6/SvEvTac) |
| Pafah1b2 | Pafah1b2$^{Gt(Betageo)1Cla}$/Pafah1b2$^{Gt(Betageo)1Cla}$ (involves: 129S6/SvEvTac) |
| Pafah1b3 | Pafah1b3$^{tm1Cla}$/Pafah1b3$^{tm1Cla}$ (involves: 129S6/SvEvTac) |
| Pafah1b2 | Pafah1b2$^{tm1Aral}$/Pafah1b2$^{tm1Aral}$ |
| Pafah1b3 | Pafah1b3$^{tm1Aral}$/Pafah1b3$^{tm1Aral}$ (involves: 129X1/SvJ * C57BL/6N) |
| Paip2 | Paip2$^{tm1.2Nso}$/Paip2$^{tm1.2Nso}$ (B6.129-Paip2$^{tm1.2Nso}$) |
| Paip2 | Paip2$^{tm1.2Nso}$/Paip2$^{tm1.2Nso}$ |
| Paip2b | Paip2b$^{tm1.2Nso}$/Paip2b$^{tm1.2Nso}$ (B6.129-Paip2b$^{tm1.2Nso}$Paip2$^{tm1.2Nso}$) |
| Pank2 | Pank2$^{tm1.1Suja}$/Pank2$^{tm1.1Suja}$ (involves: 129S/SvEv * C57BL/6J * FVB/N) |
| Pank2 | Pank2$^{tm1Jgt}$/Pank2$^{tm1Jgt}$ (involves: 129X1/SvJ * C57BL/6J) |
| Papolb | Papolb$^{tm1Tba}$/Papolb$^{tm1Tba}$ (involves: 129S2/SvPas * C57BL/6) |
| Patz1 | Patz1$^{tm1Pchl}$/Patz1$^{tm1Pchl}$ (Not Specified) |
| Pax8 | Pax8$^{tm1Pgr}$/Pax8$^{tm1Pgr}$ (either: (involves: 129S1/Sv * 129X1/SvJ) or (involves: 129S1/Sv * 129X1/SvJ * C57BL/6)) |
| Pdgfra Plekha1 | Pdgfra$^{tm1Sor}$/Pdgfra$^+$ Plekha1$^{Gt(ROSA)82Sor}$/Plekha1$^{Gt(ROSA)82Sor}$ (either: (involves: 129S4/SvJaeSor) or (involves: 129S4/SvJaeSor * C57BL/6)) |
| Pdgfra Sgpl1 | Pdgfra$^{tm1Sor}$/Pdgfra$^+$ Sgpl1$^{Gt(ROSA)78Sor}$/Sgpl1$^{Gt(ROSA)78Sor}$ (either: (involves: 129S4/SvJaeSor) or (involves: 129S4/SvJaeSor * C57BL/6)) |
| Pdgfrb Plekha1 | Pdgfrb$^{tm1Sor}$/Pdgfrb$^+$ Plekha1$^{Gt(ROSA)82Sor}$/Plekha1$^{Gt(ROSA)82Sor}$ (either: (involves: 129S4/SvJaeSor * 129S7/SvEvBrd) or (involves: 129S4/SvJaeSor * 129S7/SvEvBrd * C57BL/6)) |
| Pdgfrb Sgpl1 | Pdgfrb$^{tm1Sor}$/Pdgfrb$^+$ Sgpl1$^{Gt(ROSA)78Sor}$/Sgpl1$^{Gt(ROSA)78Sor}$ (either: (involves: 129S4/SvJaeSor * 129S7/SvEvBrd) or (involves: 129S4/SvJaeSor * 129S7/SvEvBrd * C57BL/6)) |
| Pdilt | Pdilt$^{tm1Osb}$/Pdilt$^{tm1Osb}$ (involves: 129S2/SvPas) |
| Pex5 | Pex5$^{tm1Pec}$/Pex5$^{tm1Pec}$ |
| Plekha5 | Plekha5$^{Tg(AMH-cre)1Flor}$/0 (involves: 129S1/Sv * 129X1/SvJ) |
| Pfdn5 | Pfdn5$^{nmf5a}$/Pfdn5$^{nmf5a}$ (C57BL/6-Pfdn5$^{nmf5a}$) |
| Pgk2 | Pgk2$^{tm1Dao}$/Pgk2$^{tm1Dao}$ (involves: 129S6/SvEvTac * C57BL/6NCrl) |
| Pgm3 | Pgm3$^{Gt(W037808)Wrst}$/Pgm3$^{mld1}$ (involves: 129S1/Sv * C57BL/6) |
| Pgm3 | Pgm3$^{mld1}$/Pgm3$^{mld1}$ (C57BL/6-Pgm3$^{mld1}$) |
| Pi4k2a | Pi4k2a$^{Gt(AK0094)Wtsi}$/Pi4k2a$^{Gt(AK0094)Wtsi}$ (involves: 129P2/OlaHsd * BALB/c) |
| Pick1 | Pick1$^{tm1Rlh}$/Pick1$^{tm1Rlh}$ (involves: 129S1/Sv * 129X1/SvJ) |
| Pifo | Pifo$^{tm1.1Helf}$/Pifo$^+$ (chimera involves: 129S6/SvEvTac * C57BL/6J) |
| Pip5k1a | Pip5k1a$^{tm1.1Tba}$/Pip5k1a$^{tm1.1Tba}$ |
| Pip5k1b | Pip5k1b$^{tm1Tssk}$/Pip5k1b$^{tm1Tssk}$ (involves: 129P2/OlaHsd) |
| Piwil1 | Piwil1$^{tm1.1Embrp}$/Piwil1$^+$ (involves: 129S4/SvJaeSor * C57BL/6) |
| Piwil1 | Piwil1$^{tm1.1Embrp}$/Piwil1$^{tm1.1Embrp}$ (involves: 129S4/SvJaeSor * BALB/cJ * C57BL/6) |
| Piwil1 | Piwil1$^{tm1.2Embrp}$/Piwil1$^{tm1.2Embrp}$ (involves: 129S4/SvJaeSor * BALB/cJ * C57BL/6) |
| Piwil1 | Piwil1$^{tm1Hfl}$/Piwil1$^{tm1Hfl}$ (involves: 129S1/Sv * 129X1/SvJ * C57BL/6J) |
| Piwil2 | Piwil2$^{tm1.1Doca}$/Piwil2$^{tm1.1Doca}$ (involves: 129P2/OlaHsd * 129S4/SvJaeSor * C57BL/6J) |
| Piwil2 | Piwil2$^{tm1Nkn}$/Piwil2$^{tm1Nkn}$ (involves: 129S2/SvPas * C57BL/6) |
| Plcd4 | Plcd4$^{tm1Kfu}$/Plcd4$^{tm1Kfu}$ (involves: 129X1/SvJ * C57BL/6J) |
| Pld6 | Pld6$^{tm1.1Hsas}$/Pld6$^{tm1.1Hsas}$ (involves: 129S1/Sv * 129X1/SvJ * C57BL/6J) |
| Pld6 | Pld6$^{tm1.1Mafr}$/Pld6$^{tm1.1Mafr}$ (involves: C57BL/6) |
| Plekha1 | Plekha1$^{Gt(ROSA)82Sor}$/Plekha1$^{Gt(ROSA)82Sor}$ (either: (involves: 129S4/SvJaeSor) or (involves: 129S4/SvJaeSor * C57BL/6)) |
| Plekha5 | Plekha5$^{Tg(AMH-cre)1Flor}$/0 Wt1$^{tm1Jae}$/Wt1$^{tm1Jae}$ (involves: 129S4/SvJae * 129S7/SvEvBrd * C57BL/6 * SJL) |
| Plin2 | Plin2$^{Gt(OST170322)Lex}$/Plin2$^{Gt(OST170322)Lex}$ (involves: 129S5/SvEvBrd * C57BL/6J) |
| Pmis2 | Pmis2$^{tm1Osb}$/Pmis2$^{tm1Osb}$ (involves: 129 * C57BL/6) |
| Pms2 | Pms2$^{tm1Llsk}$/Pms2$^{tm1Llsk}$ (involves: 129S2/SvPas * C57BL/6) |
| Pms2 | Pms2$^{tm1Llsk}$/Pms2$^{tm1Llsk}$ (involves: 129S2/SvPas) |
| Pomgnt1 | Pomgnt1$^{Gt(OST179231)Lex}$/Pomgnt1$^{Gt(OST179231)Lex}$ (involves: 129S5/SvEvBrd * C57BL/6J) |
| Pomk | Pomk$^{Gt(OST243203)Lex}$/Pomk$^{Gt(OST243203)Lex}$ (involves: 129S5/SvEvBrd * C57BL/6J) |
| Ppm1d | Ppm1d$^{tm1Lad}$/Ppm1d$^{tm1Lad}$ (involves: 129S7/SvEvBrd * C57BL/6) |
| Ppp1cc | Ppp1cc$^{tm1Var}$/Ppp1cc$^{tm1Var}$ (involves: 129S1/Sv * 129X1/SvJ * CD-1) |
| Prdm9 | Prdm9$^{repro7}$/Prdm9$^{repro7}$ (B6; C3Fe-Prdm9$^{repro7}$/J) |
| Prdm9 | Prdm9$^{tm1Ymat}$/Prdm9$^{tm1Ymat}$ (involves: 129P2/OlaHsd * C57BL/6) |
| Prdm14 | Prdm14$^{tm1Sait}$/Prdm14$^{tm1Sait}$ (B6.129P2-Prdm14$^{tm1Sait}$) |
| Prkaca | Prkaca$^{tm1Gsm}$/Prkaca$^{tm1Gsm}$ (involves: 129X1/SvJ * C57BL/6) |
| Prkaca | Prkaca$^{tm2Gsm}$/Prkaca$^{tm2Gsm}$ (involves: 129X1/SvJ * C57BL/6) |
| Prkdc | Prkdc$^{scid}$/Prkdc$^{scid}$ Tgfb1$^{tm1Doe}$/Tgfb1$^{tm1Doe}$ (involves: 129 * C3H * CF-1) |
| Prlr | Prlr$^{tm1Cnp}$/Prlr$^{tm1Cnp}$ (either: (involves: 129/Sv * 129P2/OlaHsd) or (involves: 129P2/OlaHsd * C57BL/6)) |
| Prlr | Prlr$^{tm1Cnp}$/Prlr$^{tm1Cnp}$ (involves: 129P2/OlaHsd * 129S2/SvPas) |
| Prnd | Prnd$^{tm1Aag}$/Prnd$^{tm1Aag}$ (involves: 129P2/OlaHsd) |
| Prnd | Prnd$^{tm1Ovm}$/Prnd$^{tm1Ovm}$ (129P2/OlaHsd) |
| Prnp | Prnp/Prnd$^{tm1Aag}$/Prnp/Prnd$^{tm1Aag}$ (Not Specified) |
| Prnp | Prnp/Prnd$^{tm1Aag}$/Prnp/Prnd$^{tm1Aag}$ (Not Specified) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Prnp | Prnp/Prnd$^{tm1Dwm}$/Prnp/Prnd$^{tm1Dwm}$ (129P2/OlaHsd) |
| Prnp | Prnp/Prnd$^{tm1Dwm}$/Prnp/Prnd$^{tm1Dwm}$ (129P2/OlaHsd) |
| Prop1 | Prop1$^{df}$/Prop1$^{df}$ (STOCK Prop1$^{df}$) |
| Ptch1 | Ptch1$^{mes}$/Ptch1$^{mes}$ (B6C3Fe a/a-Ptch1$^{mes}$) |
| Ptdss2 | Ptdss2$^{Gt(KST314)Byg}$/Ptdss2$^{Gt(KST314)Byg}$ (involves: 129P2/OlaHsd * C57BL/6) |
| Pth2 | Pth2$^{tm1Vlcg}$/Pth2$^{tm1Vlcg}$ (involves: 129 * C57BL/6) |
| Pvrl2 | Pvrl2$^{tm1Smu}$/Pvrl2$^{tm1Smu}$ (involves: 129X1/SvJ * C57BL/6 * DBA/2) |
| Pvrl2 | Pvrl2$^{tm1Vrr}$/Pvrl2$^{tm1Vrr}$ (involves: 129S1/Sv * 129X1/SvJ * C57BL/6) |
| Pvrl3 | Pvrl3$^{tm1Ytk}$/Pvrl3$^{tm1Ytk}$ (either: (involves: 129X1/SvJ * C57BL * DBA) or (involves: 129X1/SvJ * BALB/cA * C57BL * DBA)) |
| Rabl2 | Rabl2$^{mot}$/Rabl2$^{mot}$ (involves: C57BL/6 * CBA) |
| Rabl2 | Rabl2$^{mot}$/Rabl2$^{mot}$ (C57BL/6(CBA)-Rabl2$^{mot}$) |
| Rad21l | Rad21l$^{tm1Amp}$/Rad21l$^{tm1Amp}$ (involves: 129 * C57BL/6) |
| Rad23b | Rad23b$^{tm1Gvh}$/Rad23b$^{tm1Gvh}$ (involves: 129P2/OlaHsd * C57BL/6) |
| Rad51c | Rad51c$^{tm1Sks}$/Rad51c$^{tm1.1Sks}$ (involves: 129/Sv * C57BL/6J * FVB/N) |
| Ranbp1 | Ranbp1$^{tm1Yyo}$/Ranbp1$^{tm1Yyo}$ (involves: 129S2/SvPas * C57BL/6) |
| Ranbp9 | Ranbp9$^{Gt(RHA056)Byg}$/Ranbp9$^{Gt(RHA056)Byg}$ (B6.129P2-Ranbp9$^{Gt(RHA056)Byg}$) |
| Rara | Rara$^{tm1Ipc}$/Rara$^{tm1Ipc}$ (involves: 129S2/SvPas) |
| Rara | Rara$^{tm1Ipc}$/Rara$^{tm1Ipc}$ (involves: 129S2/SvPas * C57BL/6) |
| Rara | Rara$^{tm3.1Ipc}$/Rara$^{tm3.1Ipc}$ (involves: 129/Sv * C57BL/6 * SJL) |
| Rarg | Rarg$^{tm1Ipc}$/Rarg$^{tm1Ipc}$ (involves: 129S2/SvPas) |
| Rarg | Rarg$^{tm3.1Ipc}$/Rarg$^{tm3.1Ipc}$ (involves: C57BL/6 * SJL) |
| Rec8 | Rec8$^{tm1Mjm}$/Rec8$^{tm1Mjm}$ (either: (involves: 129S1/Sv * 129X1/SvJ) or (involves: 129S1/Sv * C57BL/6)) |
| Reln | Reln$^{rl}$/Reln$^{rl}$ (Not Specified) |
| repro2 | repro2/repro2 (involves: C3HeB/FeJ * C57BL/6J) |
| repro3 | repro3/repro3 (involves: C3HeB/FeJ * C57BL/6J) |
| repro4 | repro4/repro4 (B6; C3Fe-repro4/J) |
| repro10 | repro10/repro10 (involves: C3HeB/FeJ * C57BL/6J) |
| repro12 | repro12/repro12 (involves: C3HeB/FeJ * C57BL/6J) |
| repro13 | repro13/repro13 (involves: C3HeB/FeJ * C57BL/6J) |
| repro14 | repro14/repro14 (B6; C3Fe-repro14/J) |
| repro15 | repro15/repro15 (involves: C3HeB/FeJ * C57BL/6J) |
| repro16 | repro16/repro16 (involves: C3HeB/FeJ * C57BL/6J) |
| repro17 | repro17/repro17 (involves: C3HeB/FeJ * C57BL/6J) |
| repro20 | repro20/repro20 (involves: C3HeB/FeJ * C57BL/6J) |
| repro21 | repro21/repro21 (involves: C3HeB/FeJ * C57BL/6J) |
| repro22 | repro22/repro22 (involves: C3HeB/FeJ * C57BL/6J) |
| repro23 | repro23/repro23 (involves: C3HeB/FeJ * C57BL/6J) |
| repro24 | repro24/repro24 (involves: C3HeB/FeJ * C57BL/6J) |
| repro26 | repro26/repro26 (involves: C3HeB/FeJ * C57BL/6J) |
| repro27 | repro27/repro27 (involves: C3HeB/FeJ * C57BL/6J) |
| repro28 | repro28/repro28 (involves: C3HeB/FeJ * C57BL/6J) |
| repro29 | repro29/repro29 (involves: C3HeB/FeJ * C57BL/6J) |
| repro30 | repro30/repro30 (involves: C3HeB/FeJ * C57BL/6J) |
| repro31 | repro31/repro31 (involves: C3HeB/FeJ * C57BL/6J) |
| repro33 | repro33/repro33 (involves: C3HeB/FeJ * C57BL/6J) |
| repro36 | repro36/repro36 (B6; C3Fe-repro36/J) |
| repro46 | repro46/repro46 (B6; C3Fe-repro46/J) |
| repro47 | repro47/repro47 (involves: C3HeB/FeJ * C57BL/6J) |
| repro48 | repro48/repro48 (involves: C3HeB/FeJ * C57BL/6J) |
| repro49 | repro49/repro49 (involves: C3HeB/FeJ * C57BL/6J) |
| repro50 | repro50/repro50 (involves: C3HeB/FeJ * C57BL/6J) |
| repro51 | repro51/repro51 (involves: C3HeB/FeJ * C57BL/6J) |
| repro52 | repro52/repro52 (involves: C3HeB/FeJ * C57BL/6J) |
| repro53 | repro53/repro53 (involves: C3HeB/FeJ * C57BL/6J) |
| repro54 | repro54/repro54 (involves: C3HeB/FeJ * C57BL/6J) |
| repro57 | repro57/repro57 (B6; C3Fe-repro57/J) |
| Ret | Ret$^{tm2.1Cos}$/Ret$^{tm2.1Cos}$ (involves: 129S1/Sv * C57BL/6J * FVB/N) |
| Rimbp3 | Rimbp3$^{tm1Gxu}$/Rimbp3$^{tm1Gxu}$ (involves: 129/Sv * ICR) |
| Rnf8 | Rnf8$^{Gt(RRR260)Byg}$/Rnf8$^{Gt(RRR260)Byg}$ (involves: 129P2/OlsHsd * C57BL/6) |
| Rnf17 | Rnf17$^{tm1Jw}$/Rnf17$^{tm1Jw}$ (involves: 129 * C57BL/6) |
| Rnf41 | Rnf41$^{TgTn(sb-rtTa, Tyr)2435COve}$/Rnf41$^{TgTn(sb-rtTa, Tyr)2435COve}$ (involves: C57BL/6 * FVB/N) |
| Rorb | Rorbm$^{1Btlr}$/Rorb$^{1Btlr}$ (C57BL/6J-Rorb$^{1Btlr}$) |
| Ros1 | Ros1$^{tm1Cbm}$/Ros1$^{tm1Cbm}$ (involves: 129P2/OlaHsd) |
| Ros1 | Ros1$^{tm1Cbm}$/Ros1$^{tm1Cbm}$ (involves: 129P2/OlaHsd * C57BL/6) |
| Ros1 | Ros1$^{tm2Cbm}$/Ros1$^{tm2Cbm}$ (involves: 129P2/OlaHsd) |
| Rsph1 | Rsph1$^{tm1Htan}$/Rsph1$^{tm1Htan}$ (involves: 129S1/Sv * C57BL/6J) |
| Runx1t1 | Runx1t1$^{tm1Fc}$/Runx1t1$^{tm1Fc}$ (involves: 129S/SvEv * C57BL/6) |
| Rxfp2 | Rxfp2$^{tm1Ala}$/crsp (involves: 129S7/SvEvBrd * C57BL/6J * FVB/N) |
| Rxfp2 | Rxfp2$^{tm1Ala}$/Rxfp2$^{tm1Ala}$ (involves: 129S7/SvEvBrd * C57BL/6J) |
| Rxrb | Rxrb$^{tm1Ipc}$/Rxrb$^{tm1Ipc}$ (involves: 129S2/SvPas) |
| Safb | Safb$^{tm1So}$/Safb$^{tm1So}$ (involves: 129 * C57BL/6J) |
| Sbf1 | Sbf1$^{tm1Mlc}$/Sbf1$^{tm1Mlc}$ (involves: C57BL/6) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Scmh1 | Scmh1$^{tm1Hfko}$/Scmh1$^{tm1Hfko}$ (involves: 129S1/Sv * 129X1/SvJ * C57BL/6) |
| Sept4 | Sept4$^{tm1Hs}$/Sept4$^{tm1Hs}$ (involves: 129/Sv * 129P2/OlaHsd * C57BL/6J) |
| Sept4 | Sept4$^{tm1Ksh}$/Sept4$^{tm1Ksh}$ (involves: 129X1/SvJ * C57BL/6J) |
| Sept12 | Sept12$^{tm1.1Plk}$/Sept12$^+$ (chimera involves: 129/Sv * C57BL/6) |
| Serpina5 | Serpina5$^{tm1Gel}$/Serpina5$^{tm1Gel}$ (involves: 129/Sv * Swiss) |
| Serpine2 | Serpine2$^{tm1Dmn}$/Serpine2$^{tm1Dmn}$ (involves: 129P2/OlaHsd * C57BL/6) |
| Sgol2 | Sgol2$^{Gt(D025805)Wrst}$/Sgol2$^{Gt(D025805)Wrst}$ (involves: 129S2/SvPas * C57BL/6) |
| Sgpl1 | Sgpl1$^{Gt(ROSA)78Sor}$/Sgpl1$^{Gt(ROSA)78Sor}$ (either: (involves: 129S4/SvJaeSor) or (involves: 129S4/SvJaeSor * C57BL/6)) |
| Sh3pxd2b | Sh3pxd2b$^{nee}$/Sh3pxd2b$^{nee}$ (B10.Cg-H2$^{n4}$Sh3pxd2b$^{nee}$/GrsrJ) |
| Siah1a | Siah1a$^{tm1Dolb}$/Siah1a$^{tm1Dolb}$ (involves: 129S1/Sv * C57BL/6J) |
| Sit1 | Sirt1$^{tm1Mcby}$/Sirt1$^{tm1Mcby}$ (involves: 129S1/Sv * 129X1/SvJ * CD-1) |
| Sit1 | Sirt1$^{tm1Mcby}$/Sirt1$^{tm1Mcby}$ (129/Sv-Sirt1$^{tm1Mcby}$) |
| Sit1 | Sirt1$^{tm1Mcby}$/Sirt1$^{tm1Mcby}$ (involves: 129S1/Sv * 129X1/SvJ) |
| Sit1 | Sirt1$^{tm2.1Mcby}$/Sirt1$^{tm2.1Mcby}$ (involves: 129S1/Sv * 129X1/SvJ * CD-1) |
| Sit6 | Sirt6$^{tm2.1Cxd}$/Sirt6$^{tm2.1Cxd}$ (involves: 129S6/SvEvTac * NIH Black Swiss) |
| Sit6 | Sirt6$^{tm2.2Cxd}$/Sirt6$^{tm2.2Cxd}$ (involves: 129S6/SvEvTac * FVB/N * NIH Black Swiss) |
| Six5 | Six5$^{tm1Rdd}$/Six5$^{tm1Rdd}$ (129S4/SvJae-Six5$^{tm1Rdd}$) |
| Slc4a2 | Slc4a2$^{tm1Jmed}$/Slc4a2$^{tm1Jmed}$ (involves: 129P2/OlaHsd * FVB) |
| Slc9a3 | Slc9a3$^{tm1Ges}$/Slc9a3$^{tm1Ges}$ (Not Specified) |
| Slc9a8 | Slc9a8$^{Gt(YHB273)Byg}$/Slc9a8$^{Gt(YHB273)Byg}$ (involves: 129P2/OlaHsd * Black Swiss) |
| Slc9c1 | Slc9c1$^{tm1Gar}$/Slc9c1$^{tm1Gar}$ (involves: 129S6/SvEvTac * C57BL/6J) |
| Scl12a2 | Scl12a2$^{tm1Bhk}$/Scl12a2$^{tm1Bhk}$ (involves: 129P2/OlaHsd * C57BL/6J * DBA/2J) |
| Scl12a2 | Scl12a2$^{tm2Bhk}$/Scl12a2$^{tm2Bhk}$ (involves: 129P2/OlaHsd * C57BL/6J * DBA/2J) |
| Scl12a2 | Scl12a2$^{tm2Bhk}$/Scl12a2$^{tm2Bhk}$ (involves: 129P2/OlaHsd * C57BL/6J * DBA/2J) |
| Slc19a2 | Slc19a2$^{tm1Ejn}$/Slc19a2$^{tm1Ejn}$ (involves: 129S4/SvJae * 129S6/SvEvTac) |
| Slc19a2 | Slc19a2$^{tm1Gelb}$/Slc19a2$^{tm1Gelb}$ (involves: 129X1/SvJ) |
| Slc25a31 | Slc25a31$^{tm1Nte}$/Slc25a31$^{tm1Nte}$ (involves: 129S1/Sv * 129X1/SvJ * C57BL/6) |
| Slc26a8 | Slc26a8$^{tm1Ggac}$/Slc26a8$^{tm1Ggac}$ (involves: 129S/SvEvBrd) |
| Smc1b | Smc1b$^{tm1Ham}$/Smc1b$^{tm1Ham}$ (involves: C57BL/6JJcl * DBA/2JJcl * ICR) |
| Smc1b | Smc1b$^{tm1Jess}$/Smc1b$^{tm2.2Jess}$ (involves: 129S6/SvEvTav * C57BL/6 * SJL) |
| Smcp | Smcp$^{tm1Wen}$/Smcp$^{tm1Wen}$ (involves: 129S1/Sv * 129X1/SvJ) |
| Snai2 | Snai2$^{tm2Grid}$/Snai2$^{tm2Grid}$ (involves: 129S1/Sv) |
| Sohlh2 | Sohlh2$^{tm1Miya}$/Sohlh2$^{tm1Miya}$ (involves: 129P2/OlaHsd * C57BL/6) |
| Sox3 | Sox3$^{tm1Ptho}$/Y (chimera involves: 129S1/Sv * 129X1/SvJ * C57BL/6 * DBA/2) |
| Sp4 | Sp4$^{tm1Ssp}$/Sp4$^{tm1Ssp}$ (involves: 129P2/OlaHsd * CF-1) |
| Sp4 | Sp4$^{tm1Sus}$/Sp4$^{tm1Sus}$ (involves: 129P2/OlaHsd * C57BL/6) |
| Spaca1 | Spaca1$^{tm1.1Osb}$/Spaca1$^{tm1.1Osb}$ (involves: 129S2/SvPas * C57BL * C57BL/6N * DBA) |
| Spag6 | Spag6$^{tm1Jfs}$/Spag6$^{tm1Jfs}$ (involves: 129X1/SvJ * C57BL/6J) |
| Spag16 | Spag16$^{tm1Jfs}$/Spag16$^+$ (chimera involves: 129/Sv * C57BL/6J) |
| Spag16 | Spag6$^{tm2Jfs}$/Spag6$^{tm2Jfs}$ (involves: 129S6/SvEvTac) |
| Spata22 | Spata22$^{repro42}$/Spata22$^{repro42}$ (involves: C4HeB/FeJ * C57BL/6J) |
| Spef2 | Spef2$^{bgh}$/Spef2$^{bgh}$ (involves: C57BL/6J * C57BL/10J) |
| Spef2 | Spef2$^{bgh}$/Spef2$^{bgh}$ (involves: 129S6/SvEvTac * C57BL/6J * C57BL/10J) |
| Spem1 | Spem1$^{tm1Wyan}$/Spem1$^{tm1Wyan}$ (involves: 129S1/Sv * 129X1/SvJ * C57BL/6J) |
| Spo11 | Spo11$^{tm1Mjn}$/Spo11$^{tm1Mjn}$ (involves: 129X1/SvJ * C57BL/6) |
| Spo11 | Spo11$^{tm1Nkl}$/Spo11$^{tm1Nkl}$ (involves: 129P2/OlaHsd) |
| Spo11 | Spo11$^{tm1Rdco}$/Spo11$^{tm1Rdco}$ (involves: 129S6/SvEvTac) |
| Sptbn4 | Sptbn4$^{qv-10J}$/Sptbn4$^{qv-10J}$ (involves: BALB/cJ * C57BL/6J) |
| Sptbn4 | Sptbn4$^{qv-11J}$/Sptbn4$^{qv-11J}$ (C57BL/6J-Sptbn4$^{qv-11J}$/J) |
| Sptbn4 | Sptbn4$^{qv-Ind}$/Sptbn4$^{qv-Ind}$ (B6.B10-Sptbn4$^{qv-Ind}$) |
| Stam | Stam$^{tm1Sug}$/Stam$^{tm1Sug}$ (involves: 129S4/SvJae * C57BL/6) |
| Stk11 | Stk11$^{tm1Kels}$/Stk11$^{tm1Kels}$ (Not Specified) |
| Stk36 | Stk36$^{tm1Fjs}$/Stk36$^{tm1Fjs}$ (involves: 129S1/Sv * C57BL/6) |
| Stx2 | Stx2$^{repro34}$/Stx2$^{repro34}$ (involves: C3HeB/FeJ * C57BL/6J) |
| Stx2 | Stx2$^{tm1Dcru}$/Stx2$^{tm1Dcru}$ (involves: 129X1/SvJ * C57BL/6J) |
| Styx | Styx$^{tm1.1Jedi}$/Styx$^{tm1.1Jedi}$ (either: (involves: 129S1/Sv * 129X1/SvJ * C57BL/6) or (involves: C57BL/6)) |
| Styx | Styx$^{tm1Jedi}$/Styx$^{tm1Jedi}$ (either: (involves: 129S1/Sv * 129X1/SvJ * C57BL/6) or (involves: C57BL/6)) |
| Sun1 | Sun1$^{tm1.1Ktj}$/Sun1$^{tm1.1Ktj}$ (involves: C57BL/6J * FVB/N) |
| Sun1 | Sun1$^{tm1Mhan}$/Sun1$^{tm1Mhan}$ (involves: 129S6/SvEvTac) |
| Swm2 | swm2/swm2 (involves: C3HeB/FeJ * C57BL/6J) |
| Swm6 | swm6/swm6 (involves: C3HeB/FeJ * C57BL/6) |
| Syce1 | Syce1$^{tm1Hgu}$/Syce1$^{tm1Hgu}$ (involves: 129S7/SvEvBrd * C57BL/6) |
| Syce2 | Syce2$^{Gt(FHCRC-GT-S8-7E1)Sor}$/Syce2$^{Gt(FHCRC-GT-S8-7E1)Sor}$ (involves: C57BL/6) |
| Syce3 | Syce3$^{tm1Rben}$/Syce3$^{tm1Rben}$ (involves: 129S1/Sv * 129X1/SvJ * C57BL/6) |
| Sycp1 | Sycp1$^{tm1Aps}$/Sycp1$^{tm1Aps}$ (involves: 129P2/OlaHsd * C57BL/6) |
| Sycp2 | Sycp2$^{tm1Jw}$/Sycp2$^{tm1Jw}$ (involves: 129S4/SvJae * C57BL/6) |
| Sycp3 | Sycp3$^{tm1Hoog}$/Sycp3$^{tm1Hoog}$ (involves: 129P2/OlaHsd * C57BL/6) |
| Taldo1 | Taldo1$^{tm1Perl}$/Taldo1$^{tm1Perl}$ (involves: 129S6/SvEvTac * C57BL/6) |
| Tarbp2 | Tarbp2$^{tm1Reb}$/Tarbp2$^{tm1Reb}$ (Not Specified) |
| Tbpl1 | Tbpl1$^{tm1Rgr}$/Tbpl1$^{tm1Rgr}$ (involves: C57BL/6) |
| Tbpl1 | Tbpl1$^{tm1Saco}$/Tbpl1$^{tm1Saco}$ (involves: 129S2/SvPas * C57BL/6) |
| Tcte3 | Tcte3$^{tm1June}$/Tcte3$^{tm1June}$ (involves: 129S1/Sv * 129X1/SvJ * C57BL/6J) |

TABLE 2-continued

FERTILITY GENES AND ILLUSTRATIVE MUTATIONS LEADING TO INFERTILITY

| Fertility Gene(s) | Allelic Composition (Genetic Background) |
|---|---|
| Tdrd1 | Tdrd1$^{tm1Chum}$/Tdrd1$^{tm1Chum}$ (involves: 129S1/Sv * 129X1/SvJ * C57BL/6) |
| Tdrd5 | Tdrd5$^{tm1Salt}$/Tdrd5$^{tm1Salt}$ (involves: C57BL/6 * CBA) |
| Tdrd6 | Tdrd6$^{tm1Chum}$/Tdrd6$^{tm1Chum}$ (involves: 129S4/SvJae * C57BL/6) |
| Tdrd6 | Tdrd6$^{tm1Chum}$/Tdrd6$^{tm1Chum}$ |
| Tdrd7 | Tdrd7$^{tm1.1Chum}$/Tdrd7$^{tm1.1Chum}$ (involves: 129S4/SvJae * 129S6/SvEvTac * C57BL/6) |
| Tdrd6 | Tdrd6$^{tm1Jess}$/Tdrd6$^{tm1Jess}$ (either: (involves: 129S6/SvEvTac * C57BL/6) or (involves: 129S1/Sv * 129X1/SvJ * C57BL/6) |
| Tdrd7 | Tdrd7$^{nmf166}$/Tdrd7$^{nmf166}$ (involves: C3H * C57BL/6J) |
| Tdrd7 | Tdrd7$^{tm1.1Chum}$/Tdrd7$^{tm1.1Chum}$ (involves: 129S6/SvEvTac * C57BL/6) |
| Tdrd9 | Tdrd9$^{tm1.1Chum}$/Tdrd9$^{tm1.1Chum}$ (involves: 129P2/OlaHsd * C57BL/6 * SJL) |
| Tekt2 | Tekt2$^{Gt(OST12401)Lex}$/Tekt2$^{Gt(OST12401)Lex}$ (involves: 129S5/SvEvBrd * C57BL/6) |
| Tex11 | Tex11$^{tm1Jw}$/Y |
| 2Mrt | Tg(ACTB-cre)2Mrt/0 (involves: 129S4/SvJae * C57BL/6 * FVB/N) |
| Tex12 | Tex12$^{tm1Hoog}$/Tex12$^{tm1Hoog}$ (involves: 129S2/SvPas) |
| Tex14 | Tex14$^{tm1Zuk}$/Tex14$^{tm1Zuk}$ (129S6/SvEvTac) |
| Tex14 | Tex14$^{tm1Zuk}$/Tex14$^{tm1Zuk}$ (involves: 129S6/SvEvTac * C57BL/6) |
| Tex15 | Tex15$^{tm1Jw}$/Tex15$^{tm1Jw}$ (involves: 129S4/SvJae * C57BL/6) |
| Tex101Anak | Tex101$^{tm1Osh}$/Tex101$^{tm1Osh}$ (involves: C57BL/6NCr) |
| Theg | Theg$^{Tg(PDE5A)1Ynk}$/Theg$^{Tg(PDE5A)1Ynk}$ (involves: C3H) |
| Tial1 | Tial1$^{tm1Mst}$/Tial1$^{tm1Mst}$ (involves: 129S2/SvPas * C57BL/6) |
| Tim | Tim$^{T(4;17)3Lws}$/Tim$^+$ (involves: C57BL/6J * DBA/2J) |
| Tlr6 | Tlr6$^{m4Bbr}$/Tlr6$^{m4Bbr}$ (C57BL/6J-Tlr6$^{m4Bbr}$) |
| Tmf1 | Tmf1$^{tm1Unlr}$/Tmf1$^{tm1Unlr}$ (involves: 129/Sv * ICR) |
| Tnp1 | Tnp1$^{tm1Mlm}$/Tnp1$^{tm1Mlm}$ (involves: 129S7/SvEvBrd * C57BL/6J) |
| Tnp2 | Tnp2$^{tm1Wen}$/Tnp2$^{tm1Wen}$ (involves: 129S1/Sv * 129X1/SvJ) |
| Tpgs1 | Tpgs1$^{Gt(ROSA22)Soc}$/Tpgs1$^{Gt(ROSA22)Soc}$ (involves: 129S/SvEv * C57BL/6) |
| Tpst2 | Tpst2$^{tm1Klm}$/Tpst2$^{tm1Klm}$ (involves: 129S6/SvEvTac * 129S7/SvEvBrd) |
| Trp73 | Trp73$^{tm1Mak}$/Trp73$^{tm1Mak}$ (involves: 129P2/OlaHsd * C57BL/6J) |
| Tsc22d3 | Tsc22d3$^{tm1.1Ric}$/Y (involves: 129S7/SvEvBrd * C57BL/6) |
| Tshr | Tshr$^{hyt}$/Tshr$^{hyt}$ (involves: BALB/cByJ * RF/J) |
| Tssk1/Tssk2 | Tssk1/Tssk2$^{tm1.1Agr}$/Tssk1/Tssk2$^{tm1.1Agr}$ (B6.129S5-Tssk1/Tssk2$^{tm1.1Agr}$) |
| Tssk1/Tssk2 | Tssk1/Tssk2$^{tm1.1Agr}$/Tssk1/Tssk2$^{tm1.1Agr}$ (B6.129S5-Tssk1/Tssk2$^{tm1.1Agr}$) |
| Tssk1/Tssk2 | Tssk1/Tssk2$^{tm1Joch}$/Tssk1$^+$ (chimera involves: 129X1/SvJ) |
| Tssk1/Tssk2 | Tssk1/Tssk2$^{tm1Joch}$/Tssk2$^+$ (chimera involves: 129X1/SvJ) |
| Tssk6 | Tssk6$^{tm1Grj}$/Tssk6$^{tm1Grj}$ (involves: 129 * C57BL/6) |
| Ttll1 | Ttll1$^{Gt(OST372941)Lex}$/Ttll1$^{Gt(OST372941)Lex}$ (involves: 129S5/SvEvBrd * C57BL/6) |
| Tyr | Tyr$^{c-47H}$/Tyr$^{c-47H}$ (involves: 101/H * C3H/HeH) |
| Tyrp1 | Tyrp1$^{b-1FCHLc}$/Tyrp1$^{b-1FCHLc}$ (involves: 101/RI * C3H/RI) |
| Ubb | Ubb$^{tm1Rrk}$/Ubb$^{tm1Rrk}$ (involves: 129S1/Sv * 129X1/SvJ * C57BL/6) |
| Ube2b | Ube2b$^{tm1Jhjh}$/Ube2b$^{tm1Jhjh}$ (either: (involves: 129P2/OlaHsd * C57BL/6) or (involves: 129P2/OlaHsd * FVB/N)) |
| Ube2b | Ube2b$^{tm1Jhjh}$/Ube2b$^{tm1Jhjh}$ (involves: 129P2/OlaHsd * FVB/NJ) |
| Ubr2 | Ubr2$^{tm1Ytkw}$/Ubr2$^{tm1Ytkw}$ (involves: 129S1/Sv * C57BL/6) |
| Unc5c | Unc5c$^{rcm}$/Unc5c$^{rcm}$ (C57BL/6J-Unc5c$^{rcm}$) |
| Usp1 | Usp1$^{tm1.1Ada}$/Usp1$^{tm1.1Ada}$ (C57BL/6-Usp1$^{tm1.1Ada}$) |
| Usp14 | Usp14$^{ax-J}$/Usp14$^{ax-J}$ (involves: STOCK Mafb$^{kr}$) |
| Utp14b | Utp14b$^{jsd}$/Utp14b$^{jsd}$ (involves: C3H/HeJ * C57BL/6J) |
| Vangl2 | Vangl2$^{Lp}$/Vangl2$^{Lp}$ (B6.A(Cg)-Vangl2$^{Lp}$) |
| Vangl2 | Vangl2$^{ska17}$/Vangl2$^{ska17}$ (involves: 129S6/SvEvTac * C57BL/6J) |
| Vdac3 | Vdac3$^{tm1Wjc}$/Vdac3$^{tm1Wjc}$ (Not Specified) |
| Vdr | Vdr$^{tm1Ska}$/Vdr$^{tm1Ska}$ (involves: C57BL/6 * CBA) |
| Vrk1 | Vrk1$^{Gt(RRR178)Byg}$/Vrk1$^{Gt(RRR178)Byg}$ (involves: 129P2/OlaHsd * C57BL/6) |
| Vsx2 | Vsx2$^{or-2J}$/Vsx2$^{or-2J}$ (NOR2/LtDn-Vsx2$^{or-2J}$/J) |
| Wnt7a | Wnt7a$^{px-2J}$/Wnt7a$^{px-2J}$ (B6; C3Fe-Wnt7a$^{px-2J}$/GrsrJ) |
| Wnt7a | Wnt7a$^{px-J}$/Wnt7a$^{px-J}$ (C57BL/6J-Wnt7a$^{px-J}$/GrsrJ) |
| Wnt7a | Wnt7a$^{px}$/Wnt7a$^{px}$ (involves: STOCK Sox18$^{Ra}$) |
| Wnt7a | Wnt7a$^{tm1Amc}$/Wnt7a$^{tm1Amc}$ (involves: 129S1/Sv) |
| Wt1 | Wt1$^{tm2Hst}$/Wt1$^+$ (chimera involves: 129P2/OlaHsd * C57BL/6JLac * CBA/CaLac) |
| Ybx2 | Ybx2$^{tm1Nbh}$/Ybx2$^{tm1Nbh}$ (involves: 129S7/SvEvBrd) |
| Ybx3 | Ybx3$^{tm1Ley}$/Ybx3$^{tm1Ley}$ (involves: 129X1/SvJ * C57BL/6) |
| Zbtb16 | Zbtb16$^{lu-Sfd}$/Zbtb16$^{lu-Sfd}$ (involves: C57BL/6 * Swiss) |
| Zbtb16 | Zbtb16$^{lu-Sfd}$/Zbtb16$^{lu-Sfd}$ (involves: C57BL/6) |
| Zbtb16 | Zbtb16$^{lu}$/Zbtb16$^{lu}$ (Not Specified) |
| Zc3hc1 | Zc3hc1$^{tm1.2duy}$/Zc3hc1$^{tm1.2duy}$ (B6.129S6(Cg)-Zc3hc1$^{tm1.2duy}$) |
| Zfp148 | Zfp148$^{tm1Kll}$/Zfp148$^+$ (Not Specified) |
| Zfp384 | Zfp384$^{tm1Tnk}$/Zfp384$^{tm1Tnk}$ (involves: C57BL/6 * CBA) |
| Zglp1 | Zglp1$^{tm1Eem}$/Zglp1$^{tm1Eem}$ ((129X1/SvJ x 129S1/Sv)F1-Kitl$^+$) |
| Zpbp | Zpbp$^{tm1Zuk}$/Zpbp$^{tm1Zuk}$ (involves: 129S7/SvEvBrd * C57BL/6J) |
| Zpbp2 | Zpbp2$^{tm1Zuk}$/Zpbp$^{tm1Zuk}$ Zpbp2$^{tm1Zuk}$/Zpbp2$^{tm1Zuk}$ (involves: 129S7/SvEvBrd * C57BL/6J) |

In other embodiments, the fertility gene is selected from spermatogenesis genes, illustrative examples of which include those disclosed in US. Pat. Appl. Pub. 2005/0176943, the entire content of which are incorporated herein by reference. Representative genes include those comprising transcripts with nucleic acid sequences set out in SEQ ID NOs: 1-89 of this publication. Non-limiting examples of these genes include AKAP110, Rbcc728, Trim36, Nopp140, ATR, HSpb, Spergen-1, arylsulfatase A, Drctnnbla, CDC14B, cystatin-related epididymal spermatogenic protein, pregnancy-induced growth inhibitor, fatty acid coenzyme A ligase, long chain, Fern, major 80,000 Mr fibrous sheath component, Glycerol phosphate dehydrogenase 1, mitochondrial, Lim domains containing 1, oaz-t, pctp-1, testis-specific phosphoglycerate kinase, phospholipase C delta 4, protamine 1, protamine 2, scot-t1, scot-t2, mitochondrial capsule selenoprotein, Sperizin, oppo 1, Gal beta-1, 3-GalNAc-specific GalNAc alpha-2, 6-sialyltransferase, suppressor of fused homolog, t-actin 1, t-actin 2, t-complex Tcp-10a, tektin-t, teek 1, TP-2, tsec-1, tssk 1.2 substrate, serine/threonine kinase 228 (spermiogenesis associated), tsga2, Gapd-S, meichroacidin, halap-X, Ssecks, gsg1, haspin, gsg3, hils1, shippo1, and putative lysophosphatidic acid acyltransferase.

In advantageous embodiments, the fertility gene is a gene located on a sex chromosome. In illustrative examples of this type, the fertility gene is located on the X chromosome (i.e., a X-linked fertility gene) such as, but not limited to, GILZ (TSC22d3).

The fertility gene may be disrupted using any suitable technique. In some embodiments, disruption is carried out using a targeting construct in which a portion of the fertility gene is operatively positioned between two flanking portions of a targeting cassette, which are sufficiently homologous with regions of a target site in the cellular genome to permit homologous recombination between the targeting cassette and the target site. For example, the target site may comprise an exonic or coding sequence, or a control sequence (e.g., a promoter), of the fertility gene and in certain embodiments, a disruptor sequence (e.g., marker gene) is positioned by the flanking portions of the targeting cassette to disrupt or replace at least a portion of the fertility gene thereby rendering the fertility gene inactive and thus non-functional. In illustrative examples of this type, one of the flanking portions is substantially homologous to a portion of the 5' untranslated sequence of the fertility gene, and the other substantially homologous to at least a portion of the 3' untranslated sequence of the endogenous gene. In other illustrative examples, the flanking portions of the targeting cassette are substantially homologous to regions of the fertility gene that border an intervening coding sequence that encodes a domain of a polypeptide encoded by the fertility gene, which is required for fertility. In these embodiments, site-specific homologous recombination between the targeting construct and the target site subsequently results in replacement of at least a portion of the fertility gene with the marker gene and disruption of the fertility gene.

In specific embodiments, a fertility gene is provided with recombinase recognition sites (also known as acceptor sequences) that are located within or adjacent to that gene, and that are recognized by a site-specific recombinase protein that acts as a fertility gene disruptor molecule by binding to and catalyzing site-specific recombination between the recombinase recognition sites leading to disruption of that gene. The recombinase may catalyze intra- or intermolecular recombination between the sites. For example in the case of intra-molecular recombination, when two recombination sites having an identical orientation exist within the same molecule, site-specific recombination between the sites will excise a DNA sequence flanked by the sites (an excision reaction) whereas in inter-molecular recombination, site-specific recombination between two recombination recognition sites on different molecules will result in co-integration (an insertion reaction). In illustrative examples of these embodiments, a transgene comprising a site-specific recombinase coding sequence that is operably linked to a promoter is used to conditionally disrupt the fertility gene. Illustrative recombinases, which are site-specific, include Cre, modified Cre, Dre, Hp, FLP-wild type (wt), FLP-L, FLPe, Flpo or phiC31. Non-limiting examples of recombinase recognition sites include loxP, FRT, rax and attP/B. Recombination may be effected by any art-known method, e.g., the method of Doetschman et al. (1987, *Nature* 330:576-578); the method of Thomas et al. (1986, *Cell* 44:419-428); the Cre-loxP recombination system (Sternberg and Hamilton, 1981, *J. Mol. Biol.* 150:467-486; Lakso et al., 1992, *Proc. Natl. Acad. Sci. USA* 89:6232-6236); the FLP recombinase system of *Saccharomyces cerevisiae* (O'Gorman et al., 1991, *Science* 251:1351-1355; Lyznik et al., 1996, *Nucleic Acids Res.* 24(19):3784-3789); the Cre-loxP-tetracycline control switch (Gossen and Bujard, 1992, *Proc. Natl. Acad. Sci. USA* 89:5547-51); and ligand-regulated recombinase system (Kellendonk et al., 1999, *J. Mol. Biol.* 285:175-82). Desirably, the recombinase is highly active, e.g., the Cre-loxP or the FLPe system, and has enhanced thermostability (Rodrguez et al., 2000, *Nature Genetics* 25:139-40). In specific embodiments, at least a portion of the fertility gene (including its regulatory sequences, if appropriate) is flanked by either loxP target sites, which are specifically recognized by a Cre recombinase, or FRT target sites, which are specifically recognized by a FLP recombinase. An illustrative example of a loxP target site sequence is 5'-ATAACTTCGTATAGCATACAT-TATACGAAGTTAT-3' [SEQ ID NO:1]. An illustrative example of an FRT target site sequence is 5'-GAAGTTCC-TATTCCGAAGTTCCTATTCTCTAGTAAGTATAG-GAACTTC-3' [SEQ ID NO:2].

In other embodiments, the fertility gene disruptor molecule is an expression product that inhibits expression of the fertility gene by RNA interference (RNAi) or by post-transcriptional gene silencing (PTGS). In illustrative examples of this type, the expression product is a RNA molecule (e.g., siRNA, shRNA, miRNA, dsRNA etc.) that comprises a targeting region corresponding to a nucleotide sequence of the fertility gene and that attenuates or otherwise disrupts the expression of the fertility gene. Non-limiting examples of such fertility genes are listed in Table 2 and elsewhere herein.

In illustrative examples, the targeting sequence displays at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% identity to a nucleotide sequence of the fertility gene. In other illustrative examples, the targeting sequence hybridizes to a nucleotide sequence of the target gene under at least low stringency conditions, more suitably under at least medium stringency conditions and even more suitably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. Desirably, the targeting sequence hybridizes to a nucleotide sequence of the fertility gene under physiological conditions.

Other stringent conditions are well known in the art. A skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al., supra at sections 1.101 to 1.104.

Suitably, the targeting region has sequence identity with the sense strand or antisense strand of the fertility gene. In certain embodiments, the RNA molecule is unpolyadenylated, which can lead to efficient reduction in expression of the fertility gene, as described for example by Waterhouse et al. in U.S. Pat. No. 6,423,885.

Typically, the length of the targeting region may vary from about 10 nucleotides (nt) up to a length equaling the length (in nucleotides) of the fertility gene. Generally, the length of the targeting region is at least 10, 12, 13, 14, 15, 16, 17, 18, 19, 20, 21, 22, 23, 24, 25 nt, usually at least about 50 nt, more usually at least about 100 nt, especially at least about 150 nt, more especially at least about 200 nt, even more especially at least about 500 nt. It is expected that there is no upper limit to the total length of the targeting region, other than the total length of the fertility gene. However for practical reason (such as e.g., stability of the targeting constructs) it is expected that the length of the targeting region should not exceed 5000 nt, particularly should not exceed 2500 nt and could be limited to about 1000 nt.

The RNA molecule may further comprise one or more other targeting regions (e.g., from about 1 to about 10, or from about 1 to about 4, or from about 1 to about 2 other targeting regions) each of which has sequence identity with a nucleotide sequence of the target gene. Generally, the targeting regions are identical or share at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity with each other.

The RNA molecule may further comprise a reverse complement of the targeting region. Typically, in these embodiments, the RNA molecule further comprises a spacer sequence that spaces the targeting region from the reverse complement. The spacer sequence may comprise a sequence of nucleotides of at least about 100-500 nucleotides in length, or alternatively at least about 50-100 nucleotides in length and in a further alternative at least about 10-50 nucleotides in length. Typically, the spacer sequence is a non-coding sequence, which in some instances is an intron. In embodiments in which the spacer sequence is a non-intron spacer sequence, transcription of the nucleic acid sequence will produce an RNA molecule that forms a hairpin or stem-loop structure in which the stem is formed by hybridization of the targeting region to the reverse complement and the loop is formed by the non-intron spacer sequence connecting these 'inverted repeats'. Alternatively, in embodiments in which the spacer sequence is an intron spacer sequence, the presence of intron/exon splice junction sequences on either side of the intron sequence facilitates the removal of what would otherwise form a loop structure and the resulting RNA will form a double-stranded RNA (dsRNA) molecule, with optional overhanging 3' sequences at one or both ends. Such a dsRNA transcript is referred to herein as a "perfect hairpin". The RNA molecules may comprise a single hairpin or multiple hairpins including "bulges" of single-stranded RNA occurring adjacent to regions of double-stranded RNA sequences.

Alternatively, a dsRNA molecule as described above can be conveniently obtained using an additional polynucleotide from which a further RNA molecule is producible, comprising the reverse complement of the targeting region. In this embodiment, the reverse complement of the targeting region hybridizes to the targeting region of the RNA molecule transcribed from the second polynucleotide.

In another example, a dsRNA molecule as described above is prepared using a second polynucleotide that comprises a duplex, wherein one strand of the duplex shares sequence identity with a nucleotide sequence of the target gene and the other shares sequence identity with the complement of that nucleotide sequence. In this embodiment, the duplex is flanked by two promoters, one controlling the transcription of one of the strands, and the other controlling the transcription of the complementary strand. Transcription of both strands produces a pair of RNA molecules, each comprising a region that is complementary to a region of the other, thereby producing a dsRNA molecule that inhibits the expression of the fertility gene.

In another example, PTGS of the fertility gene is achieved using the strategy by Glassman et al. described in U.S. Patent Application Publication No 2003/0036197. In this strategy, suitable nucleic acid sequences and their reverse complement can be used to alter the expression of any homologous, endogenous target RNA (i.e., comprising a transcript of the fertility gene) which is in proximity to the suitable nucleic acid sequence and its reverse complement. The suitable nucleic acid sequence and its reverse complement can be either unrelated to any endogenous RNA in the host or can be encoded by any nucleic acid sequence in the genome of the host provided that nucleic acid sequence does not encode any target mRNA or any sequence that is substantially similar to the target RNA. Thus, in some embodiments of the present invention, the RNA molecule further comprises two complementary RNA regions which are unrelated to any endogenous RNA in the host cell and which are in proximity to the targeting region. In other embodiments, the RNA molecule further comprises two complementary RNA regions which are encoded by any nucleic acid sequence in the genome of the host provided that the sequence does not have sequence identity with the nucleotide sequence of the fertility gene, wherein the regions are in proximity to the targeting region. In the above embodiments, one of the complementary RNA regions can be located upstream of the targeting region and the other downstream of the targeting region. Alternatively, both the complementary regions can be located either upstream or downstream of the targeting region or can be located within the targeting region itself.

In some embodiments, the RNA molecule is an antisense molecule that is targeted to a specific region of RNA encoded by the fertility gene, which is critical for translation. The use of antisense molecules to decrease expression levels of a pre-determined gene is known in the art. Antisense molecules may be designed to correspond to full-length RNA transcribed from the fertility gene, or to a fragment or portion thereof. This gene silencing effect can be enhanced by transgenically over-producing both sense and antisense RNA of the fertility gene coding sequence so that a high amount of dsRNA is produced as described for example above (see, for example, Waterhouse et al. (1998) *Proc Natl Acad Sci USA* 95:13959 13964).

In still other embodiments, the fertility gene disruptor molecule is an antibody that is immuno-interactive with a polypeptide product of the fertility gene. In non-limiting examples of this type, the polypeptide product is one that is encoded by a fertility gene listed in Table 2 and elsewhere herein. Exemplary antibodies for use in the practice of the present invention include monoclonal antibodies, Fv, Fab, Fab' and F(ab')$_2$ immunoglobulin fragments, as well as synthetic antibodies such as but not limited to single domain antibodies (DABs), synthetic stabilized Fv fragments, e.g., single chain Fv fragments (scFv), disulfide stabilized Fv fragments (dsFv), single variable region domains (dAbs) minibodies, combibodies and multivalent antibodies such as diabodies and multi-scFv or engineered human equivalents. Techniques for preparing and using various antibody-based constructs and fragments are well known in the art. Means for preparing and characterizing antibodies are also well known in the art. In illustrative examples, antibodies can be made by conventional immunization (e.g., polyclonal sera and hybridomas) with isolated, purified or recombinant peptides or proteins corresponding to at least a portion of a polypeptide product of a fertility gene, or as recombinant fragments corresponding to at least a portion of a polypeptide product of a fertility gene, usually expressed in *Escherichia coli*, after selection from phage display or ribosome display libraries (e.g., available from Cambridge Antibody Technology, BioInvent, Affitech and Biosite). Knowledge of the antigen-binding regions (e.g., complementarity-determining regions) of such antibodies can be used to prepare synthetic antibodies as described for example above.

3.2 Systems for Generating Non-Human Embryos with a Disrupted Fertility Gene

In accordance with the present invention, systems are used for generating non-human host embryo with disrupted fertility genes. For example, non-human embryos that comprise a disrupted fertility gene may be created by crossing: 1) a first animal strain carrying a disruptable fertility gene ("conditional infertility strain"); with 2) a second animal strain carrying an infertility-activating transgene that comprises a disruptor nucleotide sequence that codes for a fertility gene disruptor molecule that disrupts the disruptable fertility gene ("infertility-activating strain"), thereby generating transgenic non-human host embryos that comprise germ cells having a disrupted fertility gene. In some embodiments, female members of the first animal strain are crossed with male members of the second animal strain. As used herein, respective members of the first and second animal strains are breeding partners of a breeding pair of non-human animals.

In some embodiments, the fertility gene of the conditional infertility strain is in the form of a transgene ("conditional infertility transgene") in which it is operably linked to a promoter and to recombinase recognition sites that permit disruption of the fertility gene in the presence of a recombinase. In these embodiments, the infertility-activating transgene comprises a coding sequence for the recombinase operably linked to a promoter and the recombinase recognition sites are usually located within or adjacent to the fertility gene and mediate disruption of the fertility gene. In non-limiting examples of this type, the recombinase encoded by the infertility-activating transgene of the infertility-activating strain is Cre and the recombinase recognition sites included in the conditional infertility transgene of the conditional infertility strain are loxP sequences. In illustrative examples, crossing a female member of the conditional infertility strain that is homozygous for the conditional infertility transgene with a male member of the infertility-activating strain that is homozygous for the infertility-activating transgene produces non-human animal embryos with at least some germ cells having a heterologous disruption of the fertility gene. In advantageous examples, the fertility gene of the conditional infertility strain is located on the X chromosome (i.e., a X-linked fertility gene) and crossing a female member of the conditional infertility strain that is homozygous for the conditional infertility transgene with a male member of the infertility-activating strain that is homozygous for the infertility-activating transgene produces non-human animal embryos including male embryos with at least some germ cells having a homozygous disruption of the fertility gene.

In other embodiments, non-human host embryos that comprise a disrupted fertility gene are created by crossing: (1) a first animal strain carrying (a) a first conditional infertility transgene that comprises a first disruptable fertility gene and (b) a first infertility-activating transgene that comprises a gene that disrupts a second disruptable fertility gene ("first conditional infertility-activating strain"); with (2) a second animal strain carrying (a) a second conditional infertility transgene that comprises the second disruptable fertility gene and (b) a second infertility-activating transgene that comprises a gene that disrupts the first disruptable fertility gene ("second conditional infertility-activating strain"), wherein the first infertility-activating transgene specifically disrupts the second disruptable fertility gene and wherein the second infertility-activating transgene specifically disrupts the first disruptable fertility gene, thereby generating transgenic non-human host embryos that comprise germ cells having a disrupted fertility gene. Except for the elements of the first and second conditional infertility transgenes that mediate disruption of the first and second disruptable fertility genes in the presence of the infertility-activating transgenes, the fertility genes of the conditional infertility transgenes are suitably the same or corresponding genes. In these embodiments, crossing a breeding partner of the first conditional infertility-activating strain that is homozygous for the first conditional infertility transgene and the first infertility-activating transgene with a breeding partner of the second conditional infertility-activating strain that is homozygous for the second conditional infertility transgene and the second infertility-activating transgene produces non-human animal embryos with at least some germ cells having a homozygous disruption of the fertility gene. In some embodiments, female members of the first animal strain are crossed with male members of the second animal strain. In other embodiments, male members of the first animal strain are crossed with female members of the second animal strain.

In some embodiments, the first conditional infertility transgene comprises the first disruptable fertility gene operably connected to a promoter and to first recombinase recognition sites, which mediate disruption of the first disruptable fertility gene in the presence of a first recombinase, and the first infertility-activating transgene comprises a coding sequence for a second recombinase operably linked to a promoter, wherein the second recombinase specifically recognizes second recombinase recognition sites. The second conditional infertility transgene suitably comprises the second disruptable fertility gene operably connected to a promoter and to second recombinase recognition sites, which mediate disruption of the second disruptable fertility gene in the presence of the second recombinase, and the second infertility-activating transgene comprises a coding sequence for the first recombinase operably linked to a promoter, wherein the first recombinase specifically recognizes the first recombinase recognition sites. In illustrative examples of this type, the second recombinase encoded by the first infertility-activating transgene is FLP, the recombinase recognition sites included in the first conditional infertility transgene are loxP sequences, the first recombinase encoded by the second infertility-activating transgene is Cre, and the recombinase recognition sites included in the second conditional infertility transgene are Frt sequences. In other illustrative examples, the second recombinase encoded by the first infertility-activating transgene is Cre, the recombinase recognition sites included in the first conditional infertility transgene are Frt sequences, the first recombinase encoded by the second infertility-activating transgene is FLP, and the recombinase recognition sites included in the second conditional infertility transgene are loxP sequences.

In some embodiments, the second recombinase encoded by the first infertility-activating transgene is FLP, the target sites included in the first conditional infertility transgene are loxP sequences, the first recombinase encoded by the second infertility-activating transgene is Cre, and the target sites included in the second conditional infertility transgene are Frt sequences. In these embodiments, crossing a female member of the first conditional infertility-activating strain that is homozygous for the first conditional infertility transgene and the first infertility-activating transgene with a male member of the second conditional infertility-activating strain that is homozygous for the second conditional infertility transgene and the second infertility-activating transgene produces non-human animal embryos with at least some germ cells having a homozygous disruption of the fertility gene.

In still other embodiments, non-human embryos that comprise a disrupted fertility gene may be created by crossing: 1) a first animal strain carrying a disruptable fertility gene ("conditional infertility strain"); with 2) a second animal strain carrying an infertility-activating transgene that comprises a disruptor nucleotide sequence that codes for a fertility gene disruptor molecule that disrupts the disruptable fertility gene ("infertility-activating strain"), wherein the fertility gene disruptor is selected from inhibitory nucleic acids (e.g., inhibitory RNAs such as sense or antisense RNAs, molecules that mediate RNA interference such as siRNA, shRNA, miRNA; etc.), inhibitory polypeptides (e.g., antibodies, polypeptide-binding partners, dominant negative polypeptides, enzymes etc.) or any other molecule that inhibits the activity of the fertility gene or level or functional activity of an expression product of the fertility gene. In these embodiments, the infertility-activating transgene suitably comprises an expression-modulating element operably linked to the disruptor nucleotide sequence, wherein the element conditionally inhibits expression of the disruptor nucleotide sequence and the conditional infertility strain carries an activator transgene that inhibits the activity of the expression-modulating element, resulting in expression of the disruptor nucleotide sequence.

Thus, when a breeding partner of the conditional infertility strain is crossed with a breeding partner of the infertility-activating strain, embryos will form in which the activator transgene is expressed leading to inhibition of the expression-modulating element and to de-inhibition of expression of the disruptor nucleotide sequence with production of the fertility gene disruptor molecule, thereby resulting in disruption of the fertility gene. In these embodiments, crossing a breeding partner of the conditional infertility strain that is homozygous for the activator transgene with a breeding partner of the infertility-activating strain that is homozygous for the infertility-activating transgene produces non-human animal embryos with at least some germ cells having a homozygous disruption of the fertility gene.

In some embodiments, the expression-modulating element inhibits transcription of the disruptor nucleotide sequence under a first condition and disruption of the expression-modulating element may permit or enhance transcription of the disruptor nucleotide sequence under a second condition. In some embodiments, the expression-modulating element comprises an inhibitor nucleotide sequence (e.g., a transcription terminator) that inhibits expression of the disruptor nucleotide sequence and that is operably linked to recombinase recognition sites, wherein the recombinase recognition sites mediate disruption of the inhibitor nucleotide sequence in the presence of a recombinase. In illustrative examples of this type, the second breeding partner comprises an activator transgene comprising a coding sequence for the recombinase, operably connected to a promoter. The fertility gene of the second breeding partner is suitably a wild-type gene. In some embodiments, the first breeding partner is male and the second breeding partner is female.

In illustrative examples of this type, the disruptor nucleotide sequence is expressed conditionally by operably linking the disruptor nucleotide sequence to an inducible transcriptional regulation system. Transactivators produced from the activator transgene interact specifically with sequences engineered into regulatory elements operably connected to the disruptor nucleotide sequence to induce transcription of that nucleotide sequence in the presence of an expression product of the activator transgene. Thus, in these embodiments, the activator transgene typically comprises a nucleic acid sequence encoding a transcriptional inducer and the expression-modulating element comprises a binding site for the transcriptional inducer that is operably connected to the promoter of the disruptor nucleotide sequence, whereby production of the transcriptional inducer causes an increase or elevation in expression of the disruptor nucleotide sequence and in the level or functional activity of the fertility gene disruptor molecule. In representative examples of this type, the transcriptional inducer comprises (a) at least one transcriptional activation domain, and (b) at least one DNA-binding domain that binds to, or otherwise interacts with, the promoter which is operably connected to the disruptor nucleotide sequence and with which the DNA-binding domain(s) interact(s) to activate transcription of the disruptor nucleotide sequence. In operation, transcription of the activator transgene results in the production of the transcriptional inducer which, in turn, interacts via its DNA-binding domain(s) with the promoter of the disruptor nucleotide sequence and via its transcriptional activation domain with transcriptional machinery to activate transcription of the disruptor nucleotide sequence, which results in an increase or elevation in the level or functional activity of the fertility gene disruptor molecule.

Non-limiting examples of transcriptional activation domains include the acid transactivation domain (TAD) of HSV1-VP16 (e.g., amino acids 406 to 488, Triezenberg et al., 1988, *Genes & Development* 2:718-729; Triezenberg, 1995, *Current Opinions in Genetics and Development* 5:190-196; or amino acids 413 to 490, Regier et al., 1993, *Proc Natl Acad Sci USA.* 90(3):883-887; or amino acid 411 to 487; or amino acids 453-499; or amino acids 413 to 454; or amino acids 410 to 452, Walker et al., 1993, *Mol Cell Biol.* 13(9):5233-5244; amino acids 411 to 455, Nettelbeck et al., 1998, *Gene Ther.* 5(12):1656-1664), the activation domain of Oct-2 (e.g., amino acids 438 to 479, Tanaka et al., 1994, *Mol Cell Biol.* 14(9):6046-6055; or amino acids 3 to 154, Das et al., 1995, *Nature.* 374(6523):657-660), the activation domain of SP1 (e.g., amino acids 340 to 485, Courey and Tijan, 1988, *Cell.* 55(5):887-898), the activation domain of NFY (e.g., amino acids 1 to 233, Li et al., 1992, *J Biol Chem.* 267(13):8984-8990; van Hujisduijnen et al., 1990, *EMBO J.* 9(10):3119-3127; Sinha et al., 1995, *Proc Natl Acad Sci USA.* 92(5):1624-1628; Coustry et al. 1995, *J Biol Chem.* 270(1):468-475), the activation domain of ITF2 (e.g., amino acids 2 to 452, Seipel et al., 1992, *EMBO J.* 11(13):4961-4968), the activation domain of c-Myc (e.g., amino acids 1 to 262, Eilers et al. 1991, *EMBO J.* 10(1): 133-141), the activation domain of CTF (e.g., amino acids 399 to 499, Mermod et al., 1989, *Cell* 58(4):741-753; Das and Herr, 1993, *J Biol Chem* 268(33):25026-25032) or the activation domain of P65 (e.g., amino acids 286-550). In some embodiments, the DNA-binding domain is selected from the DNA-binding domain of the Gal4 protein (e.g., amino acids 1 to 147, Chasman and Kornberg, 1990, *Mol Cell Biol.* 10(6):2916-2923), the DNA-binding domain of the LexA protein (e.g., amino acids 1 to 81, Kim et al., 1992, *Science* 10; 255(5041):203-206; or amino acid 2-202; or the whole LexA protein e.g., amino acids 1 to 202, Brent and Ptashne, 1985, *Cell* 43(3 Pt 2):729-736), the DNA-binding domain of the lac repressor (Lad) protein (e.g., Brown et al., 1987, *Cell* 49(5):603-612; Fuerst et al., 1989, *Proc Natl Acad Sci USA.* 86(8):2549-2553), the DNA-binding domain of the tetracycline repressor (TetR) protein (e.g., Gossen et al., 1992, *Proc Natl Acad Sci USA.* 89(12):5547-5551; Dingermann et al., 1992, *EMBO J.* 11(4):1487-1492) or the DNA-binding domain of the ZFHD1 protein (e.g., Pomerantz et al., 1995, *Science* 267(5194):93-96). It is generally advantageous to add a nuclear localization signal (NLS) to the 3' end of the DNA-binding domain.

The promoter that is operably connected to the disruptor nucleotide sequence suitably comprises a cis-acting sequence with which the transcriptional inducer interacts. The cis-acting sequence comprises a binding sequence for the transcriptional inducer and particularly for its DNA-binding domain. The binding sequence, therefore, depends on the choice of the DNA-binding domain of the transcription factor used for the expression system, and includes, but is not limited to: (A) a binding sequence for the Gal4 protein such as but not limited to: nucleotide sequence: 5'-CGGACAACTGTTGACCG-3' [SEQ ID NO:3] as for example described by Chasman and Kornberg (1990, supra); or nucleotide sequence: 5'-CGGAGGACTGTCCTCCG 3' [SEQ ID NO:4]; or nucleotide sequence: 5'-CGGAGTACTGTCCTCCG-3' [SEQ ID NO:5] as for example disclosed by Giniger et al. (1988, *Proc Natl Acad Sci USA.* 85(2):382-386); (B) a binding sequence for the Gal4 protein such as but not limited to: nucleotide sequence: 5'-TACTGTATGTACATACAGTA-3' [SEQ ID NO:6]; or the LexA operator as for example disclosed by Brent and Ptashne (1984, *Nature* 312(5995):612-615); (C) a lac operator such as but not limited to nucleotide sequence: 5'-GAATTGTGAGGCTCACAATTC-3' [SEQ ID NO: 7], to which the Lad repressor protein binds, as for example described by Fuerst et al. (1989, supra) and Simons et al. (1984, *Proc Natl Acad Sci USA.* 81(6):1624-1628); (D) a tetracycline operator (tet 0) such as but not limited to nucleotide sequence: 5'-TCGAGTTTACCACTCCCTATCAGTGA-TAGAGAAAAGTGAAAG-3' [SEQ ID NO:8] to which the tetracycline repressor (TetR) protein binds; (E) a binding sequence for the ZFHD-1 protein such as but not limited to: nucleotide sequence: 5'-TAATGATGGGCG-3' [SEQ ID NO:9] as for example described by Pomeranz et al. (1995, supra); (F) a binding sequence for the c-Myc protein such as but not limited to: 5'-GGAAGCA-GACCAGCTGGTCTGCTTCC-3' [SEQ ID NO:10].

In other embodiments, conditional expression of the disruptor nucleotide sequence is regulated by a recombinase system that is used to turn on the expression of that sequence. In non-limiting examples of this type, the recombinase system comprises an intervening sequence interposed between a promoter and the disruptor nucleotide sequence, which suppresses or otherwise disrupts the transcription of the disruptor nucleotide sequence from the promoter. Suitably, the intervening sequence comprises a transcriptional terminator that inhibits or otherwise suppresses transcription of downstream sequences. Desirably, the intervening sequence comprises recombinase recognition sites that are specifically recognized by a site specific recombinase encoded by the activator transgene, to disrupt the intervening sequence in the presence of the recombinase and to thereby render the disruptor nucleotide sequence in operable linkage with the promoter and to permit transcription of that sequence. Alternatively, the recombinase system comprises a split or divided transgene including an upstream portion and a downstream portion of the disruptor nucleotide sequence and an excisable intervening sequence, which is interposed between the upstream and downstream portions. The upstream portion is operably connected to a promoter but the intervening sequence inhibits or otherwise suppresses transcription of the downstream portion, thereby preventing expression of a functional fertility gene disruptor molecule. Production of a site specific recombinase by expression of the disruptor nucleotide sequence excises the excisable intervening sequence to thereby render a full-length transcribable disruptor nucleotide sequence which permits production of a functional fertility gene disruptor molecule.

Thus, in some advantageous embodiments as noted above, the crossings will result in the generation of non-human embryos, which comprise in their germ line a disruption of the fertility gene, in which suitably both alleles of the fertility gene are disrupted and in which fertility (e.g., spermatogenesis or sperm function) is inhibited.

The present invention also extends to breeding pairs of non-human animals as broadly described above and elsewhere herein.

3.3 Donor Pluripotent Cells

Donor pluripotent cells are generally capable of differentiating into germ cells, such as ES cells, epi stem cells, EG cells and iPS cells. In specific embodiments, the pluripotent cell is an ES cell. Donor pluripotent cells may be genetically modified and in illustrative examples of this type comprise a transgene. The transgene can be introduced into a pluripotent cell using vectors that facilitate introduction of the transgene into the genome of the pluripotent cell (e.g., by random integration or homologous recombination), illustrative methods for which are disclosed in Transgenic Mouse: Methods and Protocols (Hofker, M H., 2003. *Methods Mol Biol.* 209:1-8), Advanced Protocols for Animal Transgenesis (2011, edited by S. Pease and T. L. Saunders, Springer Protocols Handbooks) and Transgenic Animals, Generation and Use (1997, edited by L. M. Houdebine, Hardwood Academic Publishers).

A donor pluripotent cell may be a male pluripotent cell (XY) or female pluripotent cell (XX), or an XO pluripotent cell. In specific embodiments, the donor pluripotent cell is a male pluripotent cell. Male (XY), female (XX) and XO pluripotent cells can be introduced into pre-implantation host embryos using any suitable technique.

Donor pluripotent cells from one species of non-human mammal can be introduced to a host of a different species of non-human mammal to produce germ cells derived from the donor pluripotent cells. In illustrative examples of this type, the donor pluripotent cells are derived from non-human primates, equines such as horses, sheep, goats, lagomorphs such as rabbits, dogs, cats, cattle, zoo animals as well as endangered or exotic mammals. In some embodiments, the donor pluripotent cells are iPS cells.

3.4 Non-Human Host Embryos

Non-human host embryos that may be used for introducing pluripotent cells include embryos of any non-human animal species, including non-human mammals, such as non-human primates and rodents. According to some embodiments of the present invention, the non-human host embryo is a rodent embryo, particularly a mouse or rat embryo. Generally, the non-human host embryo is from the same species as the pluripotent cell. However, in some embodiments, the non-human host embryo is from a different animal species (e.g., different mammalian species) than the pluripotent cell. The non-human host embryo into which the pluripotent cell is introduced is generally a pre-implantation non-human host embryo, including an embryo that is a 2-cell stage, a 4-cell stage, a 8-cell stage, a 16-cell stage, a 32-cell stage, a 64-cell stage embryo, a morula or a blastocyst. In some embodiments, the pre-implantation non-human host embryo is selected from a pre-morula stage, a morula stage, an uncompacted morula stage, a compacted morula stage and a blastocyst stage embryo. In some embodiments, the pre-implantation non-human host embryo is selected from the embryological age stages E1, E1.5, E2, E2.5, E3 and E3.5 for mouse embryos. Suitably the pre-implantation non-human host embryo is selected from host embryos having a developmental stage selected from a Theiler Stage 2 (TS2), a TS3, a TS4, a TS5 and a TS6, with reference to the Theiler stages as described in Theiler (1989) The House Mouse: Atlas of Mouse Development, by Theiler Springer-Verlag, NY. In specific embodiments, the pre-implantation non-human host embryo is selected from the Theiler stages TS3, TS4 and TS5. In other specific embodiments, the pre-implantation non-human host embryo is a morula. In still other specific embodiments, the pre-implantation non-human host embryo is a blastocyst.

Generally, one or more (e.g., 1, 2, 3, 4, 5, 6, 7, 8, 9, 10, 11, 12, 13, 14, 15, 16) donor pluripotent cells are introduced into a pre-implantation non-human (e.g., mouse or rat) host embryo that is suitably a 2-cell stage, a 4-cell stage, a 8-cell stage, a 16-cell stage, a 32-cell stage, a 64-cell stage embryo, a morula or a blastocyst. In some embodiments, the host pre-implantation embryo is a blastocyst and the number of donor pluripotent cells introduced is 6 to 12 cells. In illustrative examples of this type, the host embryo is an 8-cell stage embryo and the number of donor pluripotent cells is 2 to 10 cells.

3.5 Introduction of Pluripotent Cell into Host Embryo

Any suitable method can be used to introduce a donor pluripotent cell into a pre-implantation non-human host embryo. For example, groups of single donor pluripotent cells are selected using a finely drawn-out glass needle (20-25 micrometer inside diameter) and introduced through the embryo's zona pellucida for early-stage embryos and into the blastocysts cavity (blastocoel) using an inverted microscope fitted with micro-manipulators for blastocysts. Approximately 9-10 stem cells (ES or iPS or epi stem cells) are injected per blastocysts, or 8-cell stage embryo, 6-9 stem cells per 4-cell stage embryo, and about 6 stem cells per 2-cell stage embryo. Stem cell injection may be assisted with a laser or piezo pulses drilled opening the zona pellucida. (see Kraus et al., 2010, Genesis 48:394-399). Alternatively, stem cells can be aggregated with morula or injected into early stage embryos (e.g. 2-cell, 4-cell, 8-cell, premorula or morula) with or without the zona pellucida.

3.6 Gestation of Embryos, Chimeric Animals and Offspring

Gestating the embryos under conditions suitable for development of the embryos is performed according to standard methodology. The non-human embryos including donor pluripotent cells are implanted into pseudopregnant females as known in the art (see, Manipulating the Mouse Embryo: A Laboratory Manual, 3rd edition (A. Nagy et al. 2002, CSHL Press, ISBN-10: 0879695919; Nagy et al., 1990, Development 110, 815-821; U.S. Pat. Nos. 7,576,259, 7,659,442, 7,294,754, Kraus et al. 2010, Genesis 48, 394-399). Briefly, in specific rodent embodiments, fertile female rodents between 6-8 weeks of age are mated with vasectomized or sterile rodent males to induce a hormonal state receptive to supporting artificially introduced rodent embryos. Such females are termed pseudopregnant. At 2.5 dpc up to 15 of the stem cell containing blastocysts are introduced (implanted) into the uterine horn. For early stage embryos and morula, such embryos are either cultured in vitro into blastocysts or implanted into 0.5 dpc or 1.5 dpc pseudopregnant females according to the embryo stage into the oviduct.

Chimeric non-human animals developed from the implanted non-human embryos develop to term after the transfer, birth being dependent upon embryo age at implantation and species. Two types of chimeric non-human animals are produced by this process: those that comprise endogenous germ cells or gametes with a disrupted fertility gene, which are generally derived from the non-human host embryo, and those that comprise germ cells or gametes with a functional fertility gene, which are generally derived from the donor pluripotent cell.

When these chimeric non-human animals are bred to generate offspring with cognate non-human animals that comprise a functional fertility gene, the chimeric non-human animals that comprise endogenous germ cells or gametes having a disrupted fertility gene will have impaired or inhibited fertility, and thus will not produce offspring or produce very few offspring. However, the chimeric non-human animals that comprise germ cells or gametes derived from the donor pluripotent cell will have normal or unimpaired fertility, thereby enhancing the production of first litter offspring comprising germ cells or gametes derived from the donor pluripotent cell.

Standard analytical tools can be applied to test the identity of sperm or offspring. Methods include, but are not limited to, sequencing, Southern blot analysis, SNP analysis, PCR technologies as well as protein markers, coat color markers, isozyme analysis (e.g., GPI, glucose phosphate isomerase isozyme analysis) and detection of any reporter genes or transgenes present in the stem cells using standard methods well established in the art.

The gametes of the first litter offspring may be collected and used for in vitro fertilization (IVF) or artificial insemination (AI). The gametes isolated from the first litter offspring can also be cryopreserved and stored using methods known in the art. Alternatively, the germ cells of the first litter offspring may be collected, matured in vitro or in vivo and used for in vitro fertilization or artificial insemination.

IVF methodology is well-established. See, for example, Nagy et al. (2002, Manipulating the Mouse Embryo: A Laboratory Manual, 3rd edition, CSHL Press). IVF generally comprises collecting oocytes and sperm from a female and a male respectively, fertilizing oocytes from the female with sperm from the male and maintaining the resulting fertilized oocytes under suitable conditions for development of the fertilized oocytes into embryos. Embryos may be harvested at different stages. The female may be superovulated before oocytes are collected for IVF. Fertilization may be achieved by IVF, intracytoplasmic sperm injection or zona drilling. See, for example, Nagy et al. (2002, supra); Byers et al. (2006, *Theriogenology* 65:1716-26); Ostermeier et al. (2008, *PLOS One* 3(7):e2792). IVF can be a useful tool to increase the numbers of embryos obtained from a single female.

Intracytoplasmic sperm injection (ICSI) may be used to improve fertilization rates or to achieve fertilization. The ICSI procedure involves removal of the cumulus cells surrounding oocytes and injection of the sperm or haploid spermatids into the oocytes, ordinarily through a glass pipette (see, Kimura et al., 1995, *Biol Reprod.* 53(4):855-62). Spermatids, spermatogonial stem cells and male germ cells can be differentiated in vitro and then used for ICSI (Marh et al., 2003, *Biol Reprod* 69(1):169-76; Movahedin et al., 2004, *Andrologia* 36(5):269-76; Ogura et al., 1996, *J Assist Reprod Genet.* 13(5):4-31-4; Shinohara et al., 2002, *Hum Reprod* 17(12):3039-45; Chuma et al., 2005, *Development* 132(1):117-22).

As an alternative to collecting mature oocytes for IVF from a female, immature oocytes may be obtained and allowed to mature in vitro, a technique known as "in vitro maturation". In other embodiments, follicles, e.g., primary follicle or germ cells, may be isolated from the female and cultured in vitro to obtain oocytes useful for fertilization. In mammals, only a small fraction of immature oocytes develop into mature oocytes; the rest degenerate and die. By isolating immature oocytes from animals and allowing them to mature in vitro, one can obtain many more oocytes suitable for IVF from a given female in a short time frame. Mammalian oocytes are known to undergo maturation in vitro. In the case of mice, cattle and other mammals, in vitro matured oocytes have been fertilized in vitro and given rise to normal healthy offspring when embryos were transferred to an appropriate uterus (Schroeder et al., 1984, *Dev. Biol.* 102:493; Sirard et al., 1988, *Biol. Reprod.* 39:546). In vitro maturation technique is well known in the art. See, for example, Chiu et al. (2003, *Human Reprod.* 18: 408-416) and O'Brien et al. (2003, *Biol. Reprod.* 68:1682-1686).

Artificial insemination is a process of fertilizing female animals by manual injection or application of sperm. In such a procedure, male animals are not required at the time of insemination; stored sperm obtained from the animals can be used (see, Wolfe, 1967, *Lab Anim Care* 17(4):426-32 and Sato et al., 2002, *J Assist Reprod Genet.* 19(11):523-30).

Other methods that can be used to generate live offspring from the first litter offspring including surgical oocyte retrieval, ovary transfer, ovary splitting, ovary fragment transfer, in vitro maturation of oocytes, follicles, spermatogonial stem cells, in vitro differentiation of germ cells, and in vitro differentiation of primordial cells.

In some embodiments, gametes of a male first litter offspring are collected. In other embodiments germ cells or spermatogonial pluripotent cells of male first litter offspring are collected. In other embodiments gametes, germ cells or spermatogonial pluripotent cells are cryopreserved. In other embodiments, female first litter offspring are used to produce offspring by breeding. In still other embodiments gametes of female first litter offspring are isolated. In illustrative examples of this type, ovaries of the female first litter offspring are isolated. In other illustrative examples gametes or ovaries of female first litter offspring are cryopreserved.

In order that the invention may be readily understood and put into practical effect, particular preferred embodiments will now be described by way of the following non-limiting examples.

EXAMPLES

Example 1

Generation of Conditional GILZ (Tsc22d3) Knockout Mice

A targeting vector was constructed to flank exon 4 (ENSMUSE00000815383) of the mouse Tsc22d3 (ENSMUSG00000031431) gene with loxP sites via homologous recombination. Cre-recombinase mediated recombination of the loxP sites leads to the deletion of exon 4 (e.g., of transcript Tsc22d3-006 with the following Vega accession No. OTTMUST00000045354). The CDS of exon 4 codes for the complete sequence of the TSC22 (PF01166) domain. A schematic overview of the targeting vector is shown in FIG. 1.

A neomycin selection cassette (neo) for selection in ES cells was inserted downstream of exon 4. The selection cassette was flanked with FRT sites to enable removal by FLP-mediated recombination. Individual loxP sites were inserted upstream of exon 4 and downstream of the selection cassette. The 5' and 3' homology arms of the vector were approximately 8.0 kb and 6.0 kb, respectively.

The linearized targeting vector was electroporated into Bruce4 ES cells. Neomycin resistant clones were selected and screened by Southern blot analysis to identify correctly targeted clones. These clones were injected into BALB/c blastocysts which were subsequently transferred into pseudopregnant CBB6F1 foster females. The resulting chimeras were crossed to C57BL/6 females. Their offspring were selected by coat color and further analyzed by Southern blot analysis. The neomycin cassette was removed by crossing targeted mice to a C57BL/6 FLPe-recombinase strain.

Example 2

Generation of Targeted Mice Using Female Tsc22d3 Conditional Knockout Mice as Blastocyst Donors 21 to 25 day old Tsc22d3 conditional knockout female mice on a C57BL/6 background are injected with pregnant mare serum. Two days later the mice are injected with human chorionic gonadotropin and mated for 24 h to C57BL/6 Cre-recombinase males. Six days after the first injection blastocysts are extracted from the Tsc22d3 conditional knockout females. These blastocysts are used as recipients for microinjection of targeted BALB/c ES-cells and the microinjected blastocysts are transferred into pseudopregnant CBB6F1 foster females. The resulting chimeras are crossed to BALB/c females. Male chimeras with testis derived from blastocyst cells are expected to be sterile.

Example 3

Generation of Conditional Knockout Mice as Blastocyst Donors

Figure 2:
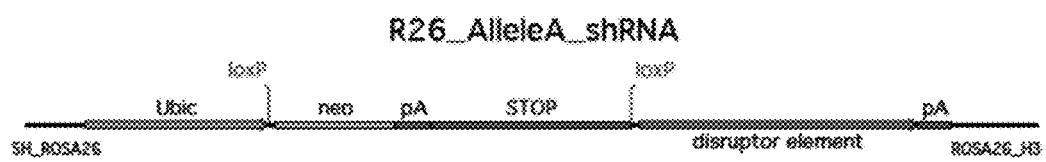
FIG. 2 is a schematic representation illustrating a targeted ROSA26 Allele Variant A. Ubic: human Ubiquitin promoter; neo: neomycin cassette for selection in ES cells; cre: Cre recombinase; STOP: transcriptional/translational 'stop' element; loxP: recognition sequence for Cre recombinase mediated STOP deletion; pA: polyadenylation signal; disruptor element: any element that disrupts the expression of a fertility gene or the function of its protein product (e.g., shRNA, antibody).

Conditional Knockout of a fertility gene ROSA26 Allele Variant A contains a nucleotide sequence that codes for a disruptor molecule (e.g., shRNA which has a transcript of a fertility gene as target, antibody directed against a protein that is encoded by a fertility gene, etc.). A floxed Stop cassette inhibits the expression of the disruptor molecule. An illustrative targeting vector for making a targeted ROSA26 Allele A is shown in FIG. 2.

Figure 3:
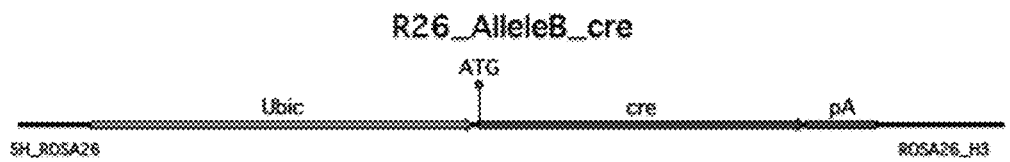
FIG. 3 is a schematic representation illustrating a targeted ROSA26 Allele Variant B. Ubic: human Ubiquitin promoter; neo: neomycin cassette for selection in ES cells; cre: Cre recombinase; STOP: transcriptional/translational 'stop' element; loxP: recognition sequence for Cre recombinase mediated STOP deletion; pA: polyadenylation signal; disruptor element: any element that disrupts the expression of a fertility gene or the function of its protein product (e.g., shRNA, antibody).

ROSA26 Allele Variant B contains the CDS for a Cre recombinase. An non-limiting example of a targeting vector for making a targeted ROSA26 Allele B is shown in FIG. 3.

Breeding partner one is homozygous for the ROSA26 Allele Variant A.

Breeding partner two is homozygous for the ROSA26 Allele Variant B.

Breeding partner one can be male or female. Breeding partner two vice versa.

Figure 4:
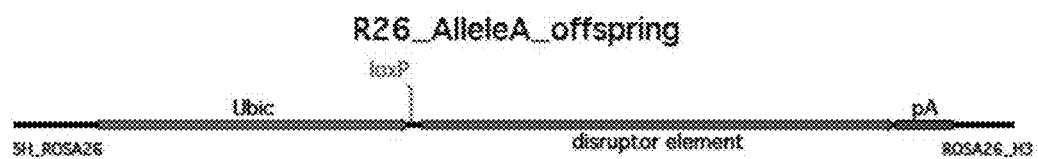
FIG. 4 is a schematic representation showing a targeted ROSA26 Allele Variant A in Offspring. Ubic: human Ubiquitin promoter; neo: neomycin cassette for selection in ES cells; cre: Cre recombinase; STOP: transcriptional/translational 'stop' element; loxP: recognition sequence for Cre recombinase mediated STOP deletion; pA: polyadenylation signal; disruptor element: any element that disrupts the expression of a fertility gene or the function of its protein product (e.g., shRNA, antibody).

The offspring from crossing Breeding partner one with Breeding partner two will result in embryos with one ROSA26 Allele Variant A and one ROSA26 Allele Variant B, as for example shown in FIG. 4. The recombinase of ROSA26 Allele Variant B will remove the STOP cassette in ROSA26 Allele Variant A and will thereby initiate the expression of the disruptor molecule. The disruptor molecule will now lead to a functional knock-out of the targeted fertility gene.

Example 4

Introduction of Pluripotent Cells into Embryos with Targeted Fertility Gene and Production of First-Litter Offspring Materials & Methods C57BL/6 Tsc22d3 conKO/conKO female mice or female wt control mice (BALB/c×C57BL/6 albino, agouti in case of targeted Bruce4 C57BL/6 ES-cells and C57BL/6 in case of targeted BALB/c ES-cells) were injected with pregnant mares serum (PMS) at 21-25 days of age. Two days later a subsequent injection of human chorionic gonadotropin (HCG) was applied. On the same day the C57BL/6 Tsc22d3 conKO/conKO female mice or the wt BALB/c×C57BL/6 albino, agouti mice (control) were mated to male mice with a knock-in (KI) of Cre recombinase in the ROSA26 locus (cre/cre) or male wt mice (control) respectively (the background of the male control mice was C57BL/6 in case of targeted BALB/c ES-cells and BALB/c in case of targeted Bruce4 C57BL/6 ES-cells). On the following day the mating partners were separated. The resulting blastocysts of the mating were harvested 3 days after the separation and used for injection of targeted BALB/c and Bruce4 C57BL/6 ES cells. The modified blastocysts were transferred into CBB6F1 recipients. About 9 weeks later the male chimeric offspring were mated to female BALB/c mice in case of targeted BALB/c cells and to female C57BL/6 mice in case of targeted Bruce4 C57BL/6 cells. The offspring were assessed for coat color at 10 days of age and genotyped at 21 days of age by Southern-Blot analysis.

Results

Injection of a Targeted BALB/c ES-Cell Line

Figure 5:
FIG. 5 is a photographic representation showing a non-limiting example of first-litter offspring produced by on embodiment of the method of the present invention. The pups shown in this figure are the complete litters of two chimeras. The chimeras were generated based on Tsc22d3 conKO/conKO blastocysts. All pubs show a white coat colour which is expected for animals derived from the targeted ES cell.

Injected Tsc22d3 KO/KO blastocysts were transferred into three recipients and resulted in 16 chimeras of which 11 were male which were used for further breeding. Five low percentage chimeras produced no offspring. The remaining six chimeras produced 181 pups in total. 146 of these animals were assessed for coat color, 35 were not determined. All 146 assessed animals (100%) had a white coat color as expected for animals which were derived from targeted BALB/c ES-cells (see, FIG. 5).

Figure 6:
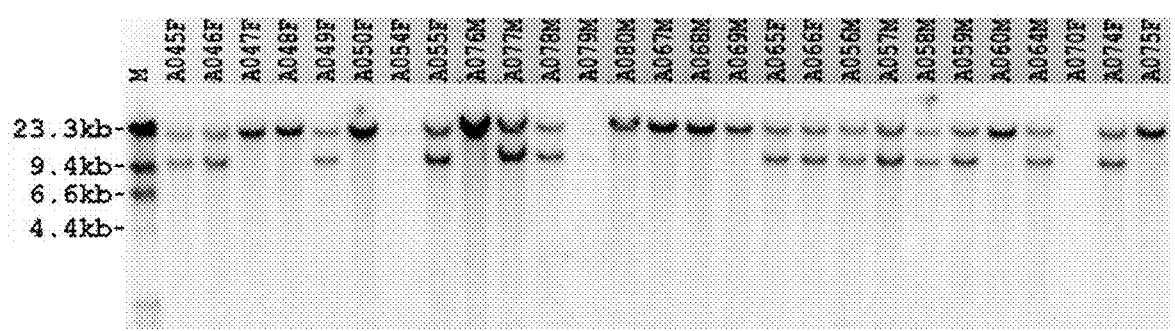
FIG. 6 is a photographic representation showing a representative example of a Southern-Blot Analysis for genotyping. Biopsy samples were lysed and digested with BamHI. The expected sizes are 17.5 kb for a wt allele and 9.7 kb for a targeted allele. A045, A046, A049, A055, A077, A078, A065, A066, A056, A057, A058, A059, A064 & A074 were determined as wt/targeted; A047, A048, A050, A076, A080, A067, A068, A069, A060, A070 & A075 were determined as wt/wt and A054, A079 &A070 could not be determined.

Sixty-three of these 146 animals were genotyped with Southern Blot Analysis ((see, FIG. 6, Southern Blot). Thirty-one (49%) animals were determined as wt/targeted and 32 (51%) as wt/wt mice.

As a control the same BALB/c ES-cell line was also injected into wt BALB/c×C57BL/6 albino blastocysts and transferred into 14 recipients. This resulted in a total of six chimeras of which five were male and one female. The 5 male chimeras produced a total of 155 pups. One-hundred and nineteen of these animals were assessed for coat color. Sixty (50%) mice had a white coat color (ES cell derived) and 59 (50%) an agouti coat color (blastocyst derived).

Injection of a Targeted C57BL/6 Bruce4 ES-Cell Line

Injected Tsc22d3 KO/KO blastocysts were transferred into two recipients and resulted in a total of three chimeras of which three were male. The chimeras produced ten pups in total. As the background of the Tsc22d3 KO/KO blastocysts (which were used to generate the chimeras) is C57BL/6×BALB/c F1 and the injected ES cells are on a Bruce4 C57BL/6 background, phenotyping based on the coat color was not possible. Instead, eight mice were genotyped by Southern-Blot analysis of which four (50%) were determined as wt/targeted and four (50%) as wt/wt mice. This correlates exactly with the ratio of wt/targeted mice vs. wt/wt mice that is expected if the offspring of the chimeras are derived only from the targeted ES-cell.

As a control, the same Bruce4 C57BL/6 ES-cell line was also injected into wt BALB/c×C57BL/6 albino, agouti blastocysts and transferred into 11 recipients. This resulted in a total of 13 chimeras of which eight were male and five female. The eight male chimeras produced a total of 324 pups. One-hundred and forty-nine of these animals were assessed for coat color. Fifty-two (35%) mice had a black coat color (ES cell derived) and 97 (65%) an agouti coat color (blastocyst derived).

Thus, use of Tsc22d3 KO/KO blastocysts as hosts of a genetically modified ES-cell line significantly improves germ line transmission of the genetic modification to progeny animals. Following this experiment, comparable improvements in germ line transmission have been achieved for eight other ES-cell lines carrying different genetic modifications.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method of producing male mouse embryos, wherein each and every male mouse embryo produced is infertile, the method comprising:
    crossing: 1) a first mouse breeding partner carrying a disruptable transgene that comprises a GILZ gene that is operably connected to a promoter and to recombinase recognition sites that mediate disruption of the GILZ gene in the presence of a recombinase, wherein disruption of the GILZ gene has been predetermined to lead to male infertility in a mouse of a genetic background, and wherein the first mouse breeding partner is female and is homozygous for the disruptable transgene;
    with 2) a second mouse breeding partner carrying a disruptor transgene that comprises a disruptor nucleotide sequence that is operably connected to a promoter and that encodes the recombinase that mediates disruption of the GILZ gene of the disruptable transgene, wherein the second mouse breeding partner is male and is homozygous for the disruptor transgene,
    to thereby generate a male mouse embryo that comprises germ cells having the GILZ gene disrupted therein, wherein mouse embryos produced from the crossing are of the genetic background in which disruption of the GILZ gene has been predetermined to lead to male infertility, and wherein each and every male mouse embryo produced from the crossing is infertile; and
    isolating the male mouse embryo.

2. The method according to claim 1, wherein the male mouse host embryo is a blastocyst.

3. The method according to claim 1, wherein the male mouse host embryo is an 8-cell stage embryo.

4. The method according to claim 1, further comprising introducing into the male mouse host embryo a donor pluripotent cell that comprises the GILZ gene lacking a disruption.

5. The method according to claim 4, wherein the pluripotent cell is a stem cell.

6. The method according to claim 4, wherein the pluripotent cell is an embryonic stem cell.

7. The method according to claim 4, wherein the pluripotent cell comprises a genetic modification in its genome.

8. The method according to claim 1, wherein the recombinase is selected from Cre, modified Cre, Dre, Hp, FLP-wild type (wt), FLP-L, FLPe, Flpo or phiC31.

9. The method according to claim 1, wherein the recombinase recognition sites are selected from loxP, FRT, rax and attP/B.

10. A method of producing a chimeric male mouse, the method comprising (1) implanting a male mouse embryo produced according to the method of claim 1 into a cognate pseudopregnant mouse, wherein the male mouse embryo comprises germ cells having the disrupted GILZ gene therein, wherein the male mouse embryo further comprises a donor pluripotent cell that comprises (a) the GILZ gene lacking a disruption, and (b) a genetic modification in its genome; and (2) gestating the male mouse embryo of (1) under conditions suitable for development of the embryo, thereby generating a chimeric male mouse with the disrupted GILZ gene and the genetic modification in its germ line.

11. A method of producing a mouse, the method comprising breeding a chimeric male mouse produced according to the method of claim 10 with a cognate female mouse that comprises in its genome the GILZ gene lacking a disruption, to produce a mouse that comprises the genetic modification when the chimeric male mouse comprises germ cells or gametes derived from the donor pluripotent cell.

12. The method of claim 1, wherein the first mouse breeding partner and the second mouse breeding partners each have a C57BL/6 genetic background.

* * * * *

```
                        SEQUENCE LISTING

<160> NUMBER OF SEQ ID NOS: 10

<210> SEQ ID NO 1
<211> LENGTH: 34
<212> TYPE: DNA
<213> ORGANISM: Artificial
<220> FEATURE:
<223> OTHER INFORMATION: loxP target site sequence

<400> SEQUENCE: 1
ataacttcgt atagcataca ttatacgaag ttat                         34

<210> SEQ ID NO 2
<211> LENGTH: 48
<212> TYPE: DNA
<213> ORGANISM: Artificial
<220> FEATURE:
<223> OTHER INFORMATION: FRT target site sequence

<400> SEQUENCE: 2
gaagttccta ttccgaagtt cctattctct agtaagtata ggaacttc          48

<210> SEQ ID NO 3
<211> LENGTH: 17
<212> TYPE: DNA
<213> ORGANISM: Artificial
<220> FEATURE:
<223> OTHER INFORMATION: binding sequence for the Gal4 protein

<400> SEQUENCE: 3
cggacaactg ttgaccg                                            17

<210> SEQ ID NO 4
<211> LENGTH: 17
<212> TYPE: DNA
<213> ORGANISM: Artificial
<220> FEATURE:
<223> OTHER INFORMATION: binding sequence for the Gal4 protein

<400> SEQUENCE: 4
cggaggactg tcctccg                                            17

<210> SEQ ID NO 5
<211> LENGTH: 17
<212> TYPE: DNA
<213> ORGANISM: Artificial
<220> FEATURE:
<223> OTHER INFORMATION: binding sequence for the Gal4 protein

<400> SEQUENCE: 5
cggagtactg tcctccg                                            17

<210> SEQ ID NO 6
<211> LENGTH: 20
<212> TYPE: DNA
<213> ORGANISM: Artificial
<220> FEATURE:
<223> OTHER INFORMATION: binding sequence for the Gal4 protein

<400> SEQUENCE: 6
```

```
tactgtatgt acatacagta                                                     20

<210> SEQ ID NO 7
<211> LENGTH: 21
<212> TYPE: DNA
<213> ORGANISM: Artificial
<220> FEATURE:
<223> OTHER INFORMATION: LexA operator

<400> SEQUENCE: 7
gaattgtgag gctcacaatt c                                                   21

<210> SEQ ID NO 8
<211> LENGTH: 42
<212> TYPE: DNA
<213> ORGANISM: Artificial
<220> FEATURE:
<223> OTHER INFORMATION: tetracycline operator

<400> SEQUENCE: 8
tcgagtttac cactccctat cagtgataga gaaaagtgaa ag                            42

<210> SEQ ID NO 9
<211> LENGTH: 12
<212> TYPE: DNA
<213> ORGANISM: Artificial
<220> FEATURE:
<223> OTHER INFORMATION: binding sequence for the ZFHD-1 protein

<400> SEQUENCE: 9
taatgatggg cg                                                             12

<210> SEQ ID NO 10
<211> LENGTH: 26
<212> TYPE: DNA
<213> ORGANISM: Artificial
<220> FEATURE:
<223> OTHER INFORMATION: binding sequence for the c-Myc protein

<400> SEQUENCE: 10
ggaagcagac cagctggtct gcttcc                                              26
```